(12) United States Patent
Kuroda et al.

(10) Patent No.: US 8,828,964 B2
(45) Date of Patent: Sep. 9, 2014

(54) CANCER CELL IDENTIFICATION MARKER AND CANCER CELL PROLIFERATION INHIBITOR

(75) Inventors: Masahiko Kuroda, Tokyo (JP); Masakatsu Takanashi, Kanagawa (JP); Kosuke Oikawa, Tokyo (JP)

(73) Assignees: Accural Inc., Tokyo (JP); MBC, Inc., Tokyo (JP); Takayuki Mizutani, Mie (JP)

( * ) Notice: Subject to any disclaimer, the term of this patent is extended or adjusted under 35 U.S.C. 154(b) by 139 days.

(21) Appl. No.: 13/613,626

(22) Filed: Sep. 13, 2012

(65) Prior Publication Data

US 2013/0172400 A1 Jul. 4, 2013

Related U.S. Application Data

(62) Division of application No. 12/441,747, filed as application No. PCT/JP2007/068129 on Sep. 19, 2007, now abandoned.

(30) Foreign Application Priority Data

Sep. 19, 2006 (JP) ................................ 2006-253258

(51) Int. Cl.
*C12N 15/113* (2010.01)
*C07H 21/04* (2006.01)

(52) U.S. Cl.
CPC .......... *C12N 15/113* (2013.01); *C12N 2310/11* (2013.01); *C12N 2310/14* (2013.01)
USPC ........................ 514/44 A; 536/24.5

(58) Field of Classification Search
None
See application file for complete search history.

(56) References Cited

PUBLICATIONS

Sharma, G. G. et al., "Human Heterochromatin Protein 1 Isoforms HP1$^{Hsα}$ and HP1$^{Hsβ}$ interfere with hTERT-Telomere Interactions and Correlate with Changes in Cell Growth and Response to Ionizing Radiation," Molecular and Cellular Biology, Nov. 2003, pp. 8363-8376.
Kirschmann, D. A. et al., "Down-Regulation of HP1$^{Hsα}$ Expression is associated with the metastatic phenotype in breast cancer," Cancer Research, 2000, vol. 60, pp. 3359-3363.
Norwood, L. E. et al., "A requirement for dimerization of HP1$^{Hsα}$ in Suppression of Breast Cancer Invasion," The Journal of Biological Chemistry, Jul. 7, 2006, vol. 281, No. 27, pp. 18668-18676.
Arney, K. L. et al., "Epigenetic aspects of differentiation," Journal of Cell Science, 2004, vol. 117, pp. 4355-4363.
Bernstein, E. et al., "Role for a bidentate ribonuclease in the initiation step of RNA interference," Nature, Jan. 18, 2001, vol. 409, pp. 363-366.
Cammas, F. et al., "Association of the transcriptional corepressor TIF1Beta with heterochromatin protein 1 (HP1): an essential role for progression through differentiation," Genes & Development, 2004, vol. 18, pp. 2147-2160.
Elbashir, S. M. et al., "Functional anatomy of siRNAs for mediating efficient RNAi in *Drosophila melanogaster* embryo lysate," The EMBO Journal, 2001, vol. 20, No. 23, pp. 6877-6888.
Fraga, M. F. et al., "Loss of acetylation at Lys16 and trimethylation at Lys20 of histone H4 is a common hallmark of human cancer," Nature Genetics, Apr. 2005, vol. 37, No. 4, pp. 391-400.
Gilbert, N. et al., "Formation of facultative heterochromatin in the absence of HP1," The EMBO Journal, 2003, vol. 22, No. 20, pp. 5540-5550.
Martinez, J. et al., "Single-stranded antisense siRNAs Guide Target RNA Cleavage in RNAi," Cell, Sep. 6, 2002, vol. 110, pp. 563-574.
Olins, D. E. et al., "Granulocyte heterochromatin: defining the epigenome," BMC Cell Biology, 2005, vol. 6, No. 39, pp. 1-14.
Popova, E. Y. et al., "Epigenetic heterochromatin markers distinguish terminally differentiated leukocytes from incompletely differentiated leukemia cells in human blood," Experimental Hematology, 2006, vol. 34, pp. 453-462.
Tenen, D. G., "Disruption of differentiation in human cancer: AML shows the way," Nature Reviews: Cancer, Feb. 2003, vol. 3, pp. 89-101.
Xu, P. et al., "The *Drosophila* MicroRNA Mir-14 Suppresses Cell Death and Is Required for Normal Fat Metabolism," Current Biology, Apr. 29, 2003, vol. 13, pp. 790-795.
Zhang, C. L. et al., "Association of Class II Histone Deacetylases with Heterochromatin Protein 1: Potential Role for Histone Methylation in Control of Muscle Differentiation," Molecular and Cellular Biology, Oct. 2002, vol. 22 No. 22, pp. 7302-7312.

*Primary Examiner* — Tracy Vivlemore
(74) *Attorney, Agent, or Firm* — Millen, White, Zelano & Branigan, P.C.

(57) ABSTRACT

Disclosed is an identification marker which can be utilized for detection of various human cancer cells and whose expression closely relates to malignant alteration of cells, and compositions for human cancer treatment which are based on suppression of cancer cell proliferation through inhibition of expression of the identification marker. The marker is human heterochromatin protein 1γ (HP1γ), and the compositions for cancer treatment comprises one or more agents which suppresses the expression of human HP1γ gene, such as siRNAs to human HP1γ.

8 Claims, 7 Drawing Sheets

CANCER CELL IDENTIFICATION MARKER AND CANCER CELL PROLIFERATION INHIBITOR

This application is a divisional of U.S. patent application Ser. No. 12/441,747, filed Mar. 18, 2009, which is a PCT National Stage entry based on PCT/JP2007/068129, filed Sep. 19, 2007.

TECHNICAL FIELD

The present invention relates to a cancer cell identification marker, a method for identification of cancer cells, cancer cell proliferation inhibitor agents, a composition for cancer treatment which contains one or more of the agents, a method for inhibition of cancer cell proliferation using the composition, a method for treatment of cancer in a human and other mammalian animals, and a method of screening for cancer cell proliferation inhibitor agents.

BACKGROUND ART

In recent years, so-called life-style related diseases such as cancer, heart diseases, cerebrovascular diseases, etc., have come to account for a major part of mortality in Japan, instead of infectious diseases like pneumonia and tuberculoses, which were dominant up to the early years of the Showa Era. Among others, lethality rate associated to cancer continuously showed a rapid increase, and has been ranking the top cause of death since around 1980 up to the present. Though some difference are found between sex and age, cancer has been found to develop in any organ or tissue of the body, including the brain, skin, blood, bronchi, lungs, stomach, liver, colon, uterus, breasts, pancreas, prostate gland, etc.

To diagnose cancer in such a variety of organs and tissues, while various measures have been employed, such as X-ray CT, MRI, ultrasonography, etc., identification markers for cancer cells also have come to be in use in clinical laboratory tests in recent years. Cancer cell identification markers are, for example, proteins produced by corresponding types of cancer cells, and they can be used to determine whether cancer cells are present in a sample, and also to know the type of the cancer cells which occur. In performing diagnosis of cancer based on a cancer identification marker, it is enough just to sample some cells from an organ or tissue to be diagnosed and then to examine the cells for any presence of that marker, by one of any convenient means, like antibody. It thus contributes to the convenience and reliability of the test, and also eases the burden on the patient as well. However, though some cancer identification markers can be used for detection of several different types of cells, the other, majority of markers are exclusively for a certain specific type of cancer cells. Thus it is in general necessary to use different identification markers in accordance with different organs or tissues to be examined. This increases the costs in preparing detection reagents corresponding to various identification markers, and, moreover, requires a change reagents and modification of the procedure during a detection process, thereby resulting as a whole in somewhat greater burden on the person who are engaged in diagnosis.

That there are a number of different types of cancers has also been posing a problem in cancer treatment by administration of drugs (chemotherapy). Namely, as its mechanism of development generally is intrinsic to each type of cancer, it is required in conducting chemotherapy to select the most suitable drugs for the type of the cancer about to be treated. Therefore, a wide range of drugs must be in stock to cope with a various types of cancers, and this poses a substantial burden due to cost increases and to the workload required in preparing drug formulations and giving treatment (see Non-patent Documents 1-8). Furthermore, there is a more serious problem in chemotherapy, that is, acquisition of resistance by cancer cells to the drugs that have been employed, and consequent reduction in efficacy of the treatment with them. In the etiology of cancer, a defect in cell differentiation is considered to be the major factor (see Non-patent Document 3). Thus, there would be possibilities of blocking cancer cell proliferation if a defect in cell differentiation (dedifferentiation) could be prevented.

On the other hand, a phenomenon called RNA interference (RNAi) has now been found in living organisms in common, from plants, insects, protozoa to mammalian animals, etc. RNAi is the phenomenon that a double-stranded RNA (dsRNA) which consists of a short sequence homologous to the mRNA produced by a target gene and a sequence complementary to the former, induces decomposition of that mRNA in the cell, thereby inhibiting the expression of the target gene.

It is assumed that regulation of the expression of a gene is done based on the formation of siRNA (small interfering RNA) and miRNA (microRNA, single-stranded RNA consisting of 21-23 bases) by the action of an enzyme "dicer", an endoribonuclease (see Non-patent Document 9). It is thought that in animals siRNAs take part in the cleavage of their respective target mRNAs (see Non-patent Document 10), and that miRNAs prevent the translation of their respective target mRNAs (see Non-patent Document 11). It has been found that either an siRNA or miRNA forms a complex with common proteins to convert them into an active form, which then was identified as RNA-induced silencing complex (RISC) containing as components a plurality of such proteins (see Non-patent document 12). So far, hundreds of miRNAs have been isolated and identified from animals and plants, and the physiological functions of at least four animal-derived miRNAs have been elucidated.

In 2001, it was reported that a 21-base, short double-stranded RNA induced RNAi effects more efficiently than others in mammalian animals. RNAi thus has been expected to be useful as a therapeutic means for intractable disorders such as cancer, viral diseases and neovascularization. In particular, siRNA has been found to be capable of efficiently decomposing and eliminating a certain mRNA at a very low concentration (1 nM), suggesting the presence of some enzymatic amplification.

Long double-stranded RNAs induce interferon synthesis and non-specific mRNA decomposition (interferon response). On the other hand, short dsRNAs inhibit also the expression of other genes than the one whose expression is intended to be suppressed in the case where their sequences are the same as or highly homologous to the mRNA of those genes (off-target effect).

Considering these, it is desirable that no such mRNA should exist that a given siRNA strongly binds to, among the mRNAs derived from other genes than the one whose expression is intended to be suppressed, or that, even if such a mRNA exists, it is the mRNA derived from a gene having a function similar to the very gene suppression of whose expression is intended. It is because, in such cases, it can be prevented that the siRNA should exhibit a wide-ranging non-specific suppressive effect on other functions than is intended.

[Non-patent Document 1] Zhang, C. L., McKinsey, T. A. & Olson, E. N. Association of class II histonedeacetylases with heterochromatin protein 1: potential role for histonemethylation in control of muscle differentiation. Mol Cell Biol 22, 7302-12 (2002)

[Non-patent Document 2] Cammas, F., Herzog, M., Lerouge, T., Chambon, P. & Losson, R. Association of the transcriptional corepressor TIF1beta with heterochromatin protein 1 (HP1): an essential role for progression through differentiation. Genes Dev 18, 2147-60 (2004)

[Non-patent Document 3] Tenen, D. G. Disruption of differentiation in human cancer: AML shows the way. Nat Rev Cancer 3, 89-101 (2003)

[Non-patent Document 4] Gilbert, N. et al. Formation of facultative heterochromatin in the absence of HP1. Embo J 22, 5540-50 (2003)

[Non-patent Document 5] Olins, D. E. & Olins, A. L. Granulocyte heterochromatin: defining the epigenome. BMC Cell Biol 6, 39 (2005)

[Non-patent Document 6] Popova, E. Y., Claxton, D. F., Lukasova, E., Bird, P. I. & Grigoryev, S. A. Epigenetichet-erochromatin markers distinguish terminally differentiated leukocytes from incompletely differentiated leukemia cells in human blood. Exp Hematol 34,453-62 (2006)

[Non-patent Document 7] Arney, K. L. & Fisher, A. G. Epigenetic aspects of differentiation. J Cell Sci 117,4355-63 (2004)

[Non-patent Document 8] Fraga, M. F. et al. Loss of acetylation at Lys16 and trimethylation at Lys20 of histoneH4 is a common hallmark of human cancer. Nat Genet 37, 391-400 (2005)

[Non-patent Document 9] Bernstein, E. et al., Nature 409: 363-366 (2001)

[Non-patent Document 10] Elbashir, S. M. et al., EMBO J 20:6877-6888(2001)

[Non-patent Document 11] Xu, P. et al., Curr Biol 13: 790-795 (2003)

[Non-patent Document 12] Martinet, J., et al., Cell 110:533-542(2002)

DISCLOSURE OF INVENTION

Against the above-mentioned background, an objective of the present invention is to provide a means which is commonly applicable for detection of cancer cells of a variety of origins.

Another objective of the present invention is to provide cancer cell proliferation inhibitor agents and compositions for cancer treatment both of which are commonly applicable to a wide variety of cancers.

Still another objective of the present invention is to provide a novel method of screening for proliferation inhibitor agents of a wide variety of cancers.

In the study in search of a method for identification of cancer cells and for treatment of cancer, the present inventors focused on the heterochromatin protein 1 (HP1) family, which are proteins involved in chromatin packaging and gene silencing. There are three homologues (α, β, γ) of the HP1 family in mammals, of which HP1α and β are present in heterochromatin, while HP1γ is present both in heterochromatin and euchromatin. Therefore, though it is thought to differ functionally from HP1α and HP1β, the function of HP1γ has not been known yet (Non-patent Document 1, Non-patent Document 2). The present inventors performed a study focusing on the relation between HP1γ and cell differentiation.

As a result, it was discovered that HP1γ protein, which is detectable in undifferentiated normal cells, gradually decreases in its expression levels as the cells differentiate, and becomes no longer detectable in fully differentiated normal cells; and further that HP1γ protein has not been lost but is expressed in various cancer cells, i.e., undifferentiated abnormal cells. On the basis of this finding, the present inventors have come to find that cancer cells can be distinguished from normal cells by utilizing HP1γ protein as an identification marker, i.e., by using its expression as an index. Furthermore, the present inventors surprisingly found that though its mechanism is yet unknown, proliferation of cancer cells can be potently inhibited by inhibiting the expression of HP1γ gene in those cells. The present invention was completed on the basis of these discoveries.

Thus, the present invention provides what follows.

1. A method for identifying a cell presented for examination as either being a cancer cell or a non-cancer cell, comprising the steps of
detecting expression of HP1γ in the cell presented for examination, and
identifying the cell as being a cancer cell if expression of HP1γ is detected in the cell, and as being a non-cancer cell if no expression of HP1γ is detected in the cell.

2. The method according to 1 above, wherein the cancer cell is an epithelial cancer cell and/or a non-epithelial cancer cell of a mammalian animal including a human, and wherein the HP1γ is HP1γ of the mammalian animal.

3. The method according to 1 or 2 above, wherein the cell presented for examination is a human cell and the HP1γ is human HP1γ.

4. A cancer cell proliferation inhibitor agent consisting of an inhibitor compound of HP1γ gene expression.

5. The cancer cell proliferation inhibitor agent according to 4 above, wherein the cancer cell is an epithelial cancer cell and/or a non-epithelial cancer cell of a mammalian animal including a human, and wherein the HP1γ is HP1γ of the mammalian animal.

6. The cancer cell proliferation inhibitor agent according to 4 or 5 above, wherein the inhibitor compound of HP1γ gene expression is an siRNA specific to HP1γ gene or an antisense DNA specific to HP1γ gene.

7. The cancer cell proliferation inhibitor agent according to one of 4 to 6 above, wherein the cancer cell is a human cancer cell, and wherein the HP1γ gene is human HP1γ gene.

8. The cancer cell proliferation inhibitor agent according to 7 above, wherein the inhibitor compound of HP1γ gene expression is an siRNA comprising at least one of the double-stranded RNAs each of which comprises a corresponding RNA strand set forth in the 5' to 3' direction in the following Tables 2A to 1F,;

9. The cancer cell proliferation inhibitor agent according to 8 above, wherein the double-stranded RNAs are selected from the group consisting of the double-stranded RNAs set forth as #5, #17, #35, #62, #89, #101, #102, #103, #104, #105 and #106 in Tables 2A to 1F.

10. The cancer cell proliferation inhibitor agent according to 8 above, wherein the double-stranded RNAs are selected from the group consisting of the double-stranded RNAs set forth as #17, #62 and #89 in Tables 2A to 1F.

11. The cancer cell proliferation inhibitor agent according to one of 8 to 10 above, wherein the siRNA has two-base overhangs on its both ends.

12. The cancer cell proliferation inhibitor agent according to one of 8 to 11 above, wherein each of the overhangs is on the 3' end of each of the strands forming the double-stranded RNA.

13. A composition for the treatment of cancer in a mammal including a human comprising, in a pharmaceutically acceptable carrier, one or more of the cancer cell proliferation inhibitor agents according to one of 6 to 12 above.

14. The composition for the treatment of cancer according to 13 above, wherein the cancer is caner in a human, the HP1γ gene is human HP1γ gene, and the inhibitor compound of HP1γ gene expression is an siRNA specific to human HP1γ gene.

15. The composition for the treatment of cancer in a human comprising, in a pharmaceutically acceptable carrier, one or more of the cancer cell proliferation inhibitor agents according to one of 8 to 12 above.

16. A method for the treatment of cancer in a mammal including a human comprising administering an effective amount of one or more of the cancer cell proliferation inhibitor agents according to one of 6 to 12 above, in a pharmaceutically acceptable carrier, to the mammal including a human in need thereof.

17. A method for the treatment of cancer in a human comprising administering an effective amount of one or more of the cancer cell proliferation inhibitor agents according to one of 8 to 12 above, in a pharmaceutically acceptable carrier, to the human in need thereof.

18. Use of one of the cancer cell proliferation inhibitor agents according to 8 to 12 above, for the production of a composition for the treatment of human cancer.

19. A method of screening for cancer cell proliferation inhibitor agents comprising the steps of;
bringing part of cancer cells into contact with candidate compounds,
separately detecting expression of HP1γ gene in those cancer cells which were brought into contact with the candidate compounds and in those cancer cells which were not brought into contact with a candidate compound,
determining whether or not HP1γ gene expression was inhibited in the cancer cells which were brought into contact with the candidate compounds by comparing the amount of expression of HP1γ gene in the cancer cells which were brought into contact with the candidate compounds with that in the cancer cells which were not brought into contact a candidate compound,
selecting, as cancer cell proliferation inhibitor agents, those candidate compounds which were brought into contact with those cancer cells in which inhibition of the expression was found.

The Effect of Invention

The present invention as identified above can be used in pathological examination and clinical diagnosis to distinguish not only some particular types cancers but also a wide variety of cancer cells from normal cells. Further, the present invention can be used to inhibit proliferation of not only some particular cancers but also of a wide variety of cancer cells, and therefore to treat cancers in a mammal including a human, in particular human cancers. Furthermore, the present invention enables screening for compounds which inhibit not only some particular cancers but also a wide variety of cancer cells.

BRIEF DESCRIPTION OF DRAWINGS

FIG. 1(A) is a set of autoradiograms showing the expression profiles of different proteins (HP1α, HP1αβ, HP1γ) in differentiation-induced 3T3-L1 mouse preadipocytes and human preadipocytes in one of the examples of the present invention;

FIG. 1(B) a set of autoradiograms showing the expression of HP1γ protein in 3T3-L1 in another example of the present invention; and FIG. 1(C) a set of photographs showing 3T3-L1 cells subjected to oil red-staining in still another example of the present invention.

FIG. 2(A) is a set of autoradiograms showing the time courses of histone modifications in 3T3-L1 cells during cell division in still another example of the present invention, FIG. 2(B) is a set of autoradiograms showing the time courses of the expression of HP1γ protein and of histone modifications, and FIG. 2(C) a set of autoradiograms showing the levels of histone modifications and HP1γ expression, after treated with siRNA specific to HP1 genes.

FIG. 4-2 is a set of photographs sowing the result of immunostaining of malignant tumor cells in still another example of the present invention.

FIG. 4-3 is a set of photographs sowing the result of immunostaining of malignant tumor cells in still another example of the present invention.

BEST MODE FOR CARRYING OUT THE INVENTION

Figure 1:
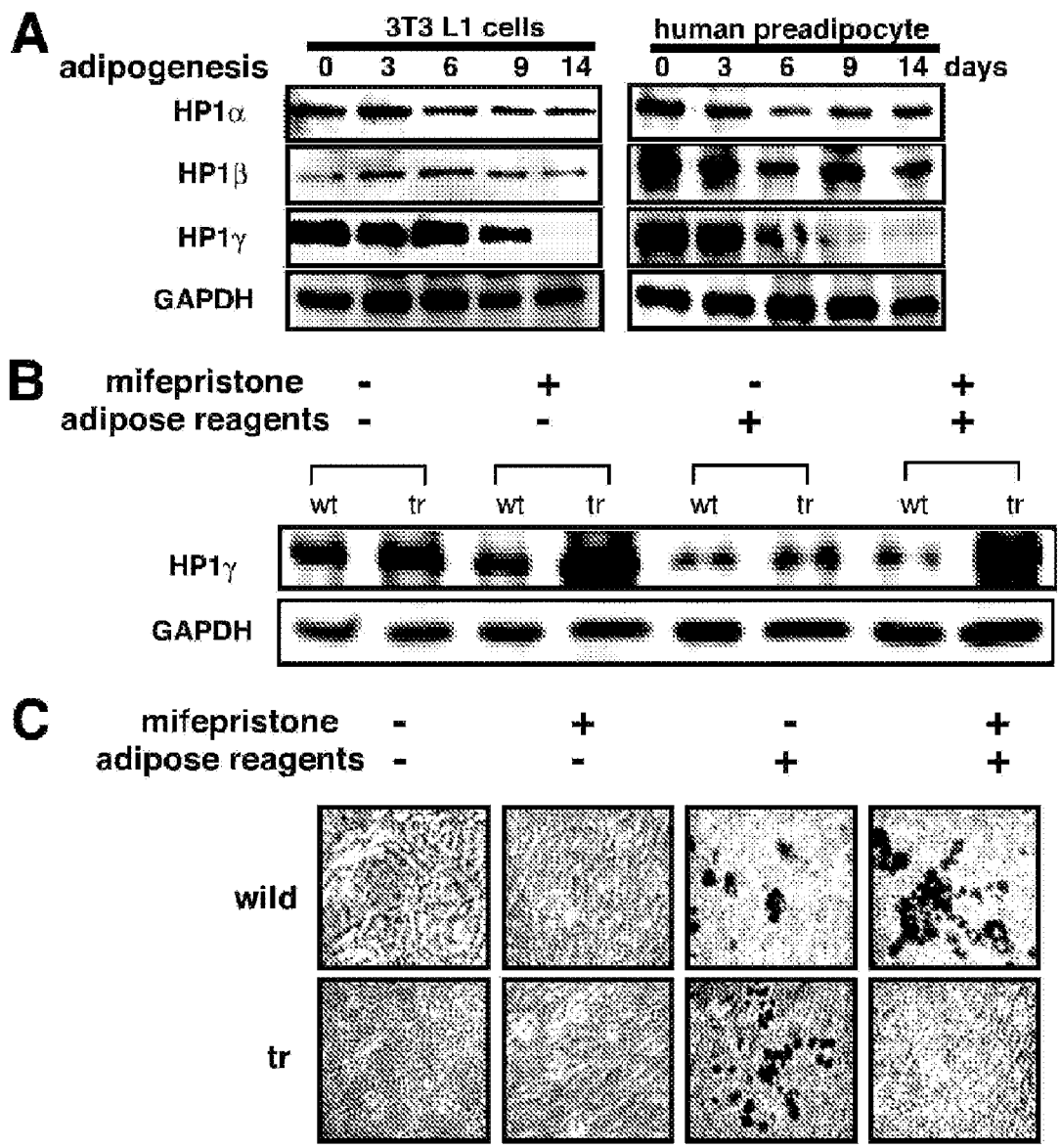
FIG. 4-1 is a set of photographs showing the result of immunostaining of malignant tumor cells in still another example of the present invention.

<Cancer Cell Identification Marker and Method for Identification>

The cancer cell identification marker according to the present invention is characterized in that it comprises HP1γ protein. And the method of identification of cancer cells according to the present invention is characterized in that it detects HP1γ protein in the cells. The nucleotide sequence for HP1γ gene is registered with GenBank accession NM_016587 (SEQ ID NO:125), within which the sequence consisting of 152-703 is the coding sequence (CDS) for HP1γ protein, and the sequence for HP1γ protein is registered with GenBank accession NP_057671.2 (SEQ ID NO:126).

According to the present invention, it is possible to detect HP1γ protein contained in the cell and thereby identify the cells in which HP1γ protein occurs as being cancer cells, thereby allowing to distinguish between cancer cells normal cells (normally differentiated cells).

There is no particular limitation regarding the types of cancer cells which can be identified by the method according to the present invention, and they include epithelial cancer cells, non-epithelial cancer cells, as well as those of solid and non-solid cancers. Cancers consisting of epithelial cancer cells include, for example, lung cancer, breast cancer, gastric cancer, colorectal cancer, uterine cervical cancer, uterine cancer (e.g., laryngeal cancer, pharyngeal cancer, lingual cancer, etc.), colon cancer, squamous cell carcinoma, adenocarcinoma and the like; cancers consisting of aforementioned non-epithelial cancer cells (sarcoma) include, for example, liposarcoma, osteosarcoma, chondrosarcoma, rhabdomyosarcoma, leiomyosarcoma, fibrosarcoma, angiosarcoma, and the like. Cells of other cancers also can be identified by the present invention, including, for example, basalioma, Merkel cell carcinoma, myxoma, non-small cell tumor, oat cell tumor, papilloma, bronchiolar tumor, bronchial tumor; leukemia such as B cell tumor, mixed cell tumor, null cell tumor, T cell tumor; HTLV-II related tumors such as lymphocyte acute leukemia, lymphocytic chronic tumor, mastocytoma, and myeloma; histiocytic malignant tumors such as Hodgkin's tumor, non-Hodgkin's lymphoma, malignant melanoma, mesothelioma, Ewing sarcoma, periosteoma, adenofibroma, adenolymphoma, craniopharyngioma, dysgerminoma, mesenchymoma, mesonephroma, ameloblastoma, cementoma, odontoma, thymoma, adenocarcinoma, cholangioma, cholesteatoma, cylindroma, cystic adenoma, cystic tumor, granulosa cell tumor, ovarian tumor, hepatic cancer, syringocarcinoma, islet cell tumor, Leydig cell tumor, Sertoli cell tumor, theca cell tumor, leiomyoma, myoblastoma, ependymoma, neural myoma, glioma, medulloblastoma, periosteoma, neurilemma, neuroblastoma, neuroepithelioma, neurofibroma, neuroma, paraganglioma, nonchromaffin paraganglioma, angiokeratoma, hematolymphangioma, sclerosing hemangioma, glomus tumor, angioendothelioma, lymphangioma, lymphangiomyoma, lymphagiosarcoma, pineocytoma, carcinosarcoma, colorectal sarcoma, neurofibroma and the like.

It is not limited how to detect HP1γ protein in the cells. Conventional western blotting may be employed, for example. More specifically, there is a method, for example, in which proteins are extracted from the cells to be examined which have been isolated from the living body, then are allowed to react with an HP1γ-specific antibody, and the antigen-antibody complex thus formed is detected. Examples of other methods for analysis include ELISA, immunohistochemical staining, flowcytometory, etc.

<Cancer Cell Proliferation Inhibitor Agents>

The proliferation inhibitors according to the present invention, as aforementioned, are cancer cell proliferation inhibitors which are characterized in that they contain one or more HP1γ gene expression inhibitors. As will be mentioned later, since lack of expression of HP1γ protein is closely correlated with differentiation of cells, and HP1γ protein thus is considered to work as a lock that blocks differentiation of cells, the proliferation inhibitors according to the present invention is expected to be useful for inducing cancer cells to differentiate.

In the present invention, there is no other particular limitation in the selection of aforementioned expression inhibitor compounds as far as they target the process of HP1γ gene expression and inhibit it. For example, it may inhibit any step of the process, which includes the steps of transcription of DNA into RNA, splicing of pre-mRNA (hnRNA) to form mRNA, translation of mRNA into HP1γ protein, and the like. Typical examples of such expression inhibitor compounds include siRNAs and antisenses, of which particularly preferred is siRNAs.

"SiRNA" (small interfering RNA) is a short double-stranded RNA that mediates RNA interference and generally a low molecular-weight double-stranded RNA which is 21 to 27 base long including overhangs consisting of some 2 bases (2 mer) on the both ends.

The aforementioned siRNAs that inhibit HP1γ expression are those siRNAs which contain sequences complementary to the transcript of HP1γ presented as SEQ ID NO:125, and preferably double-stranded siRNAs consisting of 21-base strands each of which consists of 19 bases that forms the double-stranded portion of the RNA, and a 2-base (2 mer) overhang on one end of each strand. In general, the overhangs are preferably 3'-end overhangs.

The term "3'-end overhang" means a nucleotide portion that projects on each 3'-end of a double-stranded RNA which is formed of two RNA strands comprising complementary sequences and paired with each other. Examples of 2-base sequences which form the aforementioned 3'-end overhangs include, but are not limited to, TT (-thymine-thymine), AU (-adenine-uracil), AG (-adenine-guanine), etc. The overhang portions of the sense strand of siRNA (having the same nucleotide sequence as that of the target transcript) and the antisense strand of it (having the complementary sequence to that of the target transcript) may be of the same or different sequences with each other. It may be, for example, that the overhang of the sense strand is AG, while the overhang of the antisense strand is AU, or that the overhang of the sense strand is AU, while the overhang of the antisense strand is AG.

Further, the 2-base sequences that may form 3'-end overhangs are not limited to the above-mentioned sequences, but they may be any one of naturally occurring nucleotide bases (adenine, guanine, thymine, cytosine, and uracil) or any other naturally occurring or artificial modified bases known in the art, as far as they do not substantially affect the RNAi effect. The nucleotides forming the 3'-end overhang may generally be, but are not limited to, ribonucleotides, but deoxyribonucleotides, modified ribonucleotides, or other nucleotide analogues, as far as they do not substantially affect the RNAi effect. Still further, in the present invention, the aforementioned double stranded siRNAs, when needed, may have 5'-end overhangs instead of 3'-end ones.

Thought not limited to them, candidate sequences that may be employed as the aforementioned 19-base pair portion may be the sequences presented in Table 1 (it should be noted that only the sense sequences are presented). In the table, the column "Gene" indicates the position of the target base (corresponding to the 5'-end of the sense strand of siRNA) in the transcript (mRNA) of HP1γ gene set forth as SEQ ID NO:125 presented in Table 1 (the headmost base is assigned number 1), and the column "CDS" indicates the position number of the target base of the siRNA as counted from the headmost base of the coding sequences for the amino acids of HP1γ protein. In the table, the sequences up to the sequence presented at Gene 684 are in the coding region, and the sequences following the sequence presented at Gene 827 are in the non-coding region.

TABLE 1

Table 1

| Gene | CDS | Sequence (5'→3') | SEQ ID NO: |
|---|---|---|---|
| 40 | | CCCUUCGGAUGUGGCUUGA | 2 |
| 41 | | CCUUCGGAUGUGGCUUGAG | 3 |
| 42 | | CUUCGGAUGUGGCUUGAGC | 4 |
| 43 | | UUCGGAUGUGGCUUGAGCU | 5 |
| 44 | | UCGGAUGUGGCUUGAGCUG | 6 |
| 45 | | CGGAUGUGGCUUGAGCUGU | 7 |
| 46 | | GGAUGUGGCUUGAGCUGUA | 8 |
| 47 | | GAUGUGGCUUGAGCUGUAG | 9 |
| 48 | | AUGUGGCUUGACCUGUAGG | 10 |
| 49 | | UGUGGCUUGAGCUGUAGGC | 11 |

TABLE 1-continued

Table 1

| Gene | CDS | Sequence (5'→3') | SEQ ID NO: |
|---|---|---|---|
| 50 | | GUGGCUUGAGCUGUAGGCG | 12 |
| 51 | | UGGCUUGAGCUGUAGGCGC | 13 |
| 106 | | CAGCUCGGAGGCGGUGAAU | 14 |
| 107 | | AGCUCGGAGGCGGUGAAUA | 15 |
| 108 | | GCUCGGAGGCGGUGAAUAA | 16 |
| 109 | | CUCGGAGGCGGUGAAUAAU | 17 |
| 123 | | AUAAUAGCUCUUCAAGUCU | 18 |
| 124 | | UAAUAGCUCUUCAAGUCUG | 19 |
| 125 | | AAUAGCUCUUCAAGUCUGC | 20 |
| 126 | | AUAGCUCUUCAAGUCUGCA | 21 |
| 127 | | UAGCUCUUCAAGUCUGCAA | 22 |
| 128 | | AGCUCUUCAAGUCUGCAAU | 23 |
| 129 | | GCUCUUCAAGUCUGCAAUA | 24 |
| 130 | | CUCUUCAAGUCUGCAAUAA | 25 |
| 131 | | UCUUCAAGUCUGCAAUAAA | 26 |
| 148 | | AAAAAUGGCCUCCAACAAA | 27 |
| 149 | | AAAAUGGCCUCCAACAAAA | 28 |
| 150 | | AAAUGGCCUCCAACAAAAC | 29 |
| 151 | | AAUGGCCUCCAACAAAACU | 30 |
| 152 | | AUGGCCUCCAACAAAACUA | 31 |
| 153 | | UGGCCUCCAACAAAACUAC | 32 |
| 154 | | GGCCUCCAACAAAACUACA | 33 |
| 155 | | GCCUCCAACAAAACUACAU | 34 |
| 156 | | CCUCCAACAAAACUACAUU | 35 |
| 157 | | CUCCAACAAAACUACAUUG | 36 |
| 158 | | UCCAACAAAACUACAUUGC | 37 |
| 159 | | CCAACAAAACUACAUUGCA | 38 |
| 160 | 9 | CAACAAAACUACAUUGCAA | 39 |
| 191 | 40 | AAACAGAAUGGAAAGAGUA | 40 |
| 194 | 43 | CAGAAUGGAAAGAGUAAAA | 41 |
| 194 | 43 | CAGAAUGGAAAGAGUAAAA | 42 |
| 216 | 65 | UUGAAGAGGCAGAGCCUGA | 43 |
| 222 | 71 | AGGCAGAGCCUGAAGAAUU | 44 |
| 223 | 72 | GGCAGAGCCUGAAGAAUUU | 45 |
| 231 | 80 | CUGAAGAAUUUGUCGUGGA | 46 |
| 232 | 81 | UGAAGAAUUUGUCGUGGAA | 47 |
| 234 | 83 | AAGAAUUUGUCGUGGAAAA | 48 |

TABLE 1-continued

Table 1

| Gene | CDS | Sequence (5'→3') | SEQ ID NO: |
|---|---|---|---|
| 247 | 96 | GGAAAAAGUACUAGAUCGA | 49 |
| 253 | 102 | AGUACUAGAUCGACGUGUA | 50 |
| 259 | 108 | AGAUCGACGUGUAGUGAAU | 51 |
| 265 | 114 | ACGUGUAGUGAAUGGGAAA | 52 |
| 271 | 120 | AGUGAAUGGGAAAGUGGAA | 53 |
| 273 | 122 | UGAAUGGGAAAGUGGAAUA | 54 |
| 330 | 179 | CUUGGGAACCUGAAGAAAA | 55 |
| 360 | 209 | CAGAAUUGAUUGAAGCGUU | 56 |
| 361 | 210 | AGAAUUGAUUGAAGCGUUU | 57 |
| 388 | 237 | UCAGAAAGCUGGCAAAGAA | 58 |
| 389 | 238 | CAGAAAGCUGGCAAAGAAA | 59 |
| 391 | 240 | GAAAGCUGGCAAAGAAAAA | 60 |
| 399 | 248 | GCAAAGAAAAAGAUGGUAC | 61 |
| 400 | 249 | CAAAGAAAAAGAUGGUACA | 62 |
| 441 | 290 | GUGAAUCUGAUGACAGCAA | 63 |
| 453 | 302 | ACAGCAAAUCAAAGAAGAA | 64 |
| 453 | 302 | ACAGCAAAUCAAAGAAGAA | 65 |
| 461 | 310 | UCAAAGAAGAAAAGAGAUG | 66 |
| 469 | 318 | GAAAAGAGAUGCUGCUGAC | 67 |
| 472 | 321 | AAGAGAUGCUGCUGACAAA | 68 |
| 482 | 331 | GCUGACAAACCAAGAGGAU | 69 |
| 484 | 333 | UGACAAACCAAGAGGAUUU | 1 |
| 541 | 390 | AGACAGCAGUGGAGAAUUG | 70 |
| 566 | 415 | CUCAUGAAAUGGAAAGAUU | 71 |
| 594 | 443 | CAGACUUGGUGCUGGCGAA | 72 |
| 608 | 457 | GCGAAAGAGGCAAAUAUGA | 73 |
| 609 | 458 | CGAAAGAGGCAAAUAUGAA | 74 |
| 684 | 533 | CAGAAGAUGAAGCUCAAUA | 75 |
| 827 | | UGAAAGUAGCGUUGGAAGA | 76 |
| 936 | | CAUUUGAUACCAUGGUAUA | 77 |
| 996 | | GGGAAAUGUCCAUAGUCAU | 78 |
| 997 | | GGAAAUGUCCAUAGUCAUU | 79 |
| 1020 | | AGUCAAAACUUGUGUUCUC | 80 |
| 1196 | | GCCAUUAUUCCAAGCAAAA | 81 |
| 1219 | | AGAUAAUCCCUUCAAGUUA | 82 |
| 1220 | | GAUAAUCCCUUCAAGUUAA | 83 |
| 1258 | | CCAUACAUUUCAAGUGAAA | 84 |

TABLE 1-continued

Table 1

| Gene | CDS | Sequence (5'→3') | SEQ ID NO: |
|---|---|---|---|
| 1346 | | GCAAAAUUCCUAAAAGGAA | 85 |
| 1404 | | GAUGAGGAAACUAGACAAA | 86 |
| 1409 | | GGAAACUAGACAAAUGCUA | 87 |
| 1417 | | GAGAAAUGCUAGUGUGUUU | 88 |
| 1487 | | GGGCCAUUCCUUAGCAAAA | 89 |
| 1576 | | AAACCUAAUCAGAUGGUUA | 90 |
| 1684 | | UCAGAUGGUUAGAGGUGUU | 91 |
| 1590 | | GGUUAGAGGUGUUGGCAGU | 92 |
| 1621 | | GUCAUAAAUGUGUGAACAA | 93 |
| 1719 | | CUUUACUGGUUCAGCAAAA | 94 |
| 1730 | | CAGCAAAAGCCAGGAAGAA | 95 |
| 1732 | | GCAAAAGCCAGGAAGAACA | 96 |
| 1799 | | UGUAAAUACUGGUGAACAG | 97 |

Within the nucleotide sequence of the transcript (mRNA) of HP1γ including the nucleotide sequences listed in Table 1, every 19-base fragment sequence starting from each position was examined as to whether the short RNA of 19-base pairs having the same sequence as the fragment sequence is (a) expected to have desired potent RNAi effects on HP1γ mRNA, and whether (b), in order for avoiding the problem of off-target effects, the short RNA is highly specific to HP1γ mRNA, i.e., has only a little probability of binding to the nucleotide sequences of other genes than HP1γ. Those sequences that met the both purposes were picked out.

In the above, analysis of RNA interference with each of the sequences was done based on their Tm value, GC content, and the distribution of particular bases. Tm (melting temperature) is the temperature at which 50% of a double-stranded nucleotide will be dissociated to single-stranded nucleotides, and can be calculated according to a well known method (see e.g., Breslauer K J et al. (1986) Proc. Natl. Acad. Sci. USA. 83: 3746-3750., Rychlik W et al. (1990) Nucleic Acids Res. 18, 6409-6412. or Owczarzy R et al. (1997), Biopolymers 44: 217-239). In consideration of the distribution of particular bases, the disclosure in WO 2006/060454 (Title of invention: "Methods of Designing Small Interfering RNAs, Antisense Polynucleotides and other Hybridizing Polynucleotides") was followed.

Selection of sequences which are highly specific to HP1γ mRNA was conducted by searching, within the sequences of the genes that are registered in GenBank (either the genes actually identified or hypothetical genes which were only predicted based on computer analysis), for those containing a sequence which is either fully identical to (19/19), differs only in a single base from (18/19), or differs only in two bases (17/19) from the sense or the antisense strand of each siRNA that has a double-stranded portion made of any one of the sequences presented above as a sense strand, and an antisense strand having a sequence complementary to it. Heaviest regard was given to the fact that no other gene than HP1γ is found that contains a sequence fully identical (19/19) to it, and less heavy regard was given to the fact that a sequence exists which differs only in one base (18/19) or in two bases (17/19), in the order. This is because as the number of the bases increases at which two sequences do not match, the probability of their forming a pair reduces rapidly, therefore making any off-target effect weaker or negligible. Again, the less heavy regard was given to such genes that are not HP1γ gene but were registered as being similar to HP1γ, for they were considered to be performing similar functions to that of HP1γ. Furthermore, the less heavy regard was given to hypothetical genes whose existence was predicted merely on computer, since their real existence had not been verified.

The following Tables 2A to 2F shows (the double-stranded portions) of 106 siRNA candidates selected through the process described above. In each double-stranded RNA portion in the Tables, the upper one is the sense sequence and the lower one the antisense sequence, both of which are presented with their 5'-end placed at the top. Further, in the Tables, the numbers in brackets indicate the number of registrations of a gene which, though being one and same gene, is registered with different accession numbers.

On both ends of each double-stranded RNA shown in Tables 2A to 2F may be attached desired overhang sequences (e.g., TT, UU and the like), and an siRNA thus obtained exhibits a strong RNA inhibitory effect, with minimized off-target effect.

TABLE 2A

| | SEQ ID NO: | gene | CDS | Candidate sequence | GC % | Position Score | 19/19 | | 18/19 | | 17/19 | |
|---|---|---|---|---|---|---|---|---|---|---|---|---|
| #1 | 39 192 | 160 | 9 | CAACAAAACUACAUUGCAA UUGCAAUGUAGUUUUGUUG | 31% | 137 | 3 | (2) | 2 | (2) | | |
| #2 | 127 193 | 190 | 39 | AAAACAGAAUGGAAAGAGU ACUCUUUCCAUUCUGUUUU | 31% | 80 | 4 | (3) | 2 | (2) | 7 2 | (6) (2) |
| #3 | 40 194 | 191 | 40 | AAACAGAAUGGAAAGAGUA UACUCUUUCCAUUCUGUUU | 31% | 92 | 5 | (4) | 1 | (1) | 4 4 | (3) (3) |
| #4 | 128 195 | 192 | 41 | AACAGAAUGGAAAGAGUAA UUACUCUUUCCAUUCUGUU | 31% | 77 | 5 | (4) | 1 1 | (1) (1) | 2 2 | (2) (1) |
| #5 | 41 196 | 194 | 43 | CAGAAUGGAAAGAGUAAAA UUUUACUCUUUCCAUUCUG | 31% | 124 | 5 | (4) | | | 6 | (6) |

TABLE 2A-continued

| SEQ ID NO: | Position gene | CDS | Candidate sequence | GC % | Score | Position 19/19 | | 18/19 | | 17/19 | |
|---|---|---|---|---|---|---|---|---|---|---|---|
| #6 | 129 197 | 210 | 59 AAAAAGUUGAAGAGGCAGA UCUGCCUCUUCAACUUUUU | 36% | 95 | 5 | (4) | 2 | (2) | 11 | (9) |
| #7 | 130 198 | 214 | 63 AGUUGAAGAGGCAGAGCCU AGGCUCUGCCUCUUCAACU | 52% | 63 | 5 | (4) | | | 7 1 | (6) (1) |
| #8 | 43 199 | 216 | 65 UUGAAGAGGCAGAGCCUGA UCAGGCUCUGCCUCUUCAA | 52% | 104 | 5 | (4) | 2 | (1) | 4 2 | (4) (2) |
| #9 | 44 200 | 222 | 71 AGGCAGAGCCUGAAGAAUU AAUUCUUCAGGCUCUGCCU | 47% | 127 | 5 | (4) | 2 | (1) | 5 1 | (5) (1) |
| #10 | 45 201 | 223 | 72 GGCAGAGCCUGAAGAAUUU AAAUUCUUCAGGCUCUGCC | 47% | 90 | 5 | (4) | 2 | (1) | 7 1 | (6) (1) |
| #11 | 46 202 | 231 | 80 CUGAAGAAUUUGUCGUGGA UCCACGACAAAUUCUUCAG | 42% | 93 | 3 | (2) | 4 | (3) | 2 | (2) |
| #12 | 47 203 | 232 | 81 UGAAGAAUUUGUCGUGGAA UUCCACGACAAAUUCUUCA | 36% | 91 | 3 | (2) | 4 | (3) | 2 | (2) |
| #13 | 48 204 | 234 | 83 AAGAAUUUGUCGUGGAAAA UUUUCCACGACAAAUUCUU | 31% | 137 | 3 | (2) | 2 | (2) | 3 5 | (3) (3) |
| #14 | 131 205 | 235 | 84 AGAAUUUGUCGUGGAAAAA UUUUUCCACGACAAAUUCU | 31% | 72 | 3 | (2) | 2 | (2) | 3 4 | (3) (3) |
| #15 | 132 206 | 241 | 90 UGUCGUGGAAAAAGUACUA UAGUACUUUUUCCACGACA | 36% | 57 | 3 | (2) | 4 | (3) | | |
| #16 | 133 207 | 246 | 95 UGGAAAAAGUACUAGAUCG CGAUCUAGUACUUUUUCCA | 36% | 66 | 3 | (2) | 2 | (2) | | |
| #17 | 49 208 | 247 | 96 GGAAAAAGUACUAGAUCGA UCGAUCUAGUACUUUUUCC | 36% | 138 | 3 | (2) | 2 | (2) | 1 | (1) |
| #18 | 50 209 | 253 | 102 AGUACUAGAUCGACGUGUA UACACGUCGAUCUAGUACU | 42% | 99 | 3 | (2) | 2 | (2) | | |

TABLE 2B

| SEQ ID NO: | Position gene | CDS | Candidate sequence | GC % | Score | Position 19/19 | | 18/19 | | 17/19 | |
|---|---|---|---|---|---|---|---|---|---|---|---|
| #19 | 51 210 | 259 | 108 AGAUCGACGUGUAGUGAAU AUUCACUACACGUCGAUCU | 42% | 101 | 3 | (2) | 2 | (2) | 2 | (2) |
| #20 | 134 211 | 264 | 113 GACGUGUAGUGAAUGGGAA UUCCCAUUCACUACACGUC | 47% | 65 | 5 | (4) | 2 | (2) | | |
| #21 | 52 212 | 265 | 114 ACGUGUAGUGAAUGGGAAA UUUCCCAUUCACUACACGU | 42% | 107 | 5 | (4) | 2 | (2) | 4 | (1) |
| #22 | 53 213 | 271 | 120 AGUGAAUGGGAAAGUGGAA UUCCACUUUCCCAUUCACU | 42% | 85 | 5 | (4) | | | 8 1 | (7) (1) |
| #23 | 135 214 | 272 | 121 GUGAAUGGGAAAGUGGAAU AUUCCACUUUCCCAUUCAC | 42% | 63 | 5 | (4) | 2 | (1) | 5 | (5) |
| #24 | 54 215 | 273 | 122 UGAAUGGGAAAGUGGAAUA UAUUCCACUUUCCCAUUCA | 36% | 107 | 5 | (4) | 2 | (1) | 3 | (3) |
| #25 | 136 216 | 293 | 142 UUCCUGAAGUGGAAGGGAU AUCCCUUCCACUUCAGGAA | 47% | 64 | 5 | (4) | | | 6 2 | (6) (1) |
| #26 | 137 217 | 294 | 143 UCCUGAAGUGGAAGGGAUU AAUCCCUUCCACUUCAGGA | 47% | 68 | 5 | (4) | 3 | (3) | 2 | (2) |
| #27 | 138 218 | 296 | 145 CUGAAGUGGAAGGGAUUUA UAAAUCCCUUCCACUUCAG | 42% | 75 | 5 | (4) | | | 4 3 | (3) (2) |

TABLE 2B-continued

| SEQ ID NO: | Position gene | CDS | Candidate sequence | GC % | Score | Position 19/19 | | 18/19 | | 17/19 | |
|---|---|---|---|---|---|---|---|---|---|---|---|
| #28 139 219 | 301 | 150 | GUGGAAGGGAUUUACAGAU AUCUGUAAAUCCCUUCCAC | 42% | 60 | 5 | (4) | 4 | (3) | 4 2 | (4) (2) |
| #29 140 220 | 302 | 151 | UGGAAGGGAUUUACAGAUG CAUCUGUAAAUCCCUUCCA | 42% | 72 | 5 | (4) | 4 | (3) | 4 2 | (4) (2) |
| #30 141 221 | 310 | 159 | AUUUACAGAUGCUGACAAU AUUGUCAGCAUCUGUAAAU | 31% | 70 | 5 | (4) | | | 8 3 | (6) (2) |
| #31 142 222 | 320 | 169 | GCUGACAAUACUUGGGAAC GUUCCCAAGUAUUGUCAGC | 47% | 77 | 5 | (4) | 2 | (1) | 5 | (4) |
| #32 143 223 | 322 | 171 | UGACAAUACUUGGGAACCU AGGUUCCCAAGUAUUGUCA | 42% | 68 | 5 | (4) | 2 | (2) | 5 | (3) |
| #33 55 224 | 330 | 179 | CUUGGGAACCUGAAGAAAA UUUUCUUCAGGUUCCCAAG | 42% | 102 | 5 | (4) | 2 | (2) | 7 | (5) |
| #34 144 225 | 331 | 180 | UUGGGAACCUGAAGAAAAU AUUUUCUUCAGGUUCCCAA | 36% | 81 | 5 | (4) | 3 | (3) | 10 | (8) |
| #35 56 226 | 360 | 209 | CAGAAUUGAUUGAAGCGUU AACGCUUCAAUCAAUUCUG | 36% | 100 | 3 | (2) | 2 | (2) | | |
| #36 57 227 | 361 | 210 | AGAAUUGAUUGAAGCGUUU AAACGCUUCAAUCAAUUCU | 31% | 99 | 3 | (2) | 2 | (2) | | |
| #37 145 228 | 366 | 215 | UGAUUGAAGCGUUUCUUAA UUAAGAAACGCUUCAAUCA | 31% | 67 | 3 | (2) | | | 4 | (4) |

TABLE 2C

| SEQ ID NO: | Position gene | CDS | Candidate sequence | GC % | Score | Position 19/19 | | 18/19 | | 17/19 | |
|---|---|---|---|---|---|---|---|---|---|---|---|
| #38 146 229 | 376 | 225 | GUUUCUUAACUCUCAGAAA UUUCUGAGAGUUAAGAAAC | 31% | 65 | 3 | (2) | | | 6 | (5) |
| #39 58 230 | 388 | 237 | UCAGAAAGCUGGCAAAGAA UUCUUUGCCAGCUUUCUGA | 42% | 114 | 3 | (2) | 4 | (3) | 2 3 | (2) (3) |
| #40 59 231 | 389 | 238 | CAGAAAGCUGGCAAAGAAA UUUCUUUGCCAGCUUUCUG | 42% | 106 | 3 | (2) | 4 | (3) | 7 5 | (5) (5) |
| #41 147 232 | 390 | 239 | AGAAAGCUGGCAAAGAAAA UUUUCUUUGCCAGCUUUCU | 36% | 78 | 3 | (2) | 5 | (4) | 9 3 | (7) (3) |
| #42 60 233 | 391 | 240 | GAAAGCUGGCAAAGAAAAA UUUUUCUUUGCCAGCUUUC | 36% | 104 | 3 | (2) | 4 | (3) | 10 4 | (7) (4) |
| #43 148 234 | 397 | 246 | UGGCAAAGAAAAAGAUGGU ACCAUCUUUUUCUUUGCCA | 36% | 71 | 3 | (2) | 4 | (3) | 2 4 | (2) (3) |
| #44 61 235 | 399 | 248 | GCAAAGAAAAAGAUGGUAC GUACCAUCUUUUUCUUUGC | 36% | 107 | 3 | (2) | 2 | (1) | 3 2 | (3) (2) |
| #45 62 236 | 400 | 249 | CAAAGAAAAAGAUGGUACA UGUACCAUCUUUUUCUUUG | 31% | 100 | 3 | (2) | 2 | (1) | 4 | (4) |
| #46 149 237 | 426 | 275 | AAUCUUUAUCUGACAGUGA UCACUGUCAGAUAAAGAUU | 31% | 58 | 7 | (6) | 2 | (1) | 3 | (2) |
| #47 63 238 | 441 | 290 | GUGAAUCUGAUGACAGCAA UUGCUGUCAUCAGAUUCAC | 42% | 87 | 7 | (5) | 4 | (3) | 5 1 | (4) (1) |
| #48 150 239 | 443 | 292 | GAAUCUGAUGACAGCAAAU AUUUGCUGUCAUCAGAUUC | 36% | 66 | 7 | (5) | 3 | (3) | 3 | (2) |
| #49 151 240 | 449 | 298 | GAUGACAGCAAAUCAAAGA UCUUUGAUUUGCUGUCAUC | 36% | 63 | 5 | (4) | 2 | (2) | 8 4 | (5) (3) |

TABLE 2C-continued

| SEQ ID NO: | Position gene | CDS | Candidate sequence | GC % | Score | Position 19/19 | | 18/19 | | 17/19 | |
|---|---|---|---|---|---|---|---|---|---|---|---|
| #50 241 | 152 | 452 | 301 GACAGCAAAUCAAAGAAGA UCUUCUUUGAUUUGCUGUC | 36% | 64 | 5 | (4) | 3 | (3) | 4 5 | (3) (2) |
| #51 242 | 64 | 453 | 302 ACAGCAAAUCAAAGAAGAA UUCUUCUUUGAUUUGCUGU | 31% | 89 | 5 | (4) | 1 | (1) | 15 6 | (11) (3) |
| #52 243 | 153 | 454 | 303 CAGCAAAUCAAAGAAGAAA UUUCUUCUUUGAUUUGCUG | 31% | 89 | 5 | (4) | 1 | (1) | 18 4 | (13) (2) |
| #53 244 | 154 | 456 | 305 GCAAAUCAAAGAAGAAAAG CUUUUCUUCUUUGAUUUGC | 31% | 72 | 3 | (2) | 2 | (2) | 27 1 | (19) (1) |
| #54 245 | 66 | 461 | 310 UCAAAGAAGAAAAGAGAUG CAUCUCUUUUCUUCUUUGA | 31% | 94 | 3 | (2) | 2 2 | (2) (1) | 8 5 | (7) (4) |
| #55 246 | 155 | 466 | 315 GAAGAAAAGAGAUGCUGCU AGCAGCAUCUCUUUUCUUC | 42% | 72 | 3 | (2) | 5 | (4) | 15 4 | (9) (4) |
| #56 247 | 156 | 468 | 317 AGAAAAGAGAUGCUGCUGA UCAGCAGCAUCUCUUUUCU | 42% | 82 | 5 1 | (3) (1) | 2 | (2) | 8 2 | (7) (2) |

TABLE 2D

| SEQ ID NO: | Position gene | CDS | Candidate sequence | GC % | Score | Position 19/19 | | 18/19 | | 17/19 | |
|---|---|---|---|---|---|---|---|---|---|---|---|
| #57 248 | 67 | 469 | 318 GAAAAGAGAUGCUGCUGAC GUCAGCAGCAUCUCUUUUC | 47% | 89 | 5 | (3) | 2 1 | (2) (1) | 3 2 | (3) (2) |
| #58 249 | 157 | 471 | 320 AAAGAGAUGCUGCUGACAA UUGUCAGCAGCAUCUCUUU | 42% | 75 | 5 | (3) | 2 | (2) | 7 1 | (6) (1) |
| #59 250 | 68 | 472 | 321 AAGAGAUGCUGCUGACAAA UUUGUCAGCAGCAUCUCUU | 42% | 112 | 5 | (3) | 4 | (4) | 7 5 | (5) (4) |
| #60 251 | 69 | 482 | 331 GCUGACAAACCAAGAGGAU AUCCUCUUGGUUUGUCAGC | 47% | 91 | 5 | (4) | 2 2 | (1) (1) | 4 | (2) |
| #61 252 | 158 | 483 | 332 CUGACAAACCAAGAGGAUU AAUCCUCUUGGUUUGUCAG | 42% | 61 | 5 | (4) | 2 | (1) | 2 2 | (1) (1) |
| #62 253 | 1 | 484 | 333 UGACAAACCAAGAGGAUUU AAAUCCUCUUGGUUUGUCA | 36% | 132 | 5 | (4) | | | 6 | (5) |
| #63 254 | 159 | 490 | 339 ACCAAGAGGAUUUGCCAGA UCUGGCAAAUCCUCUUGGU | 47% | 78 | 5 | (4) | | | 4 1 | (3) (1) |
| #64 255 | 160 | 496 | 345 AGGAUUUGCCAGAGGUCUU AAGACCUCUGGCAAAUCCU | 47% | 85 | 5 | (4) | | | 3 1 | (3) (1) |
| #65 256 | 161 | 502 | 351 UGCCAGAGGUCUUGAUCCU AGGAUCAAGACCUCUGGCA | 52% | 65 | 5 | (4) | 2 | (2) | 3 6 | (2) (2) |
| #66 257 | 162 | 504 | 353 CCAGAGGUCUUGAUCCUGA UCAGGAUCAAGACCUCUGG | 52% | 76 | 5 | (4) | 2 | (2) | 4 1 | (3) (1) |
| #67 258 | 163 | 508 | 357 AGGUCUUGAUCCUGAAAGA UCUUUCAGGAUCAAGACCU | 42% | 79 | 5 | (4) | | | 4 1 | (3) (1) |
| #68 259 | 164 | 510 | 359 GUCUUGAUCCUGAAAGAAU AUUCUUUCAGGAUCAAGAC | 36% | 60 | 5 | (4) | 1 | (1) | 2 | (2) |
| #69 260 | 165 | 511 | 360 UCUUGAUCCUGAAAGAAUA UAUUCUUUCAGGAUCAAGA | 31% | 81 | 5 | (4) | | | 5 3 | (5) (2) |
| #70 261 | 166 | 537 | 386 CCACAGACAGCAGUGGAGA UCUCCACUGCUGUCUGUGG | 57% | 63 | 7 | (6) | | | 6 7 | (4) (6) |
| #71 262 | 167 | 538 | 387 CACAGACAGCAGUGGAGAA UUCUCCACUGCUGUCUGUG | 52% | 76 | 7 | (6) | | | 11 4 | (7) (3) |

TABLE 2D-continued

| SEQ ID NO: | Position gene | CDS | Candidate sequence | GC % | Score | 19/19 | | 18/19 | | 17/19 | |
|---|---|---|---|---|---|---|---|---|---|---|---|
| #72 263 | 168 | 539 | 388 ACAGACAGCAGUGGAGAAU AUUCUCCACUGCUGUCUGU | 47% | 63 | 5 | (4) | 2 | (2) | 3 1 | (2) (1) |
| #73 264 | 70 | 541 | 390 AGACAGCAGUGGAGAAUUG CAAUUCUCCACUGCUGUCU | 47% | 86 | 5 | (4) | 2 | (2) | 1 | (1) |
| #74 265 | 169 | 549 | 398 GUGGAGAAUUGAUGUUUCU AGAAACAUCAAUUCUCCAC | 36% | 57 | 5 | (4) | | | 4 | (3) |
| #75 266 | 170 | 552 | 401 GAGAAUUGAUGUUUCUCAU AUGAGAAACAUCAAUUCUC | 31% | 75 | 5 | (4) | | | 2 | (2) |

TABLE 2E

| SEQ ID NO: | Position gene | CDS | Candidate sequence | GC % | Score | 19/19 | | 18/19 | | 17/19 | |
|---|---|---|---|---|---|---|---|---|---|---|---|
| #76 267 | 171 | 554 | 403 GAAUUGAUGUUUCUCAUGA UCAUGAGAAACAUCAAUUC | 31% | 60 | 5 | (4) | | | 2 1 | (2) (1) |
| #77 268 | 71 | 566 | 415 CUCAUGAAAUGGAAAGAUU AAUCUUUCCAUUUCAUGAG | 31% | 83 | 5 | (4) | 2 | (2) | 3 | (2) |
| #78 269 | 172 | 568 | 417 CAUGAAAUGGAAAGAUUCA UGAAUCUUUCCAUUUCAUG | 31% | 74 | 5 | (4) | 2 | (2) | 1 | (1) |
| #79 270 | 173 | 570 | 419 UGAAAUGGAAAGAUUCAGA UCUGAAUCUUUCCAUUUCA | 31% | 64 | 5 | (4) | 2 | (2) | 7 1 | (5) (1) |
| #80 271 | 174 | 576 | 425 GGAAAGAUUCAGAUGAGGC GCCUCAUCUGAAUCUUUCC | 47% | 60 | 5 | (4) | | | 4 2 | (3) (1) |
| #81 272 | 175 | 577 | 426 GAAAGAUUCAGAUGAGGCA UGCCUCAUCUGAAUCUUUC | 42% | 80 | 5 | (4) | | | 3 2 | (3) (1) |
| #82 273 | 176 | 579 | 428 AAGAUUCAGAUGAGGCAGA UCUGCCUCAUCUGAAUCUU | 42% | 71 | 5 | (4) | 1 | (1) | 7 | (5) |
| #83 274 | 72 | 594 | 443 CAGACUUGGUGCUGGCGAA UUCGCCAGCACCAAGUCUG | 57% | 107 | 3 | (2) | 5 | (3) | 2 | (1) |
| #84 275 | 177 | 595 | 444 AGACUUGGUGCUGGCGAAA UUUCGCCAGCACCAAGUCU | 52% | 67 | 3 | (2) | 2 | (2) | 4 | (2) |
| #85 276 | 178 | 597 | 446 ACUUGGUGCUGGCGAAAGA UCUUUCGCCAGCACCAAGU | 52% | 80 | 3 | (2) | 2 | (2) | | |
| #86 277 | 179 | 601 | 450 GGUGCUGGCGAAAGAGGCA UGCCUCUUUCGCCAGCACC | 63% | 70 | 3 | (2) | | | 13 1 | (10) (1) |
| #87 278 | 180 | 606 | 455 UGGCGAAAGAGGCAAAUAU AUAUUUGCCUCUUUCGCCA | 42% | 73 | 3 | (2) | 2 | (2) | 1 | (1) |
| #88 279 | 73 | 608 | 457 GCGAAAGAGGCAAAUAUGA UCAUAUUUGCCUCUUUCGC | 42% | 86 | 3 | (2) | 2 | (2) | | |
| #89 280 | 74 | 609 | 458 CGAAAGAGGCAAAUAUGAA UUCAUAUUUGCCUCUUUCG | 36% | 117 | 3 | (2) | 2 | (2) | 2 2 | (1) (2) |
| #90 281 | 181 | 615 | 464 AGGCAAAUAUGAAGUGUCC GGACACUUCAUAUUUGCCU | 42% | 66 | 3 | (2) | 2 | (2) | 3 | (3) |
| #91 282 | 182 | 617 | 466 GCAAAUAUGAAGUGUCCUC GAGGACACUUCAUAUUUGC | 42% | 73 | 3 | (2) | 4 | (4) | 2 | (1) |
| #92 283 | 183 | 620 | 469 AAUAUGAAGUGUCCUCAAA UUUGAGGACACUUCAUAUU | 31% | 65 | 3 | (2) | 4 | (4) | 2 | (1) |
| #93 284 | 184 | 632 | 481 CCUCAAAUUGUAAUUGCUU AAGCAAUUACAAUUUGAGG | 31% | 57 | 5 | (4) | 4 | (3) | 3 | (2) |

TABLE 2E-continued

| SEQ ID NO: | Position gene | CDS | Candidate sequence | GC % | Score | Position 19/19 | | 18/19 | | 17/19 | |
|---|---|---|---|---|---|---|---|---|---|---|---|
| #94 185 285 | 658 | 507 | AGAGAGACUAACUUGGCAU AUGCCAAGUUAGUCUCUCU | 42% | 61 | 7 | (5) | 2 | (2) | 1 1 | (1) (1) |

TABLE 2F

| SEQ ID NO: | Position gene | CDS | Candidate sequence | GC % | Score | Position 19/19 | | 18/19 | | 17/19 | |
|---|---|---|---|---|---|---|---|---|---|---|---|
| #95 186 286 | 659 | 508 | GAGAGACUAACUUGGCAUU AAUGCCAAGUUAGUCUCUC | 42% | 60 | 7 | (5) | 2 | (2) | 1 | (1) |
| #96 187 287 | 673 | 522 | GCAUUCUUGUCCAGAAGAU AUCUUCUGGACAAGAAUGC | 42% | 61 | 7 | (6) | | | 3 3 | (2) (2) |
| #97 188 288 | 681 | 530 | GUCCAGAAGAUGAAGCUCA UGAGCUUCAUCUUCUGGAC | 47% | 82 | 5 | (4) | 2 | (2) | 4 | (3) |
| #98 189 289 | 682 | 531 | UCCAGAAGAUGAAGCUCAA UUGAGCUUCAUCUUCUGGA | 42% | 80 | 5 | (4) | | | 10 | (7) |
| #99 75 290 | 684 | 533 | CAGAAGAUGAAGCUCAAUA UAUUGAGCUUCAUCUUCUG | 36% | 91 | 5 | (4) | | | 4 | (4) |
| #100 190 291 | 685 | 534 | AGAAGAUGAAGCUCAAUAA UUAUUGAGCUUCAUCUUCU | 31% | 75 | 5 | (4) | | | 7 1 | (6) (1) |
| #101 83 292 | 1220 | | GAUAAUCCCUUCAAGUUAA UUAACUUGAAGGGAUUAUC | 31% | 95 | 3 | (2) | | | 11 | (7) |
| #102 84 293 | 1258 | | CCAUACAUUUCAAGUGAAA UUUCACUUGAAAUGUAUGG | 31% | 118 | 3 | (2) | | | 2 | (1) |
| #103 88 294 | 1417 | | GACAAAUGCUAGUGUGUUU AAACACACUAGCAUUUGUC | 36% | 112 | 3 | (2) | | | | |
| #104 89 295 | 1487 | | GGGCCAUUCCUUAGCAAAA UUUUGCUAAGGAAUGGCCC | 47% | 114 | 3 | (2) | | | 1 | (1) |
| #105 191 296 | 1538 | | GGUCAUGAUGAAUGGAAUA UAUUCCAUUCAUCAUGACC | 36% | 124 | 3 | (2) | | | 1 1 | (1) (1) |
| #106 95 297 | 1730 | | CAGCAAAAGCCAGGAAGAA UUCUUCCUGGCUUUUGCUG | 47% | 110 | 3 | (2) | | | 2 | (2) |

Furthermore, among the 19-base RNA listed above in Tables 2A to 2F, those which are particularly preferred both from the viewpoint of their high RNAi effect and high HP1γ specificity are the following eleven siRNAs: #5 (sense sequence No. 41, antisense sequence No. 196), #17 (sense sequence No. 49, antisense sequence No. 208), #35 (sense sequence No. 56, antisense sequence No. 226), #62 (sense sequence No. 1, antisense sequence No. 253), #89 (sense sequence No. 74, antisense sequence No. 280), #101 (sense sequence No. 83, antisense sequence No. 292), #102 (sense sequence No. 84, antisense sequence No. 293), #103 (sense sequence No. 88, antisense sequence No. 294), #104 (sense sequence No. 89, antisense sequence No. 295), #105 (sense sequence No. 191, antisense sequence No. 296), and #106 (sense sequence No. 95, antisense sequence No. 297).

Namely, siRNAs based on the eleven double-stranded RNA portions presented above are highly specific to HP1γ mRNA, as is seen in the following Tables 3A to 3K, which presents the result of a search of genes which include sequences that are either fully identical to (19/19), differ only in one base (18/19) from, or differ in two bases (17/19) from them, and they therefore are particularly unlikely to cause any off-target effect. One may use either any one of these siRNA alone or two or more of them concomitantly (e.g., in a mixture, or through simultaneous administration of them). Among these eleven, those having particularly great specificity to HP1γ mRNA are those based on #17 (sense sequence No. 49, antisense sequence No. 208), #62 (sense sequence No. 1, antisense sequence 253), or #89 (sense sequence No. 74, anti sense sequence No. 280), which are most preferred.

In Tables 3A to 3K, "Accession#" indicates Accession numbers of the sequences in GenBank, and under "NM_016587", which is the accession number of human HP1γ, are listed accession numbers of matching sequences that were hit in the search. "GeneID#" indicates identification numbers assigned to the genes, and "11335" in the Tables indicates human HP1γ gene itself. "Predicted" means that the indicated gene is hypothetical one which is predicted on computer. Further, "CBX3" and "chromosome homolog 3 (HP1 gamma homolog, *Drosophila*)" are the official code and the official name, respectively, assigned to HP1γ by NCBI.

TABLE 3A

| | Match | Sequence | Accession# | SEQ ID NO: | gene | CDS | GeneID# | Definition |
|---|---|---|---|---|---|---|---|---|
| #5 | 19/19 | Sense | NM_016587 | 41 | 194 | 43 | | |
| | | | XR_015260.1 | | 322 | 3U | 730552 | PREDICTED: *Homo sapiens* similar to chromobox homolog 3 (LOC730552), mRNA. |
| | | | XM_938779.2 | | 155 | CDS | 653972 | PREDICTED: *Homo sapiens* similar to chromobox homolog 3 (LOC653972), mRNA. |
| | | | NM_007276.3 | | 154 | CDS | 11335 | *Homo sapiens* chromobox homolog 3 (HP1 gamma homolog, *Drosophila*) (CBX3), transcript variant 1, mRNA. |
| | | | XR_015356.1 | | 322 | 3U | 728217 | PREDICTED: *Homo sapiens* similar to chromobox homolog 3 (LOC728217), mRNA. |
| | | | NM_016587.2 | | 194 | CDS | 11335 | *Homo sapiens* chromobox homolog 3 (HP1 gamma homolog, *Drosophila*) (CBX3), transcript variant 1, mRNA. |
| | 18/19 | | NM_016587 | 41 | 194 | 43 | | |
| | 17/19 | | NM_016587 | 41 | 194 | 43 | | |
| | | | NR_002723.2 | | 173365 | 3U | 8327 | *Homo sapiens* GA binding protein transcription factor, alpha subunit pseudogene (GABPAP) on chromosome 7. |
| | | | XR_019241.1 | | 45 | 3U | 651211 | PREDICTED: *Homo sapiens* similar to chromobox homolog 3 (LOC651211), mRNA. |
| | | | NM_006694.2 | | 1309 | 3U | 10899 | *Homo sapiens* jumping translocation breakpoint (JTB), mRNA. |
| | | | NM_033106.2 | | 905 | 3U | 85569 | *Homo sapiens* galanin-like peptide precursor (GALP), mRNA. |
| | | | XR_016921.1 | | 45 | 3U | 644101 | PREDICTED: *Homo sapiens* similar to chromobox homolog 3 (LOC644101), mRNA. |
| | | | NM_001018116.1 | | 1832 | 3U | 347273 | *Homo sapiens* similar to RIKEN cDNA 2310039E09 (LOC347273), mRNA. |
| | 19/19 | Antisense | NM_016587 | 196 | 194 | 43 | | |
| | 18/19 | | NM_016587 | 196 | 194 | 43 | | |
| | 17/19 | | NM_016587 | 196 | 194 | 43 | | |

TABLE 3B

| | Match | Sequence | Accession# | SEQ ID NO: | gene | CDS | GeneID# | Definition |
|---|---|---|---|---|---|---|---|---|
| #17 | 19/19 | Sense | NM_016587 | 49 | 247 | 96 | | |
| | | | XM_938779.2 | | 208 | CDS | 653972 | PREDICTED: *Homo sapiens* similar to chromobox homolog 3 (LOC653972), mRNA. |
| | | | NM_007276.3 | | 207 | CDS | 11335 | *Homo sapiens* chromobox homolog 3 (HP1 gamma homolog, *Drosophila*) (CBX3), transcript variant 1, mRNA. |
| | | | NM_016587.2 | | 247 | CDS | 11335 | *Homo sapiens* chromobox homolog 3 (HP1 gamma homolog, *Drosophila*) (CBX3), transcript variant 1, mRNA. |
| | 18/19 | | NM_016587 | 49 | 247 | 96 | | |
| | | | XR_019241.1 | | 97 | 3U | 651211 | PREDICTED: *Homo sapiens* similar to chromobox homolog 3 (LOC651211), mRNA. |
| | | | XR_016921.1 | | 97 | 3U | 644101 | PREDICTED: *Homo sapiens* similar to chromobox homolog 3 (LOC644101), mRNA. |
| | 17/19 | | NM_016587 | 49 | 247 | 96 | | |
| | | | NM_001040455.1 | | 1369 | CDS | 51092 | *Homo sapiens* SID1 transmembrane family, member 2 (SIDT2), mRNA. |
| | 19/19 | Antisense | NM_016587 | 208 | 247 | 96 | | |
| | 18/19 | | NM_016587 | 208 | 247 | 96 | | |
| | 17/19 | | NM_016587 | 208 | 247 | 96 | | |

TABLE 3C

| | Match | Sequence | Accession# | SEQ ID NO: | gene | CDS | GeneID# | Definition |
|---|---|---|---|---|---|---|---|---|
| #35 | 19/19 | Sense | NM_016587 | 56 | 360 | 209 | | |
| | | | XM_938779.2 | | 321 | CDS | 653972 | PREDICTED: *Homo sapiens* similar to chromobox homolog 3 (LOC653972), mRNA. |
| | | | NM_007276.3 | | 320 | CDS | 11335 | *Homo sapiens* chromobox homolog 3 (HP1 gamma homolog, *Drosophila*) (CBX3), transcript variant 1, mRNA. |
| | | | NM_016587.2 | | 360 | CDS | 11335 | *Homo sapiens* chromobox homolog 3 (HP1 gamma homolog, *Drosophila*) (CBX3), transcript variant 1, mRNA. |
| | 18/19 | | NM_016587 | 56 | 360 | 209 | | |
| | | | XR_019241.1 | | 210 | 3U | 651211 | PREDICTED: *Homo sapiens* similar to chromobox homolog 3 (LOC651211), mRNA. |
| | | | XR_016921.1 | | 210 | 3U | 644101 | PREDICTED: *Homo sapiens* similar to chromobox homolog 3 (LOC644101), mRNA. |
| | 17/19 | | NM_016587 | 56 | 360 | 209 | | |
| | 19/19 | Antisense | NM_016587 | 226 | 360 | 209 | | |
| | 18/19 | | NM_016587 | 226 | 360 | 209 | | |
| | 17/19 | | NM_016587 | 226 | 360 | 209 | | |

TABLE 3D

| | Match | Sequence | Accession# | SEQ ID NO: | gene | CDS | GeneID# | Definition |
|---|---|---|---|---|---|---|---|---|
| #62 | 19/19 | Sense | NM_016857 | 1 | 484 | 333 | | |
| | | | XM_938779.2 | | 445 | CDS | 653972 | PREDICTED: *Homo sapiens* similar to chromobox homolog 3 (LOC653972), mRNA. |
| | | | XR_019241.1 | | 333 | 3U | 651211 | PREDICTED: *Homo sapiens* similar to chromobox homolog 3 (LOC651211), mRNA. |
| | | | NM_007276.3 | | 444 | CDS | 11335 | *Homo sapiens* chromobox homolog 3 (HP1 gamma homolog, *Drosophila*) (CBX3), transcript variant 1, mRNA. |
| | | | XR_016921.1 | | 333 | 3U | 644101 | PREDICTED: *Homo sapiens* similar to chromobox homolog 3 (LOC644101), mRNA. |
| | | | NM_016587.2 | | 484 | CDS | 11335 | *Homo sapiens* chromobox homolog 3 (HP1 gamma homolog, *Drosophila*) (CBX3), transcript variant 2, mRNA. |
| | 18/19 | | NM_016587 | 1 | 484 | 333 | | |
| | 17/19 | | NM_016587 | 1 | 484 | 333 | | |
| | | | NM_014753.2 | | 844 | COS | 9790 | *Homo sapiens* BMS1 homolog, ribosome assembly protein (yeast) (BMS1), mRNA. |
| | | | XM_001126283.1 | | 264 | CDS | | PREDICTED: *Homo sapiens* similar to chromobox homolog 3 (LOC642721), mRNA. |
| | | | XR_015804.1 | | 887 | 3U | 729096 | PREDICTED: *Homo sapiens* similar to BMS1-like, ribosome assembly protein (LOC729096), mRNA. |
| | | | XM_01128446.1 | | 273 | CDS | 642721 | PREDICTED; *Homo sapiens* similar to chromobox homolog 3 (LOC642721), mRNA. |
| | | | NM_147128.3 | | 1827 | 3U | | *Homo sapiens* zinc and ring finger 2 (ZNRF2), mRNA, |
| | | | XM_944657.2 | | 996 | CDS | 653468 | PREDICTED: *Homo sapiens* hypothetical protein LOC653468, transcript variant 3(LOC653468), mRNA. |
| | 19/19 | Antisense | NM_016587 | 253 | 484 | 333 | | |
| | 18/19 | | NM_016587 | 253 | 484 | 333 | | |
| | 17/19 | | NM_016587 | 253 | 484 | 333 | | |

TABLE 3E

| | Match | Sequence | Accession# | SEQ ID NO: | gene | CDS | GeneID# | Definition |
|---|---|---|---|---|---|---|---|---|
| #89 | 19/19 | Sense | NM_016587 | | 609 | 458 | | |
| | | | XM_938779.2 | | 570 | CDS | 653972 | PREDICTED: *Homo sapiens* similar to chromobox homolog 3 (LOC653972), mRNA. |
| | | | NM_007276.3 | | 569 | CDS | 11335 | *Homo sapiens* chromobox homolog 3 (HP1 gamma homolog, *Drosophila*) (CBX3), transcript variant 1, mRNA. |
| | | | NM_016587.2 | | 609 | CDS | 11335 | *Homo sapiens* chromobox homolog 3 (HP1 gamma homolog, *Drosophila*) (CBX3), transcript variant 2, mRNA. |
| | 18/19 | | NM_016587 | 74 | 609 | 458 | | |
| | | | XR_015260.1 | | 737 | 3U | 730552 | PREDICTED: *Homo sapiens* similar to chromobox homolog 3 (LOC730552), mRNA. |
| | | | XR_015356.1 | | 737 | 3U | 728217 | PREDICTED: *Homo sapiens* similar to chromobox homolog 3 (LOC728217), mRNA. |
| | 17/19 | | NM_016587 | 74 | 609 | 458 | | |
| | | | NM_001077186.1 | | 3046 | CDS | 79784 | *Homo sapiens* myosin, heavy chain 14 (MYH14), transcript variant 1, mRNA. |
| | | | NM_024729.3 | | 3022 | CDS | 79784 | *Homo sapiens* myosin, heavy chain 14 (MYH14), transcript variant 2, mRNA. |
| | 19/19 | Antisense | NM_016587 | 280 | 609 | 458 | | |
| | 18/19 | | NM_016587 | 280 | 609 | 458 | | |
| | 17/19 | | NM_016587 | 280 | 609 | 458 | | |
| | | | NM_016150.3 | | 242 | 5U | 51676 | *Homo sapiens* ankyrin repeat and SOCS box-containing 2 (ASB2), mRNA. |
| | | | NM_199324.1 | | 6202 | 3U | 54726 | *Homo sapiens* OTU domain containing 4 (OTUD4), transcript variant 1, mRNA. |

TABLE 4F

| | Match | Sequence | Accession# | SEQ ID NO: | gene | CDS | GeneID# | Definition |
|---|---|---|---|---|---|---|---|---|
| #101 | 19/19 | Sense | NM_016587 | 83 | 1220 | | | |
| | | | XM_938779.2 | | 1177 | 3U | 653972 | PREDICTED: *Homo sapiens* similar to chromobox homolog 3 (LOC653972), mRNA. |
| | | | NM_007276.3 | | 1180 | 3U | 11335 | *Homo sapiens* chromobox homolog 3 (HP1 gamma homolog, *Drosophila*) (CBX3), transcript variant 1, mRNA. |
| | | | NM_016587.2 | | 1220 | 3U | 11335 | *Homo sapiens* chromobox homolog 3 (HP1 gamma homolog, *Drosophila*) (CBX3), transcript variant 2, mRNA. |
| | 18/19 | | NM_016587 | 83 | 1220 | | | |
| | 17/19 | | NM_016587 | 83 | 1220 | | | |
| | 19/19 | Antisense | NM_016587 | 292 | 1220 | | | |
| | 18/19 | | NM_016587 | 292 | 1220 | | | |
| | 17/19 | | NM_016587 | 292 | 1220 | | | |

TABLE 3G

| | Match | Sequence | Accession# | SEQ ID NO: | gene | CDS | GeneID# | Definition |
|---|---|---|---|---|---|---|---|---|
| #102 | 19/19 | Sense | NM_016587 | 84 | 1258 | | | |
| | | | XM_938779.2 | | 1215 | 3U | 653972 | PREDICTED: *Homo sapiens* similar to chromobox homolog 3 (LOC653972), mRNA. |
| | | | NM_007276.3 | | 1218 | 3U | 11335 | *Homo sapiens* chromobox homolog 3 (HP1 gamma homolog, *Drosophila*) (CBX3), transcript variant 1, mRNA. |

TABLE 3G-continued

| Match | Sequence | Accession# | SEQ ID NO: | gene | CDS | GeneID# | Definition |
|---|---|---|---|---|---|---|---|
| | | NM_016587.2 | | 1258 | 3U | 11335 | Homo sapiens chromobox homolog 3 (HP1 gamma homolog, Drosophila) (CBX3), transcript variant 2, mRNA. |
| 18/19 | | NM_016587 | 84 | 1258 | | | |
| 17/19 | | NM_016587 | 84 | 1258 | | | |
| | | NM_003187.4 | | 1150 | 3U | | Homo sapiens TAF9 RNA polymerase II, TATA box binding protein (TBP)-associated factor, 32 kDa (TAF9), transcript variant 1, mRNA. |
| | | MM_001015892.1 | | 1387 | 3U | 6880 | Homo sapiens TAF9 RNA polymerase II, TATA box binding protein (TBP)-associated factor, 32 kDa (TAF9), transcript variant 4, mRNA. |
| 19/19 | Antisense | NM_016587 | 293 | 1258 | | | |
| 18/19 | | NM_016587 | 293 | 1258 | | | |
| 17/19 | | NM_016587 | 293 | 1258 | | | |

TABLE 3H

| | Match | Sequence | Accession# | SEQ ID NO: | gene | CDS | GeneID# | Definition |
|---|---|---|---|---|---|---|---|---|
| #103 | 19/19 | Sense | NM_016587 | 88 | 1417 | | | |
| | | | XM_938779.2 | | 1374 | 3U | 653972 | PREDICTED: Homo sapiens similar to chromobox homolog 3 (LOC653972), mRNA. |
| | | | NM_007276.3 | | 1377 | 3U | 11335 | Homo sapiens chromobox homolog 3 (HP1 gamma homolog, Drosophila) (CBX3), transcript variant 1, mRNA. |
| | | | NM_016587.2 | | 1417 | 3U | 11335 | Homo sapiens chromobox homolog 3 (HP1 gamma homolog, Drosophila) (CBX3), transcript variant 3, mRNA. |
| | 18/19 | | NM_016587 | 88 | 1417 | | | |
| | 17/19 | | NM_016587 | 88 | 1417 | | | |
| | 19/19 | Antisense | NM_016587 | 294 | 1417 | | | |
| | 18/19 | | NM_016587 | 294 | 1417 | | | |
| | 17/19 | | NM_016587 | 294 | 1417 | | | |

TABLE 3I

| | Match | Sequence | Accession# | SEQ ID NO: | gene | CDS | GeneID# | Definition |
|---|---|---|---|---|---|---|---|---|
| #104 | 19/19 | Sense | NM_016587 | 89 | 1487 | | | |
| | | | XM_938779.2 | | 1444 | 3U | 653972 | PREDICTED: Homo sapiens similar to chromobox homolog 3 (LOC653972), mRNA. |
| | | | NM_007276.3 | | 1447 | 3U | 11335 | Homo sapiens chromobox homolog 3 (HP1 gamma homolog, Drosophila) (CBX3), transcript variant 1, mRNA. |
| | | | NM_016587.2 | | 1487 | 3U | 11335 | Homo sapiens chromobox homolog 3 (HP1 gamma homolog, Drosophila) (CBX3), transcript variant 2, mRNA. |
| | 18/19 | | NM_016587 | 89 | 1487 | | | |
| | 17/19 | | NM_016587 | 89 | 1487 | | | |
| | 19/19 | Antisense | NM_016587 | 295 | 1487 | | | |
| | 18/19 | | NM_016587 | 295 | 1487 | | | |
| | 17/19 | | NM_016587 | 295 | 1487 | | | |
| | | | NM_004872.3 | | 1588 | 3U | 9528 | Homo sapiens transmembrane protein 59 (TMEM59), mRNA. |

TABLE 3J

| | Match | Sequence | Accession# | SEQ ID NO: | gene | CDS | GeneID# | Definition |
|---|---|---|---|---|---|---|---|---|
| #105 | 19/19 | Sense | NM_016587 | 191 | 1538 | | | |
| | | | XM_938779.2 | | 1495 | 3U | 653972 | PREDICTED: Homo sapiens similar to chromobox homolog 3 (LOC653972), mRNA. |

TABLE 3J-continued

| Match | Sequence | Accession# | SEQ ID NO: | gene | CDS | GeneID# | Definition |
|---|---|---|---|---|---|---|---|
| | | NM_007276.3 | | 1498 | 3U | 11335 | *Homo sapiens* chromobox homolog 3 (HP1 gamma homolog, *Drosophila*) (CBX3), transcript variant 1, mRNA. |
| | | NM_016587.2 | | 1538 | 3U | 11335 | *Homo sapiens* chromobox homolog 3 (HP1 gamma homolog, *Drosophila*) (CBX3), transcript variant 2, mRNA. |
| 18/19 | | NM_016587 | 191 | 1538 | | | |
| 17/19 | | NM_016587 | 191 | 1538 | | | |
| | | NM_153262.2 | | 1733 | CDS | 255928 | *Homo sapiens* synaptotagmin XIV (SYT14), mRNA. |
| 19/19 | Antisense | NM_016587 | 296 | 1538 | | | |
| 18/19 | | NM_016587 | 296 | 1538 | | | |
| 17/19 | | NM_016587 | 296 | 1538 | | | |
| | | NM_153810.4 | | 3335 | 3U | 143384 | *Homo sapiens* chromosome 10 open reading frame 46 (C10orf46), mRNA. |

TABLE 3K

| | Match | Sequence | Accession# | SEQ ID NO: | gene | CDS | GeneID# | Definition |
|---|---|---|---|---|---|---|---|---|
| #106 | 19/19 | Sense | NM_016587 | 95 | 1730 | | | |
| | | | XM_938779.2 | | 1687 | 3U | 653972 | PREDICTED: *Homo sapiens* similar to chromobox homolog 3 (LOC653972), mRNA. |
| | | | NM_007276.3 | | 1690 | 3U | 11335 | *Homo sapiens* chromobox homolog 3 (HP1 gamma homolog, *Drosophila*) (CBX3), transcript variant 1, mRNA. |
| | | | NM_016587.2 | | 1730 | 3U | 11335 | *Homo sapiens* chromobox homolog 3 (HP1 gamma homolog, *Drosophila*) (CBX3), transcript variant 2, mRNA. |
| | 18/19 | | NM_016587 | 95 | 1730 | | | |
| | 17/19 | | NM_016587 | 95 | 1730 | | | |
| | 19/19 | Antisense | NM_016587 | 297 | 1730 | | | |
| | 18/19 | | NM_016587 | 297 | 1730 | | | |
| | 17/19 | | NM_016587 | 297 | 1730 | | | |
| | | | NM_152292.3 | | 3155 | 3U | 93587 | *Homo sapiens* RNA (guanine-9-) methyltransferase domain containing 2 (RG9MTD2), mRNA. |
| | | | XR_018656.1 | | 451 | 3U | 649307 | PREDICTED: *Homo sapiens* similar to Olfactory receptor 10R2 (LOC649307), mRNA. |

There is no particular limitation as to how the above siRNAs are synthesized, and they thus may be synthesized either in vitro, chemically or enzymatically, or in vivo as well. It is preferred, however, that they are chemically synthesized by a method known in the art. Synthesized siRNAs are advantageous, because they, for example, allow easy adjustment of their concentration. They are also advantageous in respect of safety for they allow easy prevention of their contamination. For preparing an siRNA having overhangs and comprising the double-stranded sequences set forth as SEQ ID NO:1, for example, an RNA strand comprising the sequence set forth as SEQ ID NO:1 and having a 2-base overhang at the 3'-end thereof, and an RNA strand comprising the sequence that is complementary to the sequence set forth as SEQ ID NO:1 and having a 2-base overhang at the 3'-end thereof, are separately synthesized. Then the two RNA strands are allowed to form a pair to give a double-stranded siRNA with overhangs. Before use, as needed, they are preferably purified as desired by a method known in the art.

In the case where an antisense (single-stranded DNA) is used according to the present invention to suppress the expression of HP1γ gene, there is no particular limitation in choosing an antisense except than it has a nucleotide sequence which is complementary to the nucleotide sequence of HP1γ gene, and inhibits the expression of HP1γ gene. Such an antisense, as aforementioned, may inhibit either splicing into mRNA or translation into the HP1γ protein. There is no particular limitation as to the length of such antisenses, but it is preferably, for example, 10-40 mer, more preferably 17-30 mer, and still more preferably 20-30 mer in length. Examples of antisenses that may be employed according to the present invention are listed below.

TABLE 4

| Sequence | SEQ IQ NO: |
|---|---|
| 5' -CTGTTTTTTTCCCAT-3' | 98 |
| 5' -TCTGTTTTTTTCCCAT-3' | 99 |
| 5' -TTCTGTTTTTTTCCCAT-3' | 100 |

TABLE 4-continued

Table 4

| Sequence | SEQ ID NO: |
|---|---|
| 5'-ATTCTGTTTTTTCCCAT-3' | 101 |
| 5'-CATTCTGTTTTTTCCCAT-3' | 102 |
| 5'-CCATTCTGTTTTTTCCCAT-3' | 103 |
| 5'-TCCATTCTGTTTTTTCCCAT-3' | 104 |
| 5'-TCCATTCTGTTTTTTCCCAT-3' | 105 |
| 5'-TTCCATTCTGTTTTTTCCCAT-3' | 106 |
| 5'-TTTCCATTCTGTTTTTTCCCAT-3' | 107 |
| 5'-CTTTCCATTCTGTTTTTTCCCAT-3' | 108 |
| 5'-TCTTTCCATTCTGTTTTTTCCCAT-3' | 109 |
| 5'-CTCTTTCCATTCTGTTTTTTCCCAT-3' | 110 |
| 5'-ACTCTTTCCATTCTGTTTTTTCCCAT-3' | 111 |
| 5'-TACTCTTTCCATTCTGTTTTTTCCCAT-3' | 112 |
| 5'-TTACTCTTTCCATTCTGTTTTTTCCCAT-3' | 113 |

Since the cancer cell proliferation inhibitors, especially the siRNAs according to the present invention act to potently inhibit occurrence of "loss of differentiation", which is common to a variety of cancer cells, the types of cancers which are to be treated with them are not limited, but a wide variety of cancers, as aforementioned, may be treated, regardless of whether they are epithelial or non-epithelial cancers, or whether they are solid or non-solid cancers. Further, the cancer cell proliferation inhibitors according to the present invention can be used for the treatment of cancers in mammalian animals including human, and, among others, of human cancers. Cancer cells whose proliferation can be inhibited are not limited but are the same as the aforementioned cancer cells that can be identified with the method according to the present invention.

<Composition for Cancer Treatment>

The compositions for cancer treatment according to the present invention are medicinal compositions for the treatment of cancer, and comprises one of the aforementioned cancer cell proliferation inhibitors according to the present invention, inter alia, siRNAs specific to HP1γ in a pharmaceutically acceptable carrier well known in the art. Such a medicinal composition administered to a patient can inhibit proliferation of cancer cells and thereby potently suppress the progression of cancer. There is no specific limitation as to the types of cancers which may be treated, but they are the same as the aforementioned cancer cells that can be identified by the method according to the present invention. Furthermore, because the cancer cell proliferation inhibitors according to the present invention, inter alia siRNAs specific to HP1γ, are highly specific to cancer cells compared with other conventional agents which so far have been available, they enable either to minimize or eliminate the probability of affecting normal cells (non-cancerous cells), thereby remarkably reduce any risks of side effects.

The medicinal composition according to the present invention may further contain one or more cell differentiation-inducing agents. Addition of differentiation inducing agents enables, for example, to further promote the differentiation of the cancer cells and to effectively induce their apoptosis while suppressing proliferation of cancer cells with the aforementioned proliferation inhibitor agents. As cell differentiation-inducing agents mentioned above, those which are known in the art may be employed without particular limitation, and examples of them include, for example, adipose differentiation inducers such as thiazolidine derivatives (PPARγ-ligands) and the like. In addition, one or more anticancer drugs known in the art may also be contained, for they can further suppress proliferation of cancer cells and promote cell death. They include, for example, taxol, cisplatin, herceptin, 5-FU, glivec, rituxan, iressa, etc.

The medicinal composition according to the present invention may further contain a pharmaceutically acceptable carrier. Examples of such pharmaceutical carriers include, but not limited to, those carriers which can enhance the efficiency of penetration of the aforementioned expression inhibitors into target sites, tissues or cells (such as liposome, cation liposome, etc.). Examples of pharmaceutical forms of the medicinal composition according to the present invention include, but not limited to, an injection, cream, ointment, tablet, suspension, or the like. Examples of the way of administration include, but not limited to, injection, and oral, topical, intranasal and intrarectal administration, etc.

<Method for Inhibition of Proliferation>

The invention provides a method for inhibition of cancer cell proliferation comprising bringing cancer cells into contact with a proliferation inhibitor according to the present invention. It may also be the medicinal composition according to the present invention that are brought into contact with cancer cells.

There is no particular limitation as to the amount of the proliferation inhibitors according to the present invention to be applied to cancer cells, but it may be determined as desired in accordance with the types and amount of the expression inhibitor compounds contained therein. In the case where the expression inhibitor compound is an siRNA, it is applied preferably in an amount of 1-100 nmole per $1 \times 10^4$ cells, more preferably 5-50 nmole, and most preferably 5-10 nmole. In the case where the expression inhibitor compound in an antisense, it is applied preferably in an amount of 1-100 μmole per $1 \times 10^4$ cells, more preferably 5-50 μmole, and most preferably 5-20 μmol.

In practicing the method for inhibition of proliferation according to the present invention, it is sufficient to bring one of the aforementioned cancer cell proliferation inhibitor agents into contact with cancer cells. There is no particular limitation as to how this is done, which, for example, may be determined in accordance with the type of the expression inhibitor compound contained in the proliferation inhibitor agent. In the case where the proliferation inhibitor agent is an siRNA, it may be brought into contact with the cancer cells together with a transfection reagent known in the art to introduce the siRNA into the cells. In the case where an antisense is employed, the same procedure may be followed. The medicinal compositions according to the present invention may also be used in the same manner.

<Method for Treatment>

The proliferation inhibitor agents and the medicinal compositions according to the present invention can not only be applied to cancer cells or tissues in vitro, but also be used to treat cancer patients. Namely, the proliferation inhibitor agents or the medicinal compositions according to the present invention may be administered to cancer patients to bring the cancer cells into contact with the expression inhibitor compounds. According to this method, reduction of side effects is expected, for example, on normal cells, the cells that have been fully differentiated. The reason for this is as follows. As will be shown later in Examples, HP1γ protein cannot be detected in normal, differentiated cells. Namely, even if administered with a proliferation inhibitor agent according to the present invention, normal, differentiated cells already lacks expression of HP1γ protein. Therefore, normal, differentiated cells, even if brought into contact with a proliferation inhibitor agent according to the present invention, are hardly thought to be affected by any suppression of expression of HP1γ protein.

Examples of patients include humans, mammalian animals other than humans, and other animals. There is no particular limitation as to the way in which the proliferation inhibitors and medicinal compositions according to the present invention are administered, and in accordance with the site to be treated, such a way of administration may be chosen as injection, topical application, or surgical treatment to implant the inhibitors in the affected site or under the skin. A delivery system known in the art may also be employed in accordance with the site where administration is to be made. Further, as needed, it is also possible to construct an siRNA expression vector which will express an aforementioned siRNA, and thus to utilize a delivery system based on the technique of gene therapy.

<Screening Method>

The screening method according to the present invention is a method of screening for cancer cell proliferation inhibitor agents, which comprises the steps of; bringing HP1γ gene into contact with candidate compounds, detecting expression of HP1γ gene, and selecting, as cancer cell proliferation inhibitor agents, those candidate compounds which were found to inhibit the expression of HP1γ gene. Employing this method, it becomes possible to construct novel agents which inhibit expression of HP1γ gene. There is no further limitation as to such compounds insofar as they inhibit expression of HP1γ gene (expression of HP1γ protein), and they may be polynucleotides (oligonucleotides), proteins, or low molecular-weight compounds.

EXAMPLES

Examples of the present invention then will be described below together with Comparative Examples. The present invention, however, is not limited by the Examples and Comparative Examples. Unless otherwise noted, "%" means "w/v %".

<Method for Cell Culture>

3T3-L1 mouse preadipocytes were cultured in Dulbecco's modified Eagle's medium (DMEM; Sigma) supplemented with 10% bovine serum (BS). Colon cancer cells DLD-1, HCT116 and HT-29; lung cancer cells NCI-H23; and gastric cancer cells MKN1 and MKN28 were cultured in RPMI1640 medium (Sigma) supplemented with 10% fetal bovine serum (FBS); uterine cervical cancer cell HeLa and SiHa in DMEM medium supplemented with 10% FBS. To any of the media used in Examples were added 1% penicillin and 1% streptomycin. The condition of the culture was set at 37° C. in 5% CO2 atmosphere.

<Antibody>

Antibodies employed were; mouse monoclonal antibodies to HP1α, HP1β and HP1γ, respectively (Chemicon); rabbit polyclonal antibody to $Met_3H4K20$ (Upstate); rabbit polyclonal antibodies to AceH3K18, $Met_2H3R17$, $Met_2H3K4$, AceH4K12, AcetH4K16, AceH3K9, $Met_2H3K9$ and AceH4K8, respectively (Abcam); and anti-CAPD antibody to GAPDH (Santacruz) as a control.

Example 1

1. Expression of HP1γ Protein in the Process of Cell Differentiation

The relation between cell differentiation and expression of HP1γ protein was examined.

(1) Expression of HP1γ Protein Concurrent with Cell Differentiation

3T3-L1 mouse preadipocytes were cultured to confluence in DMEM medium supplemented with 10% BS, and their differentiation into adipocytes were induced by culturing them under the following condition. First, the preadipocytes were transferred to a first differentiation-inducing medium (10% FCS, 0.5 mM 3-isobutyl-1-methylxanthine, and 1 μM dexamethasone), and cultured for two days. The cells then were transferred to a second differentiation-inducing medium (DMEM medium contain 10% FBS and 10 μg/mL insulin), in which they were cultured for two days, and then to a third differentiation-inducing medium (DMEM medium containing 10% FBS), in which culture was performed for a predetermined length of time (for; 0 day, 3 days, 6 days, 9 days, or 14 days) for induction of differentiation. 3-Isobutyl-1-methylxanthine, dexamethasone, and insulin are differentiation inducers (adipose reagents), and, by being cultured in the presence of these differentiation inducers, 3T3-L1 cells generally will change their shape from a one that is characteristic of a fibroblast-like phenotype into a round shape, and form lipid droplets, which will accumulate in the cells. On the other hand, human preadipocytes were cultured in a preadipocyte medium (DMEM/Ham's F12 (1:1) Gibco BRL, 10% FBS) to confluence, then cultured in a forth differentiation-inducing medium (3% FBS, 1 nM dexamethasone, 100 nM human insulin, 0.25 mM 3-isobutyl-1-methylxanthine, 10 μM PPARγ agonist) for two days, and then transferred to a fifth differentiation-inducing medium (3% FBS, 1 nM dexamethasone, 100 nM human insulin), in which they were cultured for a predetermined length of time (treatment for differentiation induction for; 0 day, 3 days, 6 days, 9 days, or 14 days). Regarding the term during which the treatment for differentiation induction was performed in the above, day 0 was assigned to the point of time in the case of 3T3-L1 mouse preadipocytes, when the first differentiation-inducing medium was added, and, in the case of human preadipocytes, to the point of time when the forth differentiation-inducing medium was added, respectively.

The cultured cells thus prepared then were examined for the expression of HP1 proteins (α, β, γ) by western blotting.

First, proteins were extracted from the cultured cells by a method known in the art, and suspended in an SDS-PAGE buffer. The suspension thus prepared was heat-treated to denature the proteins and then applied, in an amount containing 10 μg proteins, to 15% SDS-PAGE for electrophoresis. The proteins thus electrophoresed were transferred to a membrane (Immobilon™ membrane; mftd. by Millipore) by semi-dry method, and antibodies to the proteins to be detected (HP1α, HP1β, HP1γ) were applied to the membrane for letting the proteins immobilized on the membrane undergo an antigen-antibody reaction with the antibodies. Thus obtained antigen-antibody complexes were detected on a detector (LAS-3000™ mini: mftd. by Fuji Film) following exposure of an autoradiography film after causing chemical luminescence using a kit containing an enzyme-labeled secondary antibody and a fluorescent reagent (product name: ECL plus:

mftd. by Amersham). As a control, the expression of GAPDH protein was examined in the same manner.

The results are shown in FIG. 1(A). FIG. 1(A) is autoradiograms showing the time profiles of the expression of different proteins (HP1α, HP1β, HP1γ) in 3T3-L1 mouse preadipocytes and human preadipocytes in both of which differentiation had been induced. In the figure, the results in 3T3-L1 cells are on the left, and those in human preadipocytes on the right.

As shown in the above figure, of HP1 proteins, HP1α and HP1β proteins were found expressed at all the stages (from day 0 to day 14) of differentiation into adipocytes. In contrast, the expression of HP1γ protein was found reduced on day 9 of treatment for differentiation induction, and no longer detectable on day 14. The fact that the amount of expressed HP1γ protein thus reduced as differentiation proceeded and became hardly detectable in differentiated cells suggests that the decline of HP1γ protein expression is playing some role in cell differentiation. Although it has been reported that the all three HP1 homologues have reduced in their amount in fully differentiated cells (e.g., blood cells) (Non-patent documents 4, 5, and 6), HP1γ alone, of the HP1 homologues, as mentioned above, is thought to play a role in differentiation. This was first revealed by the present inventors.

(2) Effect of Ectopic Expression of HP1γ Protein on Cell Differentiation

Examination was performed to find out whether ectopic expression of HP1γ protein has some effect on cell differentiation.

(2-1) Establishment of an HP1γ-Expressing Cell Line

As follows, starting with 3T3-L1, a cell line was established in which the expression of HP1γ protein is constantly induced with mifepristone.

Using total RNA form HCT116 cells, which were colon cancer cells, as a template, reverse transcription PCR was carried out to amplify HP1γ cDNA. HP1γ cDNA thus amplified was directly subcloned into the pCR2.1 vector (mftd. by Invitrogen) to prepare a recombinant vector pCRHP1γ. The pCRHP1γ was cleaved with EcoRI, and the EcoRI fragment containing HP1γ cDNA was subcloned into the EcoRI site of the pGene-V5 (mftd. by Invitrogen) to prepare pGHP1γ. Then, to 3T3-L1 placed in a cell culture dish of 100 mm in diameter were introduced 3 µg of a regulating plasmid (pSwitch vector) and 7 µg of pGHP1γ were introduced. As a control, the empty vector pGene-V5 was introduced instead of pGHP1γ. Their introduction was performed using DoFect GT1 transfection reagent (mftd. by Dojin) according to the product's manual. Selection of the cells that harbored these introduced plasmids was done using 400 µg/mL of Zeocin (registered trademark, mftd. by Invitrogen) and 50 µg/mL of hygromycin (product name, mftd. by Invitrogen). The cells thus obtained was a mifepristone-inducible HP1γ gene expression cell line (hereinafter referred to as "plasmid-introduced cells").

(2-2) Confirmation of Ectopic Expression of HP1γ Protein

The cell line thus obtained and plasmid-unintroduced 3T3-L1 (hereinafter referred to as "plasmid-unintroduced cells") were separately cultured in the presence of 1×10$^{-7}$ M mifepristone, the inducer, to induce the expression of HP1γ protein. The culture was performed using multiple inducing media as described in "1.(1)" above, and mifepristone was added to every medium. Further, to examine the effect of differentiation induction and that of expression induction, additional culture was also performed in the absence of mifepristone or the inducing agents (adipose reagents). The cells thus cultured were analyzed by western blotting in the same manner as described in "1.(1)" above, and this confirmed that the expression of HP1γ protein had been induced. As a control, the same analysis was made on GAPDH protein.

The results are shown in FIG. 1(B). FIG. 1(B) is a set of autoradiograms showing the expression of HP1γ protein in 3T3-L1. In the figure, "tr" indicates the results obtained from the mifepristone-inducible HP1γ-expressing 3T3-L1 (plasmid-introduced cells), and "wt" those from 3T3-L1 in which no recombinant plasmid pGHP1γ had been introduced (plasmid-unintroduced cells). "Mifepristone (+) (−)" indicates whether the culture was performed in the presence, or absence, of mifepristone, and "adipose reagents (+) (−)" indicates whether the culture was performed in the presence, or absence, of the differentiation inducers.

As shown in the figure, it was confirmed that in the plasmid-introduced cells, unlike plasmid-unintroduced cells, expression of HP1γ gene was induced in the presence of mifepristone, and this caused an increase in the amount of HP1γ protein.

(3) Effect of HP1γ Expression on Cell Differentiation

The plasmid-introduced cells and plasmid-unintroduced cells, both cultured in the same manner as is described in (2) above, were examined for accumulation of lipid droplets within the cells. As aforementioned, 3T3-L1 cells change their phenotype when differentiation is induced, and they form lipid droplets and accumulate them within the cells. Therefore, assay of cells as to whether they have differentiated or not can be done by detecting lipid accumulation within the cells. Assay of cells differentiation was performed with oil red staining using an analysis kit (product name: Adipogenesis Assay kit; mftd. by Chemicon).

The results are shown in FIG. 1(C). The figure is a set of photographs showing the results of the oil red staining of 3T3-L1. In the figure, "transfectant" indicates the results of mifepristone-inducible HP1γ expression system 3T3-L1 (plasmid-introduced cells), and "wt" the results of 3T3-L1 into which no recombinant pGHP1γ had been introduced (plasmid-unintroduced cells). And "mifepristone (+) (−)" indicates a culture in the presence, or absence, of mifepristone, and "adipose reagents (+) (−)" a culture in the presence, or absence, of differentiation inducers.

As shown in the figure, in the plasmid-unintroduced cells cultured in the presence of differentiation inducers (adipose reagents +), positive staining (i.e., accumulation of lipid droplets) was detected regardless of whether the culture had been done in the presence or absence of mifepristone. Thus, it was proved that differentiation is surely induced in the plasmid-unintroduced cells when differentiation inducers are present. In contrast, in 3T3-L1 cells which had been transformed into an HP1γ expression system (plasmid-introduced cells), though positive staining was detected in the presence of differentiation inducers when mifepristone was absent, no positive staining was detectable when mifepristone was present. Thus, in the presence of mifepristone, cell differentiation was not induced either in the presence or absence of differentiation inducers. This result shows that HP1γ protein, which was induced by mifepristone, inhibited cell differentiation, and that inhibition of the expression of HP1γ protein is necessary for cell differentiation to take place.

2. Correlation Between HP1 Expression and Histone Modification (1) Time Course of Histone Modification During Cell Differentiation Modification of histone, which is a component of chromatin, is one of epigenetic mechanisms, and is known to be important for cell differentiation (Non-patent Document 7).

Thus, we examined the time course of histone modification in 3T3-L1 during cell differentiation. First, culture of 3T3-L1 mouse preadipocytes was performed in the same manner as described in "1.(1)" above except that the duration of culture in the aforementioned third differentiation-inducing medium was set at certain length of time (0 day, 1 days, 2 days, 3 days, 4 days, 6 days, 8 days, 10 days, or 14 days). And, except that the above-mentioned various antibodies were employed, western blotting was performed in the same manner as described in "1.(2)" above to detect HP1γ, AceH3K9, AceH3K18, Met$_2$H3K4 (DiMetH3K4), Met$_2$H3K9 (DiMetH3K9), Met$_2$H3R17 (DiH3R17), AceH4K8, AceH4K12, AcetH4K16, Met$_3$H4K20 (TriMetH4K20), as well as GAPDH which was a control.

Figure 2:
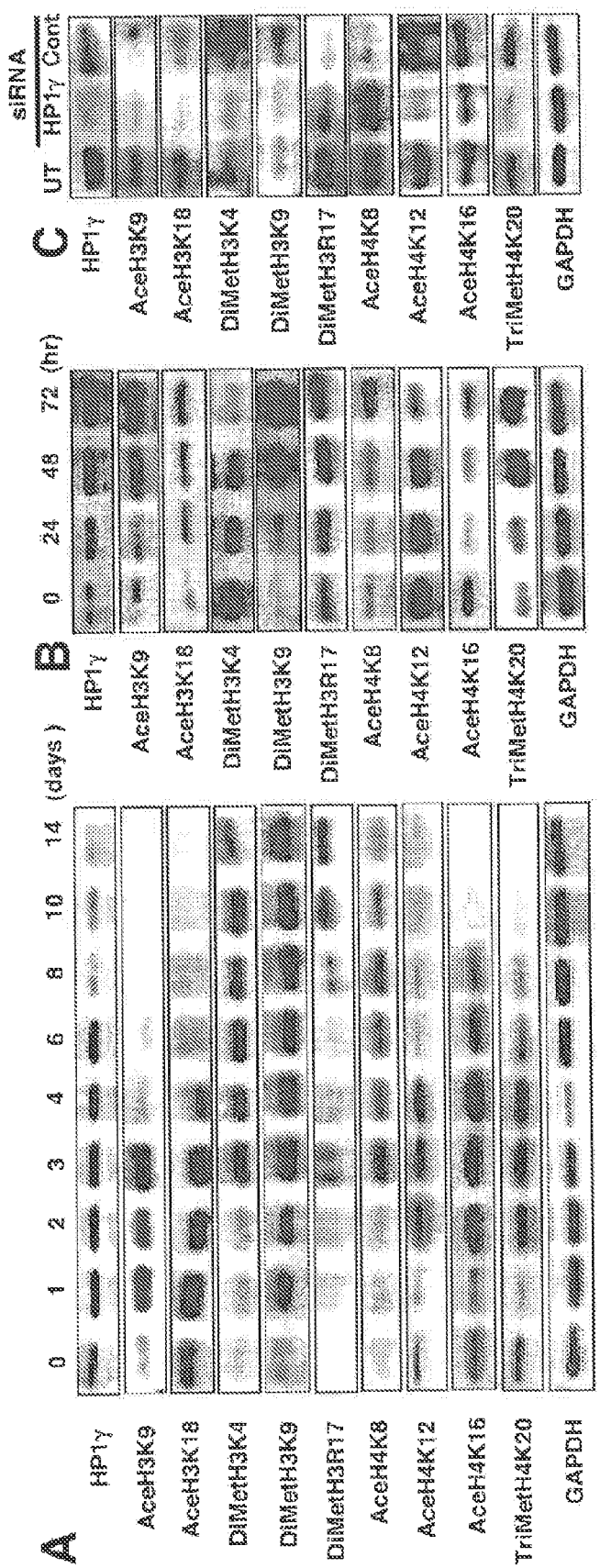

The results are shown in FIG. 2(A). The figure is a set of autoradiograms showing the time course of histone modification during differentiation of 3T3-L1. As shown in the figure, the acetylation levels at K9 and K18 of histone H3, and at K2 and K16 of histone H4, were equally lowered along with the decreasing amount of expressed HP1γ protein which occurred as the cell differentiation proceeded. In contrast to this, and contrary to the decrease in HP1γ protein expression occurring along with cell differentiation, methylation at K4, arginine (R9) and K17 of histone H3 increased with time.

(2) Relation Between HP1γ Protein Expression and Histone Modification Levels in Differentiation Further, examination was conducted to find out whether the expression of HP1γ protein directly effects on the levels of the above histone modifications. This was done, using the mifepristone-inducible HP1γ expressing 3T3-L1 (plasmid-introduced cells) prepared in "1.(2)" above, by western blotting of histone modification, at 4-hour intervals for 72 hours after the start of mifepristone treatment. The condition for cell culture was the same as that in "1.(1)" above, and the western blotting was performed in the same manner as described above.

The results are shown in FIG. 2(B). The figure is a set of autoradiograms showing the time course of the expression of HP1γ protein and histone modification. As shown in the figure, along with the over-expression of HP1γ protein, the levels of acetylation of K18 of histone H4 and trimethylation of K20 of histone H4 rose, while those of acetylation of K12 of histone H4 and dim ethylation of K4 of histone H3 declined.

(3) Relation Between Suppression of HP1γ Gene Expression and Histone Modification Levels By means of RNA interference using siRNAs which inhibit HP1γ gene expression, examination was conducted to find out a relation between trimethylation levels of histone H4K20 and the expression of HP1γ protein.

Using 12 μL of HiPerFect reagent (product name, mftd. by Qiagen) per 60-mm culture dish, 3T3-L1 mouse preadipocytes were transfected following the manual attached to the reagent, with 50 nM siTrio (registered trademark) Full Set (mftd. by B-Bridge) containing siRNAs specific to mouse HP1α, HP1β and HP1γ gene, respectively. The siRNA sequences (shown by sense strands only) specific to HP1α were 5'-GGGAGAAAUCAGAAGGAAATT-3' (SEQ ID NO:114), 5'-GCGAAGAGCUAAAGGAGGATT-3' (SEQ ID NO:115), and 5'-GGAUACAGUCUGAGAGUUATT-3' (SEQ ID NO:116); siRNA sequences specific to HP1β were 5'-GGUACUAGAAGAAGAGGAATT-3' (SEQ ID NO:117), 5'-GGCGAGUUGUCAAGGGCAATT-3' (SEQ ID NO:118), and 5'-GAAAACAGCUCAUGAGACATT-3' (SEQ ID NO:119); siRNA sequences specific to HP1γ were 5'-GGACCGUCGUGUAGUGAAUTT-3' (SEQ ID NO:120), 5'-CCGACUUGGUGCUGGCAAATT-3' (SEQ ID NO:121), and 5'-GGAAAAUGGAAUUAGACUATT-3' (SEQ ID NO:122). In each of these sequences, "TT" on the 3'-end is the overhang. Following the transfection with those siRNAs, the 3T3-L1 cells were cultured for 72 hours, and their whole cell lysates were subjected to western blotting in the same manner as described above. As a negative control, siRNA (SEQ ID NO:123, 5'-AUCCGCGC-GAUAGUACGUAdTdT-3')(mftd. by B-Bridge) was used to transfect 3T3-L1 with.

The results are shown in FIG. 2(C). The figure is a set of autoradiograms showing the levels of histone modification and HP1γ expression when treated with an siRNA specific to each HP1 gene. It was found that trimethylation of histone 4HK20 and the expression of HP1γ protein closely correlate as seen in the figure.

3. Tendency in Terminal Differentiated Cells of Each Tissue

Examination was carried out to find out whether HP1γ protein and trimethylated K20 of histone H4 disappeared not only in differentiated adipocytes but also in terminal differentiated cells of various other tissues.

As tissue samples, fat, esophageal mucosa, skin tissues, and colon were employed. These tissues was examined for localization of HP1γ protein and trimethylated histone H4K20 (Met$_3$H4K20) by immunohistochemical analysis. Specifically, slices of formalin-fixed, paraffin-embedded samples were prepared from the above-mentioned tissues according to a conventional method, and then examined on an automatic immunostaining apparatus (product name: Ventana HX System Benchmark, mftd. by Ventana Medical Systems). Antibodies used were anti-human HP1γ monoclonal antibody and anti-Met$_3$H4K20 polyclonal antibody, which were applied after diluted to the ratios of 1:800 and 1:200, respectively (antibody:diluent). Furthermore, hematoxylin and eosin staining (H&E staining) of each tissue was performed for histological examination.

Figure 3:
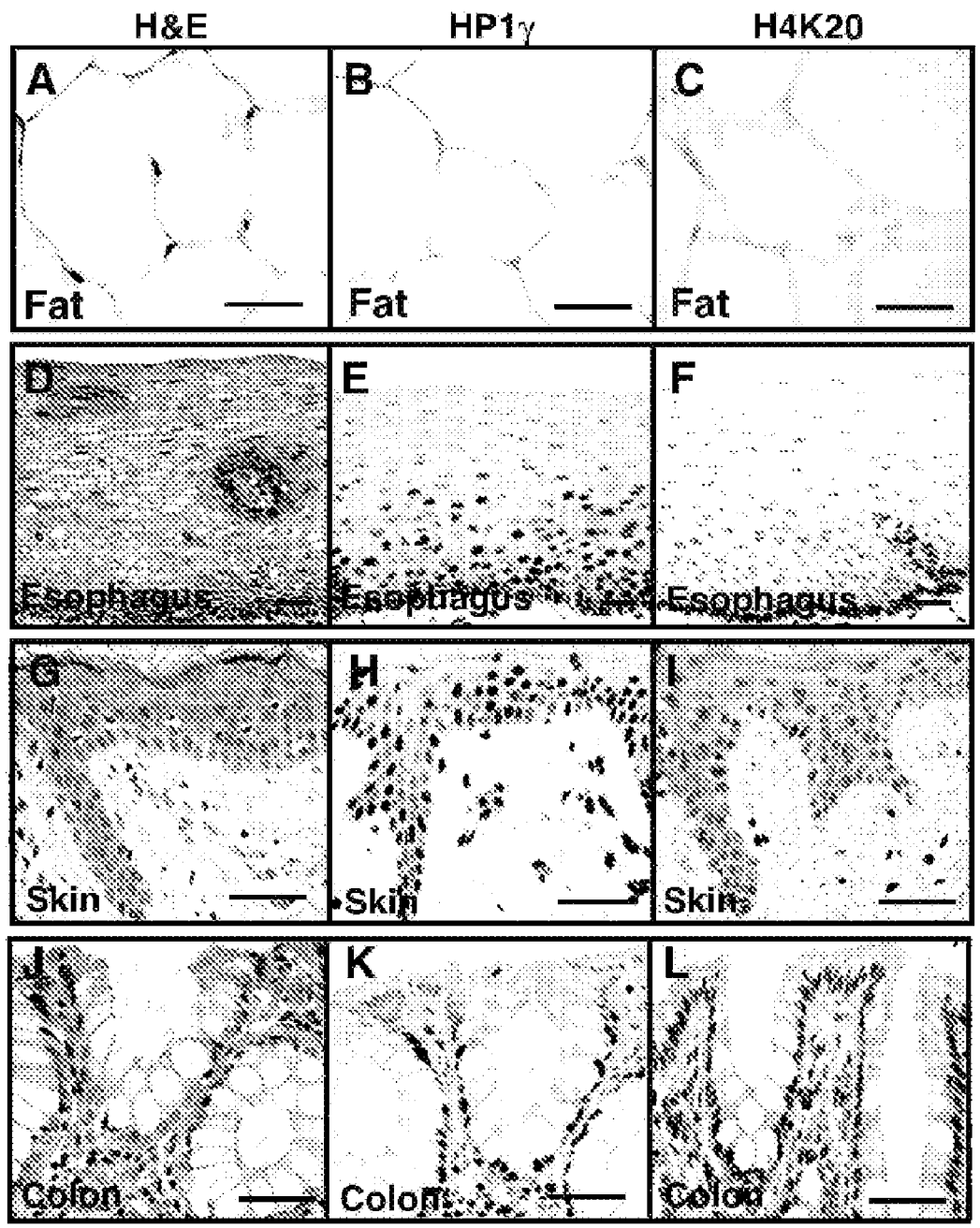
FIG. 3 is a set of photographs showing the result of immunostaining of tissues in still another example of the present invention.

The results are shown in FIG. 3. The figure is a set of photographs showing the result of immunostaining of the tissues. In the figure, the results are: (a-c) of adipose tissue, (d-f) of esophageal mucosa, (g-i) of dermal tissue, and (j-l) of colonic normal cells. The left column shows the result of H&E staining of the tissues, the center column the result of immunostaining of the tissues which visualizes localization of HP1γ, and the right column the result of immunostaining of the tissues which visualizes localization of Met$_3$H4K20.

Occurrence of HP1γ protein was confirmed in premature cells of the tissues (figure not presented). However, as shown in b and c of the figure, neither HP1γ protein nor Met3H4K20 was detected in mature adipocytes (terminal differentiated cells) in the adipose tissue, and, likewise, neither HP1γ protein nor Met$_3$H4K20 was detected in terminal differentiated cells in the esophageal mucosa or the dermal tissue, as shown in e, f, h and i of the figure. Moreover, as shown in k and l of the figure, neither HP1γ protein nor Met$_3$H4K20 was detected on the surface of differentiated mucosa of the colonic tissue. These results indicates that the disappearance of HP1γ protein and Met$_3$H4K20 is related to the differentiation of the cells regardless of which tissue the cells belong to. HP1γ protein is thought to be bound to methylated K20 residues of histone H4 and bind to Suv4-20h1, Sub4-20h2 and/or histone methyl transferase. Thus, the molecular interaction between HP1γ gene and histone H4K20 is thought to be a key mechanism to cell differentiation.

4. Enhanced Expression of HP1γ Protein in Human Malignant Tumors

Human various malignant tumors (cancers) were examined for expression of HP1γ protein and trimethylation levels of histone H4K20.

Tissue samples of malignant tumors employed were those of esophageal cancer, uterine cervical cancer, colorectal cancer, breast cancer, lung cancer, and myxoid liposarcoma, which had been surgically excised (n=26). These cells were examined for localization of HP1γ protein and trimethylated histone H4K20 (Met₃H4K20) by immunohistochemical staining in the same manner as described in "3." above.

Typical examples of these results are shown in FIG. 4-1, FIG. 4-2, and FIG. 4-3. These figures are photographs showing the results of immunostaining of the malignant tumors. In these figure, "H&E" indicates the results of H&E staining, "HP1γ" the results of staining which reveals the localization of HP1γ protein, and "TriMeH4K20" the results of staining which reveals the localization of TriMeH4K20 (Met₃H4K20). As shown in the figures, HP1γ protein was detected in the cell nuclei of all the cell samples of malignant tumors, and the same result was obtained also in the other samples, which are not presented in figures (n=26). Furthermore, trimethylated K20 of histone H4 was detected in 17 cases out of these 26 case samples.

Figures 1, 4:
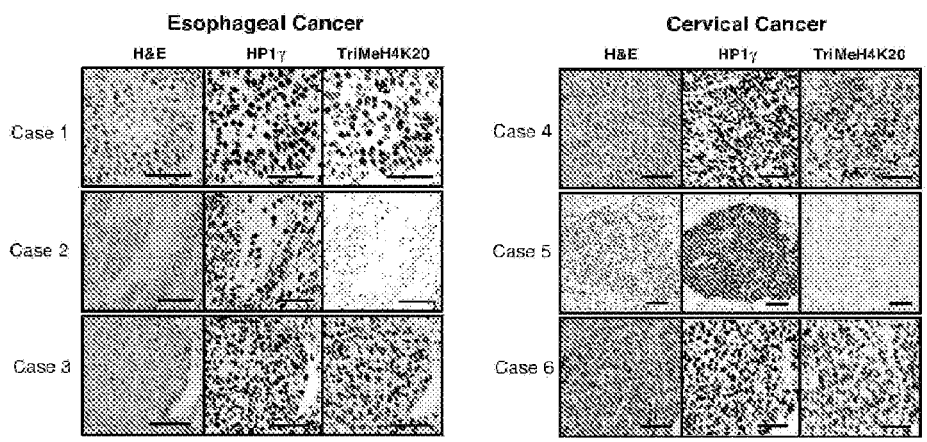
Figures 2, 4:
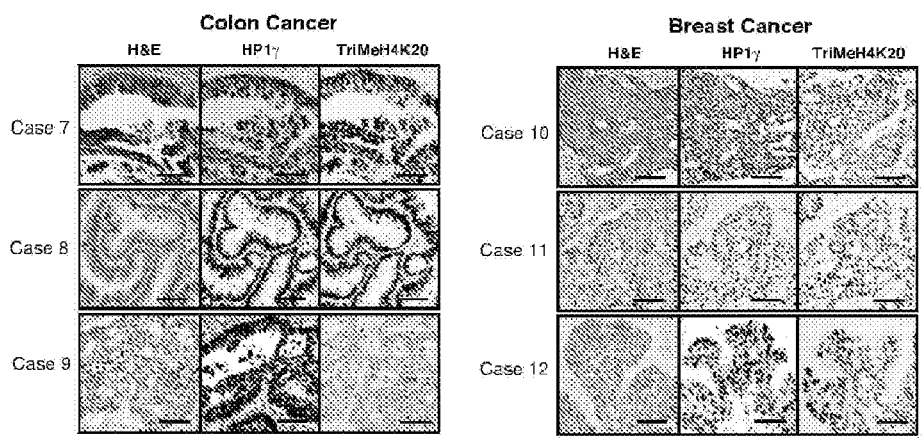
Figures 3, 4:
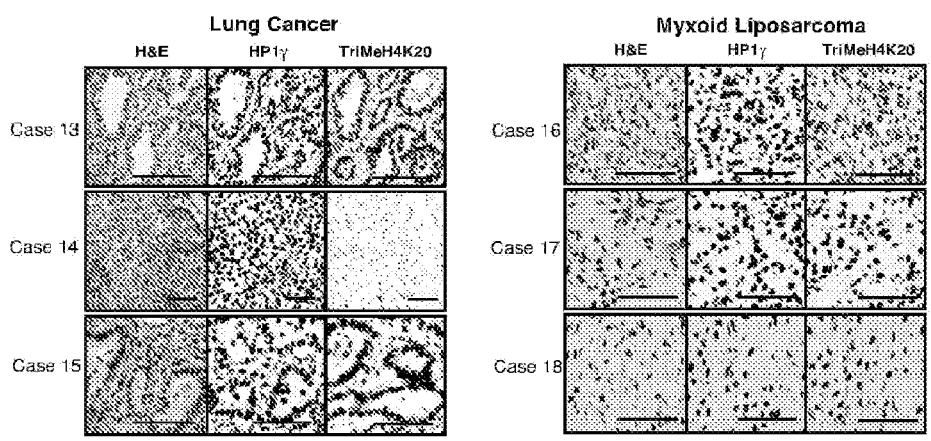

As shown in "3." above, a correlation was found between the expression of HP1γ protein and trimethylation of histone H4K20 in normal differentiated cells. For example, there was a correlation that when HP1γ protein was found positive, trimethylation was also found positive in the undifferentiated cells. On the other hand, in the differentiated cells there was a correlation that where HP1γ was found negative, trimethylation was also found negative. In contrast to this, with malignant tumor cells, as shown in FIG. 4, there are many cases in which HP1γ protein was detected (positive) but histone trimethylation of H4K20 was found negative. Thus, it is thought to be characteristic of malignant tumor cells that the tie between the expression of HP1γ protein and trimethylation of histone H4K20 seen in normal cells is dissociated. The results indicate that normal differentiated cells and tumor cells can be distinguished from each other by detecting HP1γ protein.

It has already been reported that the loss of trimethylated histone H4K20 is a notable characteristic of cancer cells (Non-patent document 8). Considering this in combination with the aforementioned results obtained in normal differentiated cells, it must be difficult, by detection of trimethylation of histone H4K20 alone, to distinguish between normal differentiated cells and malignant tumor cells. However, as aforementioned, there is a tendency that HP1γ protein is found negative in normal differentiated cells and positive in malignant tumor cells. Therefore, while a loss of trimethylation of histone H4K20 reported so far alone will not serve to distinguish tumor cells, further detection of the expression of HP1γ will allow one to identify cells as being normal ones if the expression of HP1γ in them has been reduced, and tumor cells if the expression of HP1γ has been increased.

Example 2

Inhibition of Proliferation of Malignant Tumor Cells by Means of Suppression of HP1γ Expression Using RNA Interference The suppressive effect of siRNAs on proliferation of malignant tumor cells was examined.

Malignant tumor cells employed were: human cell lines DLD-1, HCT116 and HT-29 (colon cancer); MKN1 and MKN28 (gastric cancer); HeLa and SiHa (uterine cervical cancer); NCI-H23 (lung cancer); and 402/91 and 2645/94 (myxoid liposarcoma). These cells were transfected with 5 nM or 50 nM of a double-stranded siRNA oligonucleotide (SEQ ID NO:124: 5'-UGACAAACCAAGAGGA-UUUdTdT-3', mftd. by B-Bridge), which corresponds to human HP1γ gene, with HiPerFect reagent (product name, mftd. by Qiagen) according to the manual attached to the reagent. The siRNA presented as SEQ ID NO:124 is the one indicated as #62 (sense strand of SEQ ID NO:1, antisense strand of SEQ ID NO:253) in Table 2D, on the 3'-end of which is attached an overhang consisting of two thymidine (T) bases. As a negative control, the siRNA mentioned above in "2.(3)" (SEQ ID NO:123: 5'-AUCCGCGC-GAUAGUACGUAdTdT-3')(mftd. by B-Bridge) was used in the same manner to transfect 3T3-L1. After transfection, the cells were cultured for four days as aforementioned in accordance with the type of the cells, and after treated with a cell staining dye (product name: trypan), counted for viable cells on hemocytometer (product name "erythrometer"). Analyses were performed three times for each cancer cell types. As a control, siRNA-unintroduced tumor cells of each cancer type were also counted in the same manner for viable cells.

Figure 5:
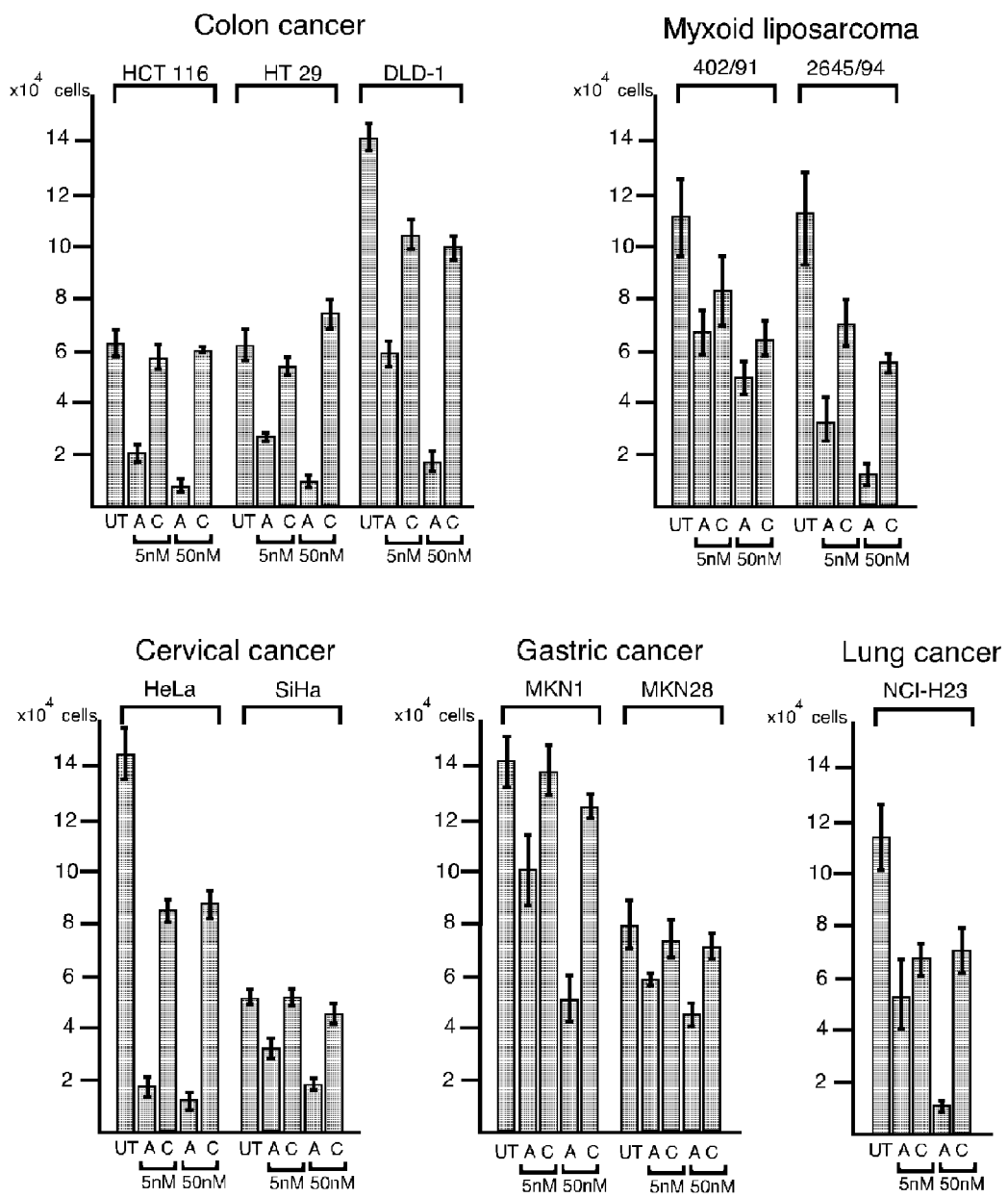
FIG. 5 is a graph showing the number ($\times 10^4$ cells) of viable cells of various tumors.

The results are presented graphically in FIG. 5. The figure is a set of graphs showing the number of the viable cells (×10⁴ cells) among each type of tumor cells. In the figure, "UT" means the results in the cells which were not treated with siRNA, "A" the results of introduction of double-stranded siRNA to human HP1γ gene, and "C" the results of introduction of the negative control siRNA. As seen in the figure, by suppressing HP1γ gene through introduction of siRNA corresponding to human HP1γ gene, proliferation of tumor cells was inhibited. Thus, as proliferation of tumor cells is inhibited by suppressing the expression of HP1γ gene (expression of HP1γ protein) in tumor cells, HP1γ gene is very useful as a target gene for cancer treatment.

Example 3

Examination of the Suppressive Effect of siRNA on HP1γ Expression in Human Malignant Tumor Cells Examination was performed of siRNAs which are specific to human HP1γ on their suppressive effect on human HP1γ gene expression. SiRNAs employed were: #17 (sense strand: SEQ ID NO:49, antisense strand: SEQ ID NO:208), #62 (sense strand: SEQ ID NO:1, antisense strand: SEQ ID NO:253), and #89 (sense strand: SEQ ID NO:74, antisense strand: SEQ ID NO:280) presented in Table 2A-F, each of which had two deoxythymidine nucleotides(dTdT) as the 3'-overhang sequences, and which are shown as g-1 to g-3 siRNAs in FIG. 6, as well as a mixture of the three (Mix), and human malignant tumor cells transfected with them were examined for any suppression of human HP1γ expression. Malignant tumor cells employed were human cancer cell line DLD-1, which were transfected with each of the siRNAs (5 nM) or their mixture (5 nM each) in the same manner as described in Example 2. As a negative control, siRNA (SEQ ID NO:123)(mftd. by B-Bridge) described in "2.(3)" above was used. After transfection, culture was performed as described in Example 2, and the potency of HP1γ expression was examined by western blotting 3 and 5 days after the start of the culture. The results are shown in FIG. 6.

Figure 6:
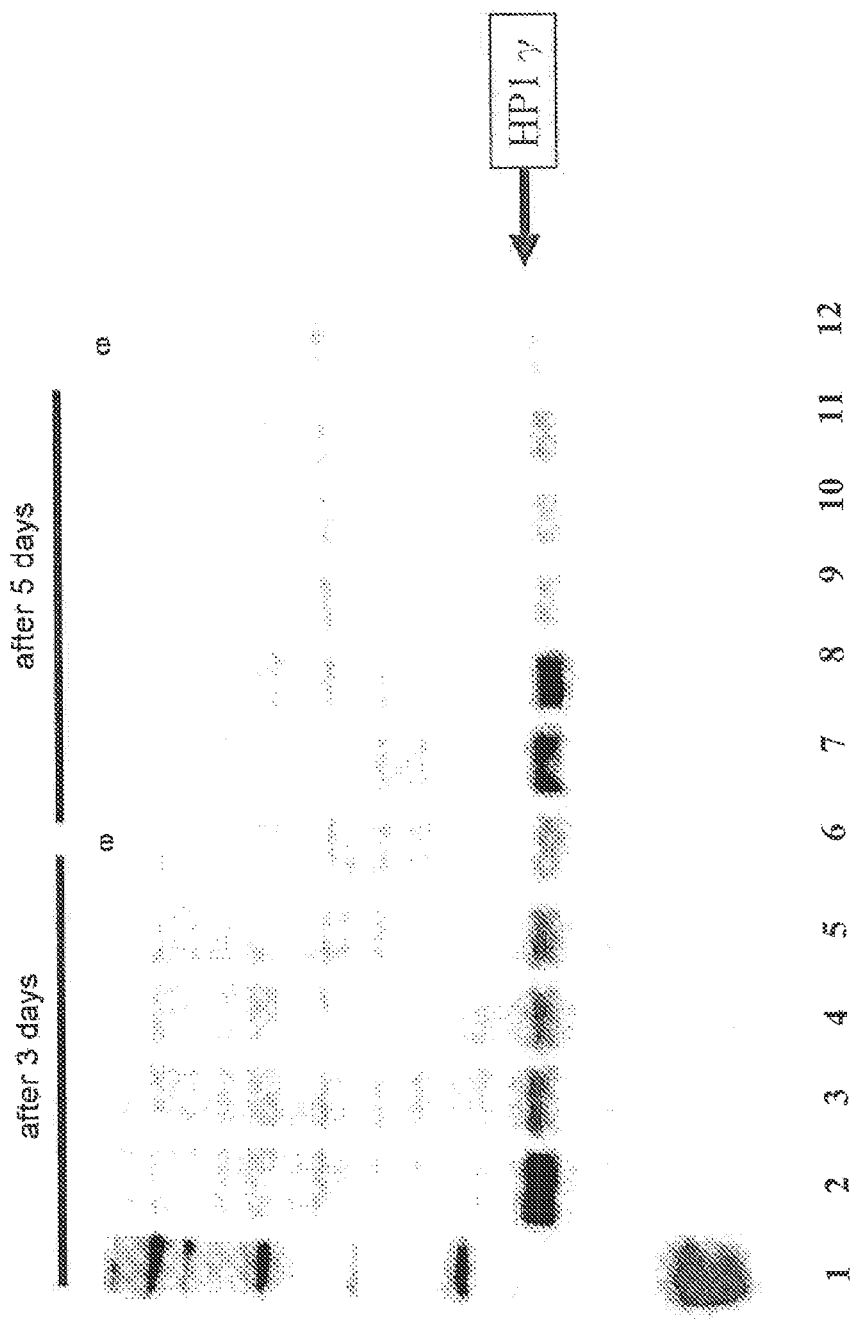
FIG. 6 shows the result of western blotting exhibiting the inhibitory effect of siRNA of the present invention on HP1γ expression in a human cancer cell line.

As evident from FIG. 6, it is confirmed that all the human HP1γ-specific g-1 to g-3 siRNAs strongly inhibit the expression of HP1γ to a similar degree to one another, and that their effect becomes all the more notable with the lapse of days. Further, the mixture of these siRNAs (total concentration being triple) exhibited still more notable effect. On the other hand, the negative control, mouse siRNA, did not show any inhibitory effect. These results indicate that the above-mentioned human HP1γ-specific siRNAs do work specifically to human HP1γ gene as expected, and that their inhibitory effects on HP1γ expression are highly potent. In the figure, "UT DLD-1" indicates the untreated control.

Example 4

Examination of the Therapeutic Effect on Cancer in vivo

Nude mice were transplanted with human malignant tumor cells, and the inhibitory effect of siRNAs of the present invention on the proliferation of them was examined. Namely, nude mice (3 animals per group) were subcutaneously transplanted with 1×10⁶ cultured DLD-1 cells, cells originating from human colorectal cancer. One week after the transplantation, when the cance had grown to a sufficient size under the skin, (a) the animals of the control group was injected, at the site of tumor, with a mixture solution of one μL of a 10 μM negative control siRNA, 2 μL of Oligofectamine (mftd. by Invitrogen) and 89 μL Opti-MEM (mftd. by Invitrogen), (b) the animals of the test agent-injected group were injected with a mixture solution of one μL of a 10 μM human HP1γ-specific siRNA (SEQ ID NO:124), 2 μL of Oligofectamine (Invitrogen) and 89 μL of Opti-MEM I (mftd. by Invitrogen), and (c) the animals of the test agent externally-applied group were externally applied with a preparation which was a cream containing human HP1γ-specific siRNA (SEQ ID NO:124). The cream was prepared by mixing an aqueous solution of the siRNA with a roughly equal weight of neutral fat, and stirring, in the presence of a minute amount of a surfactant and with warming, the mixture to homogeneity. Then, these preparations were administered alike at the interval of three days.

Observation of the animals at their cancer-transplanted site was performed for 22 days after the transplantation. The results are shown in FIG. 7.

Figure 7:
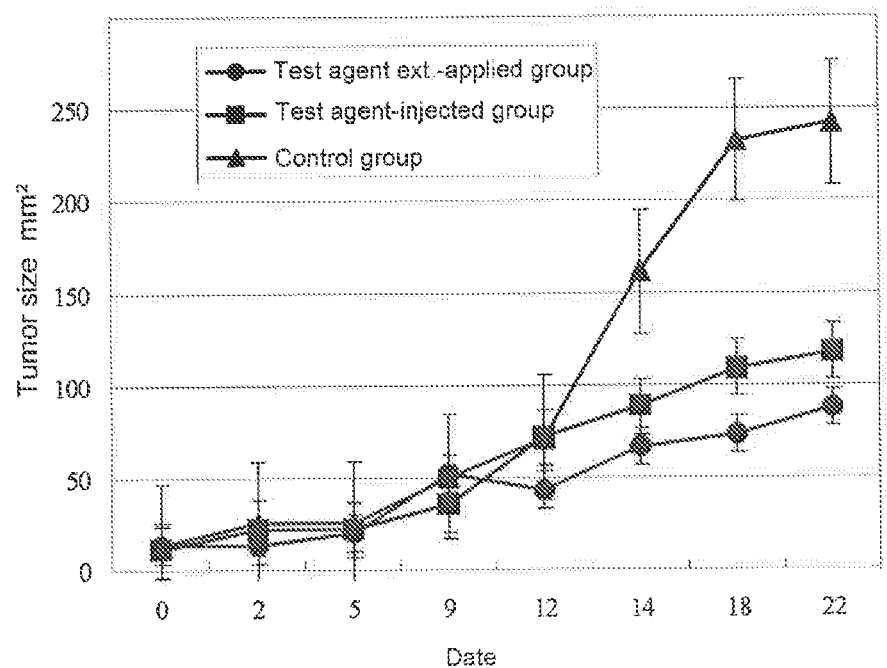
FIG. 7 is a graph illustrating the therapeutic effect of siRNA of the present invention in human cancer-transplanted nude mice.

As seen in FIG. 7, while a rapid growth of the tumor was observed under the skin of the control agent-administered animals, the tumor growth was notably suppressed in either of the test agent-injected group or the test agent externally-applied group. And according to the microscopic examination of HE-stained slices of the tumors 22 days after the start of the observation, tumor cells were found necrosed in the tumors to which the cream was externally applied. In contrast, no necrosis of cells was observed in the control group which was injected with the negative control.

The results shown above demonstrate the usefulness of the HP1γ protein as a cancer cell identification marker, and further the usefulness of the human HP1γ-specific siRNAs of the present invention as cancer cell proliferation inhibitor agents to various cancers, and also as an agent for cancer treatment.

INDUSTRIAL APPLICABILITY

By the method for identification of cancer cells according to the present invention, it is possible to distinguish between cancer cells and normal cells by detecting the presence of HP1γ protein, the identification marker, in the cells. Further, the cancer identification marker according to the present invention, unlike conventions ones, makes it possible to determine whether the cells being examined are cancer cells or not, without regard to the cancer cell types. Moreover, of the HP1γ gene expression inhibitors according to the present invention, the human HP1γ-specific siRNAs can be used for the treatment of a wide variety of human cancers because they inhibit growth of cancers in general regardless of their types.

The invention claimed is:

1. A method for treatment of cancer in a mammal comprising administering, to the mammal in need thereof, an effective amount of a cancer cell proliferation inhibitor agent which is;
- an siRNA which is specific to heterochromatin protein 1γ (HP1γ) gene of the mammal or
- an antisense DNA which is specific to heterochromatin protein 1γ (HP1γ) gene of the mammal.

2. The method for treatment according to claim 1, wherein the mammal is a human and the HP1γ is human HP1γ.

3. The method for treatment according to claim 2, wherein the cancer cell proliferation inhibitor is an siRNA which is specific to human HP1γ.

4. The method for treatment according to claim 3, wherein the siRNA comprises at least one double-stranded RNA selected from #1 to #106, each of which comprises a corresponding RNA strand set forth in the 5' to 3' direction in the following Tables 2A to 2F:

TABLE 2A

|     | SEQ ID NO: | Sequence |
|-----|------------|----------|
| #1  | 39         | CAACAAAACUACAUUGCAA |
|     | 192        | UUGCAAUGUAGUUUUGUUG |
| #2  | 127        | AAAACAGAAUGGAAAGAGU |
|     | 193        | ACUCUUUCCAUUCUGUUUU |
| #3  | 40         | AAACAGAAUGGAAAGAGUA |
|     | 194        | UACUCUUUCCAUUCUGUUU |
| #4  | 128        | AACAGAAUGGAAAGAGUAA |
|     | 195        | UUACUCUUUCCAUUCUGUU |
| #5  | 41         | CAGAAUGGAAAGAGUAAAA |
|     | 196        | UUUUACUCUUUCCAUUCUG |
| #6  | 129        | AAAAGUUGAAGAGGCAGA |
|     | 197        | UCUGCCUCUUCAACUUUUU |
| #7  | 130        | AGUUGAAGAGGCAGAGCCU |
|     | 198        | AGGCUCUGCCUCUUCAACU |
| #8  | 43         | UUGAAGAGGCAGAGCCUGA |
|     | 199        | UCAGGCUCUGCCUCUUCAA |
| #9  | 44         | AGGCAGAGCCUGAAGAAUU |
|     | 200        | AAUUCUUCAGGCUCUGCCU |

TABLE 2A-continued

|     | SEQ ID NO: | Sequence |
|-----|------------|----------|
| #10 | 45         | GGCAGAGCCUGAAGAAUUU |
|     | 201        | AAAUUCUUCAGGCUCUGCC |
| #11 | 46         | CUGAAGAAUUUGUCGUGGA |
|     | 202        | UCCACGACAAAUUCUUCAG |
| #12 | 47         | UGAAGAAUUUGUCGUGGAA |
|     | 203        | UUCCACGACAAAUUCUUCA |
| #13 | 48         | AAGAAUUUGUCGUGGAAAA |
|     | 204        | UUUUCCACGACAAAUUCUU |
| #14 | 131        | AGAAUUUGUCGUGGAAAAA |
|     | 205        | UUUUUCCACGACAAAUUCU |
| #15 | 132        | UGUCGUGGAAAAGUACUA |
|     | 206        | UAGUACUUUUCCACGACA |
| #16 | 133        | UGGAAAAGUACUAGAUCG |
|     | 207        | CGAUCUAGUACUUUUUCCA |
| #17 | 49         | GGAAAAGUACUAGAUCGA |
|     | 208        | UCGAUCUAGUACUUUUUCC |
| #18 | 50         | AGUACUAGAUCGACGUGUA |
|     | 209        | UACACGUCGAUCUAGUACU |

TABLE 2B

|     | SEQ ID NO: | Sequence |
|-----|------------|----------|
| #19 | 51         | AGAUCGACGUGUAGUGAAU |
|     | 210        | AUUCACUACACGUCGAUCU |
| #20 | 134        | GACGUGUAGUGAAUGGGAA |
|     | 211        | UUCCCAUUCACUACACGUC |
| #21 | 52         | ACGUGUAGUGAAUGGGAAA |
|     | 212        | UUUCCCAUUCACUACACGU |
| #22 | 53         | AGUGAAUGGGAAAGUGGAA |
|     | 213        | UUCCACUUUCCCAUUCACU |
| #23 | 135        | GUGAAUGGGAAAGUGGAAU |
|     | 214        | AUUCCACUUUCCCAUUCAC |
| #24 | 54         | UGAAUGGGAAAGUGGAAUA |
|     | 215        | UAUUCCACUUUCCCAUUCA |

TABLE 2B-continued

| SEQ ID NO: | | Sequence |
|---|---|---|
| #25 | 136 | UUCCUGAAGUGGAAGGGAU |
| | 216 | AUCCCUUCCACUUCAGGAA |
| #26 | 137 | UCCUGAAGUGGAAGGGAUU |
| | 217 | AAUCCCUUCCACUUCAGGA |
| #27 | 138 | CUGAAGUGGAAGGGAUUUA |
| | 218 | UAAAUCCCUUCCACUUCAG |
| #28 | 139 | GUGGAAGGGAUUUACAGAU |
| | 219 | AUCUGUAAAUCCCUUCCAC |
| #29 | 140 | UGGAAGGGAUUUACAGAUG |
| | 220 | CAUCUGUAAAUCCCUUCCA |
| #30 | 141 | AUUUACAGAUGCUGACAAU |
| | 221 | AUUGUCAGCAUCUGUAAAU |
| #31 | 142 | GCUGACAAUACUUGGGAAC |
| | 222 | GUUCCCAAGUAUUGUCAGC |
| #32 | 143 | UGACAAUACUUGGGAACCU |
| | 223 | AGGUUCCCAAGUAUUGUCA |
| #33 | 55 | CUUGGGAACCUGAAGAAAA |
| | 224 | UUUUCUUCAGGUUCCCAAG |
| #34 | 144 | UUGGGAACCUGAAGAAAAU |
| | 225 | AUUUUCUUCAGGUUCCCAA |
| #35 | 56 | CAGAAUUGAUUGAAGCGUU |
| | 226 | AACGCUUCAAUCAAUUCUG |
| #36 | 57 | AGAAUUGAUUGAAGCGUUU |
| | 227 | AAACGCUUCAAUCAAUUCU |
| #37 | 145 | UGAUUGAAGCGUUUCUUAA |
| | 228 | UUAAGAAACGCUUCAAUCA |

TABLE 2C

| SEQ ID NO: | | Sequence |
|---|---|---|
| #38 | 146 | GUUUCUUAACUCUCAGAAA |
| | 229 | UUUCUGAGAGUUAAGAAAC |
| #39 | 58 | UCAGAAAGCUGGCAAAGAA |
| | 230 | UUCUUUGCCAGCUUUCUGA |
| #40 | 59 | CAGAAAGCUGGCAAAGAAA |
| | 231 | UUUCUUUGCCAGCUUUCUG |
| #41 | 147 | AGAAAGCUGGCAAAGAAAA |
| | 232 | UUUUCUUUGCCAGCUUUCU |
| #42 | 60 | GAAAGCUGGCAAAGAAAAA |
| | 233 | UUUUUCUUUGCCAGCUUUC |
| #43 | 148 | UGGCAAAGAAAAGAUGGU |
| | 234 | ACCAUCUUUUCUUUGCCA |
| #44 | 61 | GCAAAGAAAAGAUGGUAC |
| | 235 | GUACCAUCUUUUUCUUUGC |
| #45 | 62 | CAAAGAAAAGAUGGUACA |
| | 236 | UGUACCAUCUUUUUCUUUG |
| #46 | 149 | AAUCUUUAUCUGACAGUGA |
| | 237 | UCACUGUCAGAUAAAGAUU |

TABLE 2C-continued

| SEQ ID NO: | | Sequence |
|---|---|---|
| #47 | 63 | GUGAAUCUGAUGACAGCAA |
| | 238 | UUGCUGUCAUCAGAUUCAC |
| #48 | 150 | GAAUCUGAUGACAGCAAAU |
| | 239 | AUUUGCUGUCAUCAGAUUC |
| #49 | 151 | GAUGACAGCAAAUCAAAGA |
| | 240 | UCUUUGAUUUGCUGUCAUC |
| #50 | 152 | GACAGCAAAUCAAAGAAGA |
| | 241 | UCUUCUUUGAUUUGCUGUC |
| #51 | 64 | ACAGCAAAUCAAAGAAGAA |
| | 242 | UUCUUCUUUGAUUUGCUGU |
| #52 | 153 | CAGCAAAUCAAAGAAGAAA |
| | 243 | UUUCUUCUUUGAUUUGCUG |
| #53 | 154 | GCAAAUCAAAGAAGAAAAG |
| | 244 | CUUUUCUUCUUUGAUUUGC |
| #54 | 66 | UCAAAGAAGAAAAGAGAUG |
| | 245 | CAUCUCUUUUCUUCUUUGA |
| #55 | 155 | GAAGAAAAGAGAUGCUGCU |
| | 246 | AGCAGCAUCUCUUUUCUUC |
| #56 | 156 | AGAAAAGAGAUGCUGCUGA |
| | 247 | UCAGCAGCAUCUCUUUUCU |

TABLE 2D

| SEQ ID NO: | | Sequence |
|---|---|---|
| #57 | 67 | GAAAAGAGAUGCUGCUGAC |
| | 248 | GUCAGCAGCAUCUCUUUUC |
| #58 | 157 | AAAGAGAUGCUGCUGACAA |
| | 249 | UUGUCAGCAGCAUCUCUUU |
| #59 | 68 | AAGAGAUGCUGCUGACAAA |
| | 250 | UUUGUCAGCAGCAUCUCUU |
| #60 | 69 | GCUGACAAACCAAGAGGAU |
| | 251 | AUCCUCUUGGUUUGUCAGC |
| #61 | 158 | CUGACAAACCAAGAGGAUU |
| | 252 | AAUCCUCUUGGUUUGUCAG |
| #62 | 1 | UGACAAACCAAGAGGAUUU |
| | 253 | AAAUCCUCUUGGUUUGUCA |
| #63 | 159 | ACCAAGAGGAUUUGCCAGA |
| | 254 | UCUGGCAAAUCCUCUUGGU |
| #64 | 160 | AGGAUUUGCCAGAGGUCUU |
| | 255 | AAGACCUCUGGCAAAUCCU |
| #65 | 161 | UGCCAGAGGUCUUGAUCCU |
| | 256 | AGGAUCAAGACCUCUGGCA |
| #66 | 162 | CCAGAGGUCUUGAUCCUGA |
| | 257 | UCAGGAUCAAGACCUCUGG |
| #67 | 163 | AGGUCUUGAUCCUGAAAGA |
| | 258 | UCUUUCAGGAUCAAGACCU |
| #68 | 164 | GUCUUGAUCCUGAAAGAAU |
| | 259 | AUUCUUUCAGGAUCAAGAC |

TABLE 2D-continued

| SEQ ID NO: | | Sequence |
|---|---|---|
| #69 | 165 | UCUUGAUCCUGAAAGAAUA |
| | 260 | UAUUCUUUCAGGAUCAAGA |
| #70 | 166 | CCACAGACAGCAGUGGAGA |
| | 261 | UCUCCACUGCUGUCUGUGG |
| #71 | 167 | CACAGACAGCAGUGGAGAA |
| | 262 | UUCUCCACUGCUGUCUGUG |
| #72 | 168 | ACAGACAGCAGUGGAGAAU |
| | 263 | AUUCUCCACUGCUGUCUGU |
| #73 | 70 | AGACAGCAGUGGAGAAUUG |
| | 264 | CAAUUCUCCACUGCUGUCU |
| #74 | 169 | GUGGAGAAUUGAUGUUUCU |
| | 265 | AGAAACAUCAAUUCUCCAC |
| #75 | 170 | GAGAAUUGAUGUUUCUCAU |
| | 266 | AUGAGAAACAUCAAUUCUC |

TABLE 2E

| SEQ ID NO: | | Sequence |
|---|---|---|
| #76 | 171 | GAAUUGAUGUUUCUCAUGA |
| | 267 | UCAUGAGAAACAUCAAUUC |
| #77 | 71 | CUCAUGAAAUGGAAAGAUU |
| | 268 | AAUCUUUCCAUUUCAUGAG |
| #78 | 172 | CAUGAAAUGGAAAGAUUCA |
| | 269 | UGAAUCUUUCCAUUUCAUG |
| #79 | 173 | UGAAAUGGAAAGAUUCAGA |
| | 270 | UCUGAAUCUUUCCAUUUCA |
| #80 | 174 | GGAAAGAUUCAGAUGAGGC |
| | 271 | GCCUCAUCUGAAUCUUUCC |
| #81 | 175 | GAAAGAUUCAGAUGAGGCA |
| | 272 | UGCCUCAUCUGAAUCUUUC |
| #82 | 176 | AAGAUUCAGAUGAGGCAGA |
| | 273 | UCUGCCUCAUCUGAAUCUU |
| #83 | 72 | CAGACUUGGUGCUGGCGAA |
| | 274 | UUCGCCAGCACCAAGUCUG |
| #84 | 177 | AGACUUGGUGCUGGCGAAA |
| | 275 | UUUCGCCAGCACCAAGUCU |
| #85 | 178 | ACUUGGUGCUGGCGAAAGA |
| | 276 | UCUUUCGCCAGCACCAAGU |
| #86 | 179 | GGUGCUGGCGAAAGAGGCA |
| | 277 | UGCCUCUUUCGCCAGCACC |
| #87 | 180 | UGGCGAAAGAGGCAAAUAU |
| | 278 | AUAUUUGCCUCUUUCGCCA |
| #88 | 73 | GCGAAAGAGGCAAAUAUGA |
| | 279 | UCAUAUUUGCCUCUUUCGC |
| #89 | 74 | CGAAAGAGGCAAAUAUGAA |
| | 280 | UUCAUAUUUGCCUCUUUCG |
| #90 | 181 | AGGCAAAUAUGAAGUGUCC |
| | 281 | GGACACUUCAUAUUUGCCU |

TABLE 2E-continued

| SEQ ID NO: | | Sequence |
|---|---|---|
| #91 | 182 | GCAAAUAUGAAGUGUCCUC |
| | 282 | GAGGACACUUCAUAUUUGC |
| #92 | 183 | AAUAUGAAGUGUCCUCAAA |
| | 283 | UUUGAGGACACUUCAUAUU |
| #93 | 184 | CCUCAAAUUGUAAUUGCUU |
| | 284 | AAGCAAUUACAAUUUGAGG |
| #94 | 185 | AGAGAGACUAACUUGGCAU |
| | 285 | AUGCCAAGUUAGUCUCUCU |

TABLE 2F

| SEQ ID NO: | | Sequence |
|---|---|---|
| #95 | 186 | GAGAGACUAACUUGGCAUU |
| | 286 | AAUGCCAAGUUAGUCUCUC |
| #96 | 187 | GCAUUCUUGUCCAGAAGAU |
| | 287 | AUCUUCUGGACAAGAAUGC |
| #97 | 188 | GUCCAGAAGAUGAAGCUCA |
| | 288 | UGAGCUUCAUCUUCUGGAC |
| #98 | 189 | UCCAGAAGAUGAAGCUCAA |
| | 289 | UUGAGCUUCAUCUUCUGGA |
| #99 | 75 | CAGAAGAUGAAGCUCAAUA |
| | 290 | UAUUGAGCUUCAUCUUCUG |
| #100 | 190 | AGAAGAUGAAGCUCAAUAA |
| | 291 | UUAUUGAGCUUCAUCUUCU |
| #101 | 83 | GAUAAUCCCUUCAAGUUAA |
| | 292 | UUAACUUGAAGGGAUUAUC |
| #102 | 84 | CCAUACAUUUCAAGUGAAA |
| | 293 | UUUCACUUGAAAUGUAUGG |
| #103 | 88 | GACAAAUGCUAGUGUGUUU |
| | 294 | AAACACACUAGCAUUUGUC |
| #104 | 89 | GGGCCAUUCCUUAGCAAAA |
| | 295 | UUUUGCUAAGGAAUGGCCC |
| #105 | 191 | GGUCAUGAUGAAUGGAAUA |
| | 296 | UAUUCCAUUCAUCAUGACC |
| #106 | 95 | CAGCAAAAGCCAGGAAGAA |
| | 297 | UUCUUCCUGGCUUUUGCUG. |

5. The method for treatment according to claim 4, wherein the double-stranded RNAs are selected from #5, #17, #35, #62, #89, #101, #102, #103, #104, #105 and #106 in Tables 2A to 2F.

6. The method for treatment according to claim 4, wherein the double-stranded RNAs are selected from #17, #62 and #89 in Tables 2A to 2F.

7. The method for treatment according to one of claim 4, wherein the siRNAs each comprise two-base overhangs on both ends thereof.

8. The method for treatment according to claim 7, wherein each of the overhangs is on the 3' end of each of the strands forming the double-stranded RNAs.

* * * * *

```
                        SEQUENCE LISTING

<160> NUMBER OF SEQ ID NOS: 297

<210> SEQ ID NO 1
<211> LENGTH: 19
<212> TYPE: RNA
<213> ORGANISM: Artificial
<220> FEATURE:
<223> OTHER INFORMATION: siRNA, sense sequence

<400> SEQUENCE: 1
ugacaaacca agaggauuu                                                19

<210> SEQ ID NO 2
<211> LENGTH: 19
<212> TYPE: RNA
<213> ORGANISM: Artificial
<220> FEATURE:
<223> OTHER INFORMATION: siRNA, sense sequence

<400> SEQUENCE: 2
cccuucggau guggcuuga                                                19

<210> SEQ ID NO 3
<211> LENGTH: 19
<212> TYPE: RNA
<213> ORGANISM: Artificial
<220> FEATURE:
<223> OTHER INFORMATION: siRNA, sense sequence

<400> SEQUENCE: 3
ccuucggaug uggcuugag                                                19
```

```
<210> SEQ ID NO 4
<211> LENGTH: 19
<212> TYPE: RNA
<213> ORGANISM: Artificial
<220> FEATURE:
<223> OTHER INFORMATION: siRNA, sense sequence

<400> SEQUENCE: 4
cuucggaugu ggcuugagc                                                   19

<210> SEQ ID NO 5
<211> LENGTH: 19
<212> TYPE: RNA
<213> ORGANISM: Artificial
<220> FEATURE:
<223> OTHER INFORMATION: siRNA, sense sequence

<400> SEQUENCE: 5
uucggaugug gcuugagcu                                                   19

<210> SEQ ID NO 6
<211> LENGTH: 19
<212> TYPE: RNA
<213> ORGANISM: Artificial
<220> FEATURE:
<223> OTHER INFORMATION: siRNA, sense sequence

<400> SEQUENCE: 6
ucggaugugg cuugagcug                                                   19

<210> SEQ ID NO 7
<211> LENGTH: 19
<212> TYPE: RNA
<213> ORGANISM: Artificial
<220> FEATURE:
<223> OTHER INFORMATION: siRNA, sense sequence

<400> SEQUENCE: 7
cggauguggc uugagcugu                                                   19

<210> SEQ ID NO 8
<211> LENGTH: 19
<212> TYPE: RNA
<213> ORGANISM: Artificial
<220> FEATURE:
<223> OTHER INFORMATION: siRNA, sense sequence

<400> SEQUENCE: 8
ggauguggcu ugagcugua                                                   19

<210> SEQ ID NO 9
<211> LENGTH: 19
<212> TYPE: RNA
<213> ORGANISM: Artificial
<220> FEATURE:
<223> OTHER INFORMATION: siRNA, sense sequence

<400> SEQUENCE: 9
gauguggcuu gagcuguag                                                   19

<210> SEQ ID NO 10
<211> LENGTH: 19
<212> TYPE: RNA
<213> ORGANISM: Artificial
<220> FEATURE:
```

```
<223> OTHER INFORMATION: siRNA, sense sequence

<400> SEQUENCE: 10
auguggcuug agcuguagg                                                    19

<210> SEQ ID NO 11
<211> LENGTH: 19
<212> TYPE: RNA
<213> ORGANISM: Artificial
<220> FEATURE:
<223> OTHER INFORMATION: siRNA, sense sequence

<400> SEQUENCE: 11
uguggcuuga gcuguaggc                                                    19

<210> SEQ ID NO 12
<211> LENGTH: 19
<212> TYPE: RNA
<213> ORGANISM: Artificial
<220> FEATURE:
<223> OTHER INFORMATION: siRNA, sense sequence

<400> SEQUENCE: 12
guggcuugag cuguaggcg                                                    19

<210> SEQ ID NO 13
<211> LENGTH: 19
<212> TYPE: RNA
<213> ORGANISM: Artificial
<220> FEATURE:
<223> OTHER INFORMATION: siRNA, sense sequence

<400> SEQUENCE: 13
uggcuugagc uguaggcgc                                                    19

<210> SEQ ID NO 14
<211> LENGTH: 19
<212> TYPE: RNA
<213> ORGANISM: Artificial
<220> FEATURE:
<223> OTHER INFORMATION: siRNA, sense sequence

<400> SEQUENCE: 14
cagcucggag gcggugaau                                                    19

<210> SEQ ID NO 15
<211> LENGTH: 19
<212> TYPE: RNA
<213> ORGANISM: Artificial
<220> FEATURE:
<223> OTHER INFORMATION: siRNA, sense sequence

<400> SEQUENCE: 15
agcucggagg cggugaaua                                                    19

<210> SEQ ID NO 16
<211> LENGTH: 19
<212> TYPE: RNA
<213> ORGANISM: Artificial
<220> FEATURE:
<223> OTHER INFORMATION: siRNA, sense sequence

<400> SEQUENCE: 16
gcucggaggc ggugaauaa                                                    19
```

```
<210> SEQ ID NO 17
<211> LENGTH: 19
<212> TYPE: RNA
<213> ORGANISM: Artificial
<220> FEATURE:
<223> OTHER INFORMATION: siRNA, sense sequence

<400> SEQUENCE: 17
cucggaggcg gugaauaau                                                    19

<210> SEQ ID NO 18
<211> LENGTH: 19
<212> TYPE: RNA
<213> ORGANISM: Artificial
<220> FEATURE:
<223> OTHER INFORMATION: siRNA, sense sequence

<400> SEQUENCE: 18
auaauagcuc uucaagucu                                                    19

<210> SEQ ID NO 19
<211> LENGTH: 19
<212> TYPE: RNA
<213> ORGANISM: Artificial
<220> FEATURE:
<223> OTHER INFORMATION: siRNA, sense sequence

<400> SEQUENCE: 19
uaauagcucu ucaagucug                                                    19

<210> SEQ ID NO 20
<211> LENGTH: 19
<212> TYPE: RNA
<213> ORGANISM: Artificial
<220> FEATURE:
<223> OTHER INFORMATION: siRNA, sense sequence

<400> SEQUENCE: 20
aauagcucuu caagucugc                                                    19

<210> SEQ ID NO 21
<211> LENGTH: 19
<212> TYPE: RNA
<213> ORGANISM: Artificial
<220> FEATURE:
<223> OTHER INFORMATION: siRNA, sense sequence

<400> SEQUENCE: 21
auagcucuuc aagucugca                                                    19

<210> SEQ ID NO 22
<211> LENGTH: 19
<212> TYPE: RNA
<213> ORGANISM: Artificial
<220> FEATURE:
<223> OTHER INFORMATION: siRNA, sense sequence

<400> SEQUENCE: 22
uagcucuuca agucugcaa                                                    19

<210> SEQ ID NO 23
<211> LENGTH: 19
<212> TYPE: RNA
<213> ORGANISM: Artificial
<220> FEATURE:
<223> OTHER INFORMATION: siRNA, sense sequence
```

```
<400> SEQUENCE: 23
agcucuucaa gucugcaau                                                    19

<210> SEQ ID NO 24
<211> LENGTH: 19
<212> TYPE: RNA
<213> ORGANISM: Artificial
<220> FEATURE:
<223> OTHER INFORMATION: siRNA, sense sequence

<400> SEQUENCE: 24
gcucuucaag ucugcaaua                                                    19

<210> SEQ ID NO 25
<211> LENGTH: 19
<212> TYPE: RNA
<213> ORGANISM: Artificial
<220> FEATURE:
<223> OTHER INFORMATION: siRNA, sense sequence

<400> SEQUENCE: 25
cucuucaagu cugcaauaa                                                    19

<210> SEQ ID NO 26
<211> LENGTH: 19
<212> TYPE: RNA
<213> ORGANISM: Artificial
<220> FEATURE:
<223> OTHER INFORMATION: siRNA, sense sequence

<400> SEQUENCE: 26
ucuucaaguc ugcaauaaa                                                    19

<210> SEQ ID NO 27
<211> LENGTH: 19
<212> TYPE: RNA
<213> ORGANISM: Artificial
<220> FEATURE:
<223> OTHER INFORMATION: siRNA, sense sequence

<400> SEQUENCE: 27
aaaaauggcc uccaacaaa                                                    19

<210> SEQ ID NO 28
<211> LENGTH: 19
<212> TYPE: RNA
<213> ORGANISM: Artificial
<220> FEATURE:
<223> OTHER INFORMATION: siRNA, sense sequence

<400> SEQUENCE: 28
aaaauggccu ccaacaaaa                                                    19

<210> SEQ ID NO 29
<211> LENGTH: 19
<212> TYPE: RNA
<213> ORGANISM: Artificial
<220> FEATURE:
<223> OTHER INFORMATION: siRNA, sense sequence

<400> SEQUENCE: 29
aaauggccuc caacaaaac                                                    19

<210> SEQ ID NO 30
<211> LENGTH: 19
```

```
<212> TYPE: RNA
<213> ORGANISM: Artificial
<220> FEATURE:
<223> OTHER INFORMATION: siRNA, sense sequence

<400> SEQUENCE: 30
aauggccucc aacaaaacu                                              19

<210> SEQ ID NO 31
<211> LENGTH: 19
<212> TYPE: RNA
<213> ORGANISM: Artificial
<220> FEATURE:
<223> OTHER INFORMATION: siRNA, sense sequence

<400> SEQUENCE: 31
auggccucca acaaaacua                                              19

<210> SEQ ID NO 32
<211> LENGTH: 19
<212> TYPE: RNA
<213> ORGANISM: Artificial
<220> FEATURE:
<223> OTHER INFORMATION: siRNA, sense sequence

<400> SEQUENCE: 32
uggccuccaa caaaacuac                                              19

<210> SEQ ID NO 33
<211> LENGTH: 19
<212> TYPE: RNA
<213> ORGANISM: Artificial
<220> FEATURE:
<223> OTHER INFORMATION: siRNA, sense sequence

<400> SEQUENCE: 33
ggccuccaac aaaacuaca                                              19

<210> SEQ ID NO 34
<211> LENGTH: 19
<212> TYPE: RNA
<213> ORGANISM: Artificial
<220> FEATURE:
<223> OTHER INFORMATION: siRNA, sense sequenceRNA

<400> SEQUENCE: 34
gccuccaaca aaacuacau                                              19

<210> SEQ ID NO 35
<211> LENGTH: 19
<212> TYPE: RNA
<213> ORGANISM: Artificial
<220> FEATURE:
<223> OTHER INFORMATION: siRNA, sense sequence

<400> SEQUENCE: 35
ccuccaacaa aacuacauu                                              19

<210> SEQ ID NO 36
<211> LENGTH: 19
<212> TYPE: RNA
<213> ORGANISM: Artificial
<220> FEATURE:
<223> OTHER INFORMATION: siRNA, sense sequence

<400> SEQUENCE: 36
```
cuccaacaaa acuacauug                                           19

<210> SEQ ID NO 37
<211> LENGTH: 19
<212> TYPE: RNA
<213> ORGANISM: Artificial
<220> FEATURE:
<223> OTHER INFORMATION: siRNA, sense sequence

<400> SEQUENCE: 37
uccaacaaaa cuacauugc                                           19

<210> SEQ ID NO 38
<211> LENGTH: 19
<212> TYPE: RNA
<213> ORGANISM: Artificial
<220> FEATURE:
<223> OTHER INFORMATION: siRNA, sense sequence

<400> SEQUENCE: 38
ccaacaaaac uacauugca                                           19

<210> SEQ ID NO 39
<211> LENGTH: 19
<212> TYPE: RNA
<213> ORGANISM: Artificial
<220> FEATURE:
<223> OTHER INFORMATION: siRNA, sense sequence

<400> SEQUENCE: 39
caacaaaacu acauugcaa                                           19

<210> SEQ ID NO 40
<211> LENGTH: 19
<212> TYPE: RNA
<213> ORGANISM: Artificial
<220> FEATURE:
<223> OTHER INFORMATION: siRNA, sense sequence

<400> SEQUENCE: 40
aaacagaaug gaaagagua                                           19

<210> SEQ ID NO 41
<211> LENGTH: 19
<212> TYPE: RNA
<213> ORGANISM: Artificial
<220> FEATURE:
<223> OTHER INFORMATION: siRNA, sense sequence

<400> SEQUENCE: 41
cagaauggaa agaguaaaa                                           19

<210> SEQ ID NO 42
<211> LENGTH: 19
<212> TYPE: RNA
<213> ORGANISM: Artificial
<220> FEATURE:
<223> OTHER INFORMATION: siRNA, sense sequence

<400> SEQUENCE: 42
cagaauggaa agaguaaaa                                           19

<210> SEQ ID NO 43
<211> LENGTH: 19
<212> TYPE: RNA
<213> ORGANISM: Artificial

```
<220> FEATURE:
<223> OTHER INFORMATION: siRNA, sense sequence

<400> SEQUENCE: 43
uugaagaggc agagccuga                                                    19

<210> SEQ ID NO 44
<211> LENGTH: 19
<212> TYPE: RNA
<213> ORGANISM: Artificial
<220> FEATURE:
<223> OTHER INFORMATION: siRNA, sense sequence

<400> SEQUENCE: 44
aggcagagcc ugaagaauu                                                    19

<210> SEQ ID NO 45
<211> LENGTH: 19
<212> TYPE: RNA
<213> ORGANISM: Artificial
<220> FEATURE:
<223> OTHER INFORMATION: siRNA, sense sequence

<400> SEQUENCE: 45
ggcagagccu gaagaauuu                                                    19

<210> SEQ ID NO 46
<211> LENGTH: 19
<212> TYPE: RNA
<213> ORGANISM: Artificial
<220> FEATURE:
<223> OTHER INFORMATION: siRNA, sense sequence

<400> SEQUENCE: 46
cugaagaauu ugucgugga                                                    19

<210> SEQ ID NO 47
<211> LENGTH: 19
<212> TYPE: RNA
<213> ORGANISM: Artificial
<220> FEATURE:
<223> OTHER INFORMATION: siRNA, sense sequence

<400> SEQUENCE: 47
ugaagaauuu gucguggaa                                                    19

<210> SEQ ID NO 48
<211> LENGTH: 19
<212> TYPE: RNA
<213> ORGANISM: Artificial
<220> FEATURE:
<223> OTHER INFORMATION: siRNA, sense sequence

<400> SEQUENCE: 48
aagaauuugu cguggaaaa                                                    19

<210> SEQ ID NO 49
<211> LENGTH: 19
<212> TYPE: RNA
<213> ORGANISM: Artificial
<220> FEATURE:
<223> OTHER INFORMATION: siRNA, sense sequence

<400> SEQUENCE: 49
ggaaaaagua cuagaucga                                                    19
```

```
<210> SEQ ID NO 50
<211> LENGTH: 19
<212> TYPE: RNA
<213> ORGANISM: Artificial
<220> FEATURE:
<223> OTHER INFORMATION: siRNA, sense sequence

<400> SEQUENCE: 50
aguacuagau cgacgugua                                              19

<210> SEQ ID NO 51
<211> LENGTH: 19
<212> TYPE: RNA
<213> ORGANISM: Artificial
<220> FEATURE:
<223> OTHER INFORMATION: siRNA, sense sequence

<400> SEQUENCE: 51
agaucgacgu guagugaau                                              19

<210> SEQ ID NO 52
<211> LENGTH: 19
<212> TYPE: RNA
<213> ORGANISM: Artificial
<220> FEATURE:
<223> OTHER INFORMATION: siRNA, sense sequence

<400> SEQUENCE: 52
acguguagug aaugggaaa                                              19

<210> SEQ ID NO 53
<211> LENGTH: 19
<212> TYPE: RNA
<213> ORGANISM: Artificial
<220> FEATURE:
<223> OTHER INFORMATION: siRNA, sense sequence

<400> SEQUENCE: 53
agugaauggg aaaguggaa                                              19

<210> SEQ ID NO 54
<211> LENGTH: 19
<212> TYPE: RNA
<213> ORGANISM: Artificial
<220> FEATURE:
<223> OTHER INFORMATION: siRNA, sense sequence

<400> SEQUENCE: 54
ugaaugggaa aguggaaua                                              19

<210> SEQ ID NO 55
<211> LENGTH: 19
<212> TYPE: RNA
<213> ORGANISM: Artificial
<220> FEATURE:
<223> OTHER INFORMATION: siRNA, sense sequence

<400> SEQUENCE: 55
cuugggaacc ugaagaaaa                                              19

<210> SEQ ID NO 56
<211> LENGTH: 19
<212> TYPE: RNA
<213> ORGANISM: Artificial
<220> FEATURE:
<223> OTHER INFORMATION: siRNA, sense sequence
```

```
<400> SEQUENCE: 56
cagaauugau ugaagcguu                                              19

<210> SEQ ID NO 57
<211> LENGTH: 19
<212> TYPE: RNA
<213> ORGANISM: Artificial
<220> FEATURE:
<223> OTHER INFORMATION: siRNA, sense sequence

<400> SEQUENCE: 57
agaauugauu gaagcguuu                                              19

<210> SEQ ID NO 58
<211> LENGTH: 19
<212> TYPE: RNA
<213> ORGANISM: Artificial
<220> FEATURE:
<223> OTHER INFORMATION: siRNA, sense sequence

<400> SEQUENCE: 58
ucagaaagcu ggcaaagaa                                              19

<210> SEQ ID NO 59
<211> LENGTH: 19
<212> TYPE: RNA
<213> ORGANISM: Artificial
<220> FEATURE:
<223> OTHER INFORMATION: siRNA, sense sequence

<400> SEQUENCE: 59
cagaaagcug gcaaagaaa                                              19

<210> SEQ ID NO 60
<211> LENGTH: 19
<212> TYPE: RNA
<213> ORGANISM: Artificial
<220> FEATURE:
<223> OTHER INFORMATION: siRNA, sense sequence

<400> SEQUENCE: 60
gaaagcuggc aaagaaaaa                                              19

<210> SEQ ID NO 61
<211> LENGTH: 19
<212> TYPE: RNA
<213> ORGANISM: Artificial
<220> FEATURE:
<223> OTHER INFORMATION: siRNA, sense sequence

<400> SEQUENCE: 61
gcaaagaaaa agaugguac                                              19

<210> SEQ ID NO 62
<211> LENGTH: 19
<212> TYPE: RNA
<213> ORGANISM: Artificial
<220> FEATURE:
<223> OTHER INFORMATION: siRNA, sense sequence

<400> SEQUENCE: 62
caaagaaaaa gaugguaca                                              19

<210> SEQ ID NO 63
```

```
<211> LENGTH: 19
<212> TYPE: RNA
<213> ORGANISM: Artificial
<220> FEATURE:
<223> OTHER INFORMATION: siRNA, sense sequence

<400> SEQUENCE: 63
gugaaucuga ugacagcaa                                                    19

<210> SEQ ID NO 64
<211> LENGTH: 19
<212> TYPE: RNA
<213> ORGANISM: Artificial
<220> FEATURE:
<223> OTHER INFORMATION: siRNA, sense sequence

<400> SEQUENCE: 64
acagcaaauc aaagaagaa                                                    19

<210> SEQ ID NO 65
<211> LENGTH: 19
<212> TYPE: RNA
<213> ORGANISM: Artificial
<220> FEATURE:
<223> OTHER INFORMATION: siRNA, sense sequence

<400> SEQUENCE: 65
acagcaaauc aaagaagaa                                                    19

<210> SEQ ID NO 66
<211> LENGTH: 19
<212> TYPE: RNA
<213> ORGANISM: Artificial
<220> FEATURE:
<223> OTHER INFORMATION: siRNA, sense sequence

<400> SEQUENCE: 66
ucaaagaaga aaagagaug                                                    19

<210> SEQ ID NO 67
<211> LENGTH: 19
<212> TYPE: RNA
<213> ORGANISM: Artificial
<220> FEATURE:
<223> OTHER INFORMATION: siRNA, sense sequence

<400> SEQUENCE: 67
gaaaagagau gcugcugac                                                    19

<210> SEQ ID NO 68
<211> LENGTH: 19
<212> TYPE: RNA
<213> ORGANISM: Artificial
<220> FEATURE:
<223> OTHER INFORMATION: siRNA, sense sequence

<400> SEQUENCE: 68
aagagaugcu gcugacaaa                                                    19

<210> SEQ ID NO 69
<211> LENGTH: 19
<212> TYPE: RNA
<213> ORGANISM: Artificial
<220> FEATURE:
<223> OTHER INFORMATION: siRNA, sense sequence

<400> SEQUENCE: 69
```

-continued

| | |
|---|---|
| gcugacaaac caagaggau | 19 |

<210> SEQ ID NO 70
<211> LENGTH: 19
<212> TYPE: RNA
<213> ORGANISM: Artificial
<220> FEATURE:
<223> OTHER INFORMATION: siRNA, sense sequence

<400> SEQUENCE: 70

| | |
|---|---|
| agacagcagu ggagaauug | 19 |

<210> SEQ ID NO 71
<211> LENGTH: 19
<212> TYPE: RNA
<213> ORGANISM: Artificial
<220> FEATURE:
<223> OTHER INFORMATION: siRNA, sense sequence

<400> SEQUENCE: 71

| | |
|---|---|
| cucaugaaau ggaaagauu | 19 |

<210> SEQ ID NO 72
<211> LENGTH: 19
<212> TYPE: RNA
<213> ORGANISM: Artificial
<220> FEATURE:
<223> OTHER INFORMATION: siRNA, sense sequence

<400> SEQUENCE: 72

| | |
|---|---|
| cagacuuggu gcuggcgaa | 19 |

<210> SEQ ID NO 73
<211> LENGTH: 19
<212> TYPE: RNA
<213> ORGANISM: Artificial
<220> FEATURE:
<223> OTHER INFORMATION: siRNA, sense sequence

<400> SEQUENCE: 73

| | |
|---|---|
| gcgaaagagg caaauauga | 19 |

<210> SEQ ID NO 74
<211> LENGTH: 19
<212> TYPE: RNA
<213> ORGANISM: Artificial
<220> FEATURE:
<223> OTHER INFORMATION: siRNA, sense sequence

<400> SEQUENCE: 74

| | |
|---|---|
| cgaaagaggc aaauaugaa | 19 |

<210> SEQ ID NO 75
<211> LENGTH: 19
<212> TYPE: RNA
<213> ORGANISM: Artificial
<220> FEATURE:
<223> OTHER INFORMATION: siRNA, sense sequence

<400> SEQUENCE: 75

| | |
|---|---|
| cagaagauga agcucaaua | 19 |

<210> SEQ ID NO 76
<211> LENGTH: 19
<212> TYPE: RNA

```
<213> ORGANISM: Artificial
<220> FEATURE:
<223> OTHER INFORMATION: siRNA, sense sequence

<400> SEQUENCE: 76
ugaaaguagc guuggaaga                                                    19

<210> SEQ ID NO 77
<211> LENGTH: 19
<212> TYPE: RNA
<213> ORGANISM: Artificial
<220> FEATURE:
<223> OTHER INFORMATION: siRNA, sense sequence

<400> SEQUENCE: 77
cauuugauac caugguaua                                                    19

<210> SEQ ID NO 78
<211> LENGTH: 19
<212> TYPE: RNA
<213> ORGANISM: Artificial
<220> FEATURE:
<223> OTHER INFORMATION: siRNA, sense sequence

<400> SEQUENCE: 78
gggaaauguc cauagucau                                                    19

<210> SEQ ID NO 79
<211> LENGTH: 19
<212> TYPE: RNA
<213> ORGANISM: Artificial
<220> FEATURE:
<223> OTHER INFORMATION: siRNA, sense sequence

<400> SEQUENCE: 79
ggaaaugucc auagucauu                                                    19

<210> SEQ ID NO 80
<211> LENGTH: 19
<212> TYPE: RNA
<213> ORGANISM: Artificial
<220> FEATURE:
<223> OTHER INFORMATION: siRNA, sense sequence

<400> SEQUENCE: 80
agucaaaacu uguguucuc                                                    19

<210> SEQ ID NO 81
<211> LENGTH: 19
<212> TYPE: RNA
<213> ORGANISM: Artificial
<220> FEATURE:
<223> OTHER INFORMATION: siRNA, sense sequence

<400> SEQUENCE: 81
gccauuauuc caagcaaaa                                                    19

<210> SEQ ID NO 82
<211> LENGTH: 19
<212> TYPE: RNA
<213> ORGANISM: Artificial
<220> FEATURE:
<223> OTHER INFORMATION: siRNA, sense sequence

<400> SEQUENCE: 82
agauaauccc uucaaguua                                                    19
```

<210> SEQ ID NO 83
<211> LENGTH: 19
<212> TYPE: RNA
<213> ORGANISM: Artificial
<220> FEATURE:
<223> OTHER INFORMATION: siRNA, sense sequence

<400> SEQUENCE: 83
gauaaucccu ucaaguuaa                                              19

<210> SEQ ID NO 84
<211> LENGTH: 19
<212> TYPE: RNA
<213> ORGANISM: Artificial
<220> FEATURE:
<223> OTHER INFORMATION: siRNA, sense sequence

<400> SEQUENCE: 84
ccauacauuu caagugaaa                                              19

<210> SEQ ID NO 85
<211> LENGTH: 19
<212> TYPE: RNA
<213> ORGANISM: Artificial
<220> FEATURE:
<223> OTHER INFORMATION: siRNA, sense sequence

<400> SEQUENCE: 85
gcaaaauucc uaaaggaa                                               19

<210> SEQ ID NO 86
<211> LENGTH: 19
<212> TYPE: RNA
<213> ORGANISM: Artificial
<220> FEATURE:
<223> OTHER INFORMATION: siRNA, sense sequence

<400> SEQUENCE: 86
gaugaggaaa cuagacaaa                                              19

<210> SEQ ID NO 87
<211> LENGTH: 19
<212> TYPE: RNA
<213> ORGANISM: Artificial
<220> FEATURE:
<223> OTHER INFORMATION: siRNA, sense sequence

<400> SEQUENCE: 87
ggaaacuaga caaaugcua                                              19

<210> SEQ ID NO 88
<211> LENGTH: 19
<212> TYPE: RNA
<213> ORGANISM: Artificial
<220> FEATURE:
<223> OTHER INFORMATION: siRNA, sense sequence

<400> SEQUENCE: 88
gacaaaugcu aguguguuu                                              19

<210> SEQ ID NO 89
<211> LENGTH: 19
<212> TYPE: RNA
<213> ORGANISM: Artificial
<220> FEATURE:

<223> OTHER INFORMATION: siRNA, sense sequence

<400> SEQUENCE: 89
gggccauucc uuagcaaaa                                                      19

<210> SEQ ID NO 90
<211> LENGTH: 19
<212> TYPE: RNA
<213> ORGANISM: Artificial
<220> FEATURE:
<223> OTHER INFORMATION: siRNA, sense sequence

<400> SEQUENCE: 90
aaaccuaauc agaugguua                                                      19

<210> SEQ ID NO 91
<211> LENGTH: 19
<212> TYPE: RNA
<213> ORGANISM: Artificial
<220> FEATURE:
<223> OTHER INFORMATION: siRNA, sense sequence

<400> SEQUENCE: 91
ucagaugguu agagguguu                                                      19

<210> SEQ ID NO 92
<211> LENGTH: 19
<212> TYPE: RNA
<213> ORGANISM: Artificial
<220> FEATURE:
<223> OTHER INFORMATION: siRNA, sense sequence

<400> SEQUENCE: 92
gguuagaggu guuggcagu                                                      19

<210> SEQ ID NO 93
<211> LENGTH: 19
<212> TYPE: RNA
<213> ORGANISM: Artificial
<220> FEATURE:
<223> OTHER INFORMATION: siRNA, sense sequence

<400> SEQUENCE: 93
gucauaaaug ugugaacaa                                                      19

<210> SEQ ID NO 94
<211> LENGTH: 19
<212> TYPE: RNA
<213> ORGANISM: Artificial
<220> FEATURE:
<223> OTHER INFORMATION: siRNA, sense sequence

<400> SEQUENCE: 94
cuuuacuggu ucagcaaaa                                                      19

<210> SEQ ID NO 95
<211> LENGTH: 19
<212> TYPE: RNA
<213> ORGANISM: Artificial
<220> FEATURE:
<223> OTHER INFORMATION: siRNA, sense sequence

<400> SEQUENCE: 95
cagcaaaagc caggaagaa                                                      19

```
<210> SEQ ID NO 96
<211> LENGTH: 19
<212> TYPE: RNA
<213> ORGANISM: Artificial
<220> FEATURE:
<223> OTHER INFORMATION: siRNA, sense sequence

<400> SEQUENCE: 96
gcaaaagcca ggaagaaca                                          19

<210> SEQ ID NO 97
<211> LENGTH: 19
<212> TYPE: RNA
<213> ORGANISM: Artificial
<220> FEATURE:
<223> OTHER INFORMATION: siRNA, sense sequence

<400> SEQUENCE: 97
uguaaauacu ggugaacag                                          19

<210> SEQ ID NO 98
<211> LENGTH: 15
<212> TYPE: DNA
<213> ORGANISM: Artificial
<220> FEATURE:
<223> OTHER INFORMATION: antisense

<400> SEQUENCE: 98
ctgttttttt cccat                                              15

<210> SEQ ID NO 99
<211> LENGTH: 16
<212> TYPE: DNA
<213> ORGANISM: Artificial
<220> FEATURE:
<223> OTHER INFORMATION: antisense

<400> SEQUENCE: 99 tctgttttttt tcccat                                            16

<210> SEQ ID NO 100
<211> LENGTH: 17
<212> TYPE: DNA
<213> ORGANISM: Artificial
<220> FEATURE:
<223> OTHER INFORMATION: antisense

<400> SEQUENCE: 100
ttctgttttt ttcccat                                            17

<210> SEQ ID NO 101
<211> LENGTH: 18
<212> TYPE: DNA
<213> ORGANISM: Artificial
<220> FEATURE:
<223> OTHER INFORMATION: antisense

<400> SEQUENCE: 101 attctgttttt tttcccat                                          18

<210> SEQ ID NO 102
<211> LENGTH: 19
<212> TYPE: DNA
<213> ORGANISM: Artificial
<220> FEATURE:
<223> OTHER INFORMATION: antisense
```

```
<400> SEQUENCE: 102
cattctgttt ttttcccat                                                    19

<210> SEQ ID NO 103
<211> LENGTH: 20
<212> TYPE: DNA
<213> ORGANISM: Artificial
<220> FEATURE:
<223> OTHER INFORMATION: antisense

<400> SEQUENCE: 103
ccattctgtt tttttcccat                                                   20

<210> SEQ ID NO 104
<211> LENGTH: 21
<212> TYPE: DNA
<213> ORGANISM: Artificial
<220> FEATURE:
<223> OTHER INFORMATION: antisense

<400> SEQUENCE: 104
tccattctgt tttttttccca t                                                21

<210> SEQ ID NO 105
<211> LENGTH: 21
<212> TYPE: DNA
<213> ORGANISM: Artificial
<220> FEATURE:
<223> OTHER INFORMATION: antisense

<400> SEQUENCE: 105
tccattctgt tttttttccca t                                                21

<210> SEQ ID NO 106
<211> LENGTH: 22
<212> TYPE: DNA
<213> ORGANISM: Artificial
<220> FEATURE:
<223> OTHER INFORMATION: antisense

<400> SEQUENCE: 106
ttccattctg tttttttccc at                                                22

<210> SEQ ID NO 107
<211> LENGTH: 23
<212> TYPE: DNA
<213> ORGANISM: Artificial
<220> FEATURE:
<223> OTHER INFORMATION: antisense

<400> SEQUENCE: 107
tttccattct gtttttttcc cat                                               23

<210> SEQ ID NO 108
<211> LENGTH: 24
<212> TYPE: DNA
<213> ORGANISM: Artificial
<220> FEATURE:
<223> OTHER INFORMATION: antisense

<400> SEQUENCE: 108
ctttccattc tgtttttttc ccat                                              24

<210> SEQ ID NO 109
<211> LENGTH: 25
```

<212> TYPE: DNA
<213> ORGANISM: Artificial
<220> FEATURE:
<223> OTHER INFORMATION: antisense

<400> SEQUENCE: 109
tctttccatt ctgtttttt cccat                                         25

<210> SEQ ID NO 110
<211> LENGTH: 26
<212> TYPE: DNA
<213> ORGANISM: Artificial
<220> FEATURE:
<223> OTHER INFORMATION: antisense

<400> SEQUENCE: 110
ctctttccat tctgtttttt tcccat                                        26

<210> SEQ ID NO 111
<211> LENGTH: 27
<212> TYPE: DNA
<213> ORGANISM: Artificial
<220> FEATURE:
<223> OTHER INFORMATION: antisense

<400> SEQUENCE: 111
actctttcca ttctgttttt ttcccat                                       27

<210> SEQ ID NO 112
<211> LENGTH: 28
<212> TYPE: DNA
<213> ORGANISM: Artificial
<220> FEATURE:
<223> OTHER INFORMATION: antisense

<400> SEQUENCE: 112
tactctttcc attctgtttt tttcccat                                      28

<210> SEQ ID NO 113
<211> LENGTH: 29
<212> TYPE: DNA
<213> ORGANISM: Artificial
<220> FEATURE:
<223> OTHER INFORMATION: antisense

<400> SEQUENCE: 113
ttactctttc cattctgttt ttttcccat                                     29

<210> SEQ ID NO 114
<211> LENGTH: 21
<212> TYPE: DNA
<213> ORGANISM: Artificial
<220> FEATURE:
<223> OTHER INFORMATION: siRNA

<400> SEQUENCE: 114
gggagaaauc agaaggaaat t                                             21

<210> SEQ ID NO 115
<211> LENGTH: 21
<212> TYPE: DNA
<213> ORGANISM: Artificial
<220> FEATURE:
<223> OTHER INFORMATION: siRNA

<400> SEQUENCE: 115
gcgaagagcu aaaggaggat t                                              21

<210> SEQ ID NO 116
<211> LENGTH: 21
<212> TYPE: DNA
<213> ORGANISM: Artificial
<220> FEATURE:
<223> OTHER INFORMATION: siRNA

<400> SEQUENCE: 116
ggauacaguc ugagaguuat t                                              21

<210> SEQ ID NO 117
<211> LENGTH: 21
<212> TYPE: DNA
<213> ORGANISM: Artificial
<220> FEATURE:
<223> OTHER INFORMATION: siRNA

<400> SEQUENCE: 117
gguacuagaa gaagaggaat t                                              21

<210> SEQ ID NO 118
<211> LENGTH: 21
<212> TYPE: DNA
<213> ORGANISM: Artificial
<220> FEATURE:
<223> OTHER INFORMATION: siRNA

<400> SEQUENCE: 118
ggcgaguugu caagggcaat t                                              21

<210> SEQ ID NO 119
<211> LENGTH: 21
<212> TYPE: DNA
<213> ORGANISM: Artificial
<220> FEATURE:
<223> OTHER INFORMATION: siRNA

<400> SEQUENCE: 119
gaaaacagcu caugagacat t                                              21

<210> SEQ ID NO 120
<211> LENGTH: 21
<212> TYPE: DNA
<213> ORGANISM: Artificial
<220> FEATURE:
<223> OTHER INFORMATION: siRNA

<400> SEQUENCE: 120
ggaccgucgu guagugaaut t                                              21

<210> SEQ ID NO 121
<211> LENGTH: 21
<212> TYPE: DNA
<213> ORGANISM: Artificial
<220> FEATURE:
<223> OTHER INFORMATION: siRNA

<400> SEQUENCE: 121
ccgacuuggu gcuggcaaat t                                              21

<210> SEQ ID NO 122
<211> LENGTH: 21
<212> TYPE: DNA
<213> ORGANISM: Artificial

```
<220> FEATURE:
<223> OTHER INFORMATION: siRNA

<400> SEQUENCE: 122
ggaaaaugga auuagacuat t                                              21

<210> SEQ ID NO 123
<211> LENGTH: 21
<212> TYPE: DNA
<213> ORGANISM: Artificial
<220> FEATURE:
<223> OTHER INFORMATION: siRNA

<400> SEQUENCE: 123
auccgcgcga uaguacguat t                                              21

<210> SEQ ID NO 124
<211> LENGTH: 21
<212> TYPE: DNA
<213> ORGANISM: Artificial
<220> FEATURE:
<223> OTHER INFORMATION: siRNA

<400> SEQUENCE: 124
ugacaaacca agaggauuut t                                              21

<210> SEQ ID NO 125
<211> LENGTH: 1851
<212> TYPE: DNA
<213> ORGANISM: Homo sapiens
<220> FEATURE:
<221> NAME/KEY: CDS
<222> LOCATION: (152)..(703)
<223> OTHER INFORMATION:

<400> SEQUENCE: 125 tcccccggc ggccccgcgc gcagctcccg gctccctccc ccttcggatg tggcttgagc      60
tgtaggcgcg gagggccgga gacgctgcag acccgcgacc cggagcagct cggaggcggt    120
gaataatagc tcttcaagtc tgcaataaaa a atg gcc tcc aac aaa act aca       172
                                   Met Ala Ser Asn Lys Thr Thr
                                    1               5 ttg caa aaa atg gga aaa aaa cag aat gga aag agt aaa aaa gtt gaa      220
Leu Gln Lys Met Gly Lys Lys Gln Asn Gly Lys Ser Lys Lys Val Glu
         10                  15                  20 gag gca gag cct gaa gaa ttt gtc gtg gaa aaa gta cta gat cga cgt      268
Glu Ala Glu Pro Glu Glu Phe Val Val Glu Lys Val Leu Asp Arg Arg
 25                  30                  35 gta gtg aat ggg aaa gtg gaa tat ttc ctg aag tgg aag gga ttt aca      316
Val Val Asn Gly Lys Val Glu Tyr Phe Leu Lys Trp Lys Gly Phe Thr
 40                  45                  50                  55 gat gct gac aat act tgg gaa cct gaa gaa aat tta gat tgt cca gaa      364
Asp Ala Asp Asn Thr Trp Glu Pro Glu Glu Asn Leu Asp Cys Pro Glu
             60                  65                  70 ttg att gaa gcg ttt ctt aac tct cag aaa gct ggc aaa gaa aaa gat      412
Leu Ile Glu Ala Phe Leu Asn Ser Gln Lys Ala Gly Lys Glu Lys Asp
         75                  80                  85 ggt aca aaa aga aaa tct tta tct gac agt gaa tct gat gac agc aaa      460
Gly Thr Lys Arg Lys Ser Leu Ser Asp Ser Glu Ser Asp Asp Ser Lys
     90                  95                 100 tca aag aag aaa aga gat gct gct gac aaa cca aga gga ttt gcc aga     508
Ser Lys Lys Lys Arg Asp Ala Ala Asp Lys Pro Arg Gly Phe Ala Arg
105                 110                 115
```

```
ggt ctt gat cct gaa aga ata att ggt gcc aca gac agc agt gga gaa      556
Gly Leu Asp Pro Glu Arg Ile Ile Gly Ala Thr Asp Ser Ser Gly Glu
120                 125                 130                 135 ttg atg ttt ctc atg aaa tgg aaa gat tca gat gag gca gac ttg gtg      604
Leu Met Phe Leu Met Lys Trp Lys Asp Ser Asp Glu Ala Asp Leu Val
                140                 145                 150 ctg gcg aaa gag gca aat atg aag tgt cct caa att gta att gct ttt      652
Leu Ala Lys Glu Ala Asn Met Lys Cys Pro Gln Ile Val Ile Ala Phe
            155                 160                 165 tat gaa gag aga cta act tgg cat tct tgt cca gaa gat gaa gct caa      700
Tyr Glu Glu Arg Leu Thr Trp His Ser Cys Pro Glu Asp Glu Ala Gln
        170                 175                 180 taa ttgttcacat tgttctttta tatatattta tatatatata taaaaattgg           753
gtcttagatt ttgatttact agtgtgacaa ataactaca tcctaatgaa atcaagttt      813 gatatgtttg ttttgaaagt agcgttggaa gagttgttgg gggttttttg catccatagc    873
actggttact ttgaacaaat aaataaaagc tttctgtagt tgcttccttt atcagaaaag    933
aacatttgat accatggtat atcatttcct cttcattaaa gaacagcttt tctaaatgtt    993 ggggaaatg tccatagtca ttactcagtc aaaacttgtg ttctcatgag cctaaggacc    1053
attctagatt tattacgtgt ttttttgtgt gtgtgtgtg tgtgtgtgtg tgtgtatcca    1113
taaaatgcat atgtaaattt ttttttgttt ttaagcattc acccaaacaa aaaaatcaca    1173
ggtaaaccca tgtttctgag atgccattat tccaagcaaa ataagagata atcccttcaa    1233
gttaaattga aaattttcct gaaaccatac atttcaagtg aaataagtaa ttctagatag    1293
gacaatttaa attggataat tttaaagtgt ctataattgc agtggtttat ttgcaaaatt    1353
cctaaaagga aaatttttat cactgccatc acagcaggtt tcctcatcca gatgaggaaa    1413
ctagacaaat gctagtgtgt tttaactagc taaacaaaac taagttaaat gaacatttaa    1473
aagtttccct agcgggccat tccttagcaa aatgttggaa tccctgttgc tacattgact    1533
aaaaggtcat gatgaatgga atatgtaaga cttggctcat agaaacctaa tcagatggtt    1593
agaggtgttg gcagtttagg acctgctgtc ataaatgtgt gaacaacctt ttgtaaccta    1653
acctattgac ctgcatgttt tttctttacc ccaattcatt acatggaggc tcaatcttga    1713
gtttgcttta ctggttcagc aaaagccagg aagaacaact ttgtagtaat caaaatgtta    1773
tccaactgta tattgtttac tttattgtaa atactggtga acagtggtta ataaatagtt    1833
ttatattcct ttatgcaa                                                  1851

<210> SEQ ID NO 126
<211> LENGTH: 183
<212> TYPE: PRT
<213> ORGANISM: Homo sapiens

<400> SEQUENCE: 126

Met Ala Ser Asn Lys Thr Thr Leu Gln Lys Met Gly Lys Lys Gln Asn
1               5                   10                  15

Gly Lys Ser Lys Lys Val Glu Glu Ala Glu Pro Glu Glu Phe Val Val
                20                  25                  30

Glu Lys Val Leu Asp Arg Arg Val Val Asn Gly Lys Val Glu Tyr Phe
            35                  40                  45

Leu Lys Trp Lys Gly Phe Thr Asp Ala Asp Asn Thr Trp Glu Pro Glu
        50                  55                  60

Glu Asn Leu Asp Cys Pro Glu Leu Ile Glu Ala Phe Leu Asn Ser Gln
65                  70                  75                  80
```

```
Lys Ala Gly Lys Glu Lys Asp Gly Thr Lys Arg Lys Ser Leu Ser Asp
                 85                  90                  95

Ser Glu Ser Asp Asp Ser Lys Ser Lys Lys Arg Asp Ala Ala Asp
            100                 105                 110

Lys Pro Arg Gly Phe Ala Arg Gly Leu Asp Pro Glu Arg Ile Ile Gly
            115                 120                 125

Ala Thr Asp Ser Ser Gly Glu Leu Met Phe Leu Met Lys Trp Lys Asp
        130                 135                 140

Ser Asp Glu Ala Asp Leu Val Leu Ala Lys Glu Ala Asn Met Lys Cys
145                 150                 155                 160

Pro Gln Ile Val Ile Ala Phe Tyr Glu Glu Arg Leu Thr Trp His Ser
                165                 170                 175

Cys Pro Glu Asp Glu Ala Gln
            180

<210> SEQ ID NO 127
<211> LENGTH: 19
<212> TYPE: RNA
<213> ORGANISM: Artificial
<220> FEATURE:
<223> OTHER INFORMATION: siRNA, sense sequence

<400> SEQUENCE: 127
aaaacagaau ggaaagagu                                                      19

<210> SEQ ID NO 128
<211> LENGTH: 19
<212> TYPE: RNA
<213> ORGANISM: Artificial
<220> FEATURE:
<223> OTHER INFORMATION: siRNA, sense sequence

<400> SEQUENCE: 128
aacagaaugg aaagaguaa                                                      19

<210> SEQ ID NO 129
<211> LENGTH: 19
<212> TYPE: RNA
<213> ORGANISM: Artificial
<220> FEATURE:
<223> OTHER INFORMATION: siRNA, sense sequence

<400> SEQUENCE: 129
aaaaaguuga agaggcaga                                                      19

<210> SEQ ID NO 130
<211> LENGTH: 19
<212> TYPE: RNA
<213> ORGANISM: Artificial
<220> FEATURE:
<223> OTHER INFORMATION: siRNA, sense sequence

<400> SEQUENCE: 130
aguugaagag gcagagccu                                                      19

<210> SEQ ID NO 131
<211> LENGTH: 19
<212> TYPE: RNA
<213> ORGANISM: Artificial
<220> FEATURE:
<223> OTHER INFORMATION: siRNA, sense sequence

<400> SEQUENCE: 131
```

| | | |
|---|---|---|
| agaauuuguc guggaaaaa | | 19 |

<210> SEQ ID NO 132
<211> LENGTH: 19
<212> TYPE: RNA
<213> ORGANISM: Artificial
<220> FEATURE:
<223> OTHER INFORMATION: siRNA, sense sequence

<400> SEQUENCE: 132

| | | |
|---|---|---|
| ugucguggaa aaaguacua | | 19 |

<210> SEQ ID NO 133
<211> LENGTH: 19
<212> TYPE: RNA
<213> ORGANISM: Artificial
<220> FEATURE:
<223> OTHER INFORMATION: siRNA, sense sequence

<400> SEQUENCE: 133

| | | |
|---|---|---|
| uggaaaagu acuagaucg | | 19 |

<210> SEQ ID NO 134
<211> LENGTH: 19
<212> TYPE: RNA
<213> ORGANISM: Artificial
<220> FEATURE:
<223> OTHER INFORMATION: siRNA, sense sequence

<400> SEQUENCE: 134

| | | |
|---|---|---|
| gacguguagu gaaugggaa | | 19 |

<210> SEQ ID NO 135
<211> LENGTH: 19
<212> TYPE: RNA
<213> ORGANISM: Artificial
<220> FEATURE:
<223> OTHER INFORMATION: siRNA, sense sequence

<400> SEQUENCE: 135

| | | |
|---|---|---|
| gugaauggga aaguggaau | | 19 |

<210> SEQ ID NO 136
<211> LENGTH: 19
<212> TYPE: RNA
<213> ORGANISM: Artificial
<220> FEATURE:
<223> OTHER INFORMATION: siRNA, sense sequence

<400> SEQUENCE: 136

| | | |
|---|---|---|
| uuccugaagu ggaagggau | | 19 |

<210> SEQ ID NO 137
<211> LENGTH: 19
<212> TYPE: RNA
<213> ORGANISM: Artificial
<220> FEATURE:
<223> OTHER INFORMATION: siRNA, sense sequence

<400> SEQUENCE: 137

| | | |
|---|---|---|
| uccugaagug gaagggauu | | 19 |

<210> SEQ ID NO 138
<211> LENGTH: 19
<212> TYPE: RNA
<213> ORGANISM: Artificial

```
<220> FEATURE:
<223> OTHER INFORMATION: siRNA, sense sequence

<400> SEQUENCE: 138
cugaagugga agggauuua                                                    19

<210> SEQ ID NO 139
<211> LENGTH: 19
<212> TYPE: RNA
<213> ORGANISM: Artificial
<220> FEATURE:
<223> OTHER INFORMATION: siRNA, sense sequence

<400> SEQUENCE: 139
guggaaggga uuuacagau                                                    19

<210> SEQ ID NO 140
<211> LENGTH: 19
<212> TYPE: RNA
<213> ORGANISM: Artificial
<220> FEATURE:
<223> OTHER INFORMATION: siRNA, sense sequence

<400> SEQUENCE: 140
uggaagggau uuacagaug                                                    19

<210> SEQ ID NO 141
<211> LENGTH: 19
<212> TYPE: RNA
<213> ORGANISM: Artificial
<220> FEATURE:
<223> OTHER INFORMATION: siRNA, sense sequence

<400> SEQUENCE: 141
auuuacagau gcugacaau                                                    19

<210> SEQ ID NO 142
<211> LENGTH: 19
<212> TYPE: RNA
<213> ORGANISM: Artificial
<220> FEATURE:
<223> OTHER INFORMATION: siRNA, sense sequence

<400> SEQUENCE: 142
gcugacaaua cuugggaac                                                    19

<210> SEQ ID NO 143
<211> LENGTH: 19
<212> TYPE: RNA
<213> ORGANISM: Artificial
<220> FEATURE:
<223> OTHER INFORMATION: siRNA, sense sequence

<400> SEQUENCE: 143
ugacaauacu ugggaaccu                                                    19

<210> SEQ ID NO 144
<211> LENGTH: 19
<212> TYPE: RNA
<213> ORGANISM: Artificial
<220> FEATURE:
<223> OTHER INFORMATION: siRNA, sense sequence

<400> SEQUENCE: 144
uugggaaccu gaagaaaau                                                    19
```

<210> SEQ ID NO 145
<211> LENGTH: 19
<212> TYPE: RNA
<213> ORGANISM: Artificial
<220> FEATURE:
<223> OTHER INFORMATION: siRNA, sense sequence

<400> SEQUENCE: 145
ugauugaagc guuucuuaa                                               19

<210> SEQ ID NO 146
<211> LENGTH: 19
<212> TYPE: RNA
<213> ORGANISM: Artificial
<220> FEATURE:
<223> OTHER INFORMATION: siRNA, sense sequence

<400> SEQUENCE: 146
guuucuuaac ucucagaaa                                               19

<210> SEQ ID NO 147
<211> LENGTH: 19
<212> TYPE: RNA
<213> ORGANISM: Artificial
<220> FEATURE:
<223> OTHER INFORMATION: siRNA, sense sequence

<400> SEQUENCE: 147
agaaagcugg caaagaaaa                                               19

<210> SEQ ID NO 148
<211> LENGTH: 19
<212> TYPE: RNA
<213> ORGANISM: Artificial
<220> FEATURE:
<223> OTHER INFORMATION: siRNA, sense sequence

<400> SEQUENCE: 148
uggcaaagaa aaagauggu                                               19

<210> SEQ ID NO 149
<211> LENGTH: 19
<212> TYPE: RNA
<213> ORGANISM: Artificial
<220> FEATURE:
<223> OTHER INFORMATION: siRNA, sense sequence

<400> SEQUENCE: 149
aaucuuuauc ugacaguga                                               19

<210> SEQ ID NO 150
<211> LENGTH: 19
<212> TYPE: RNA
<213> ORGANISM: Artificial
<220> FEATURE:
<223> OTHER INFORMATION: siRNA, sense sequence

<400> SEQUENCE: 150
gaaucugaug acagcaaau                                               19

<210> SEQ ID NO 151
<211> LENGTH: 19
<212> TYPE: RNA
<213> ORGANISM: Artificial
<220> FEATURE:
<223> OTHER INFORMATION: siRNA, sense sequence

```
<400> SEQUENCE: 151
gaugacagca aaucaaaga                                                    19

<210> SEQ ID NO 152
<211> LENGTH: 19
<212> TYPE: RNA
<213> ORGANISM: Artificial
<220> FEATURE:
<223> OTHER INFORMATION: siRNA, sense sequence

<400> SEQUENCE: 152
gacagcaaau caaagaaga                                                    19

<210> SEQ ID NO 153
<211> LENGTH: 19
<212> TYPE: RNA
<213> ORGANISM: Artificial
<220> FEATURE:
<223> OTHER INFORMATION: siRNA, sense sequence

<400> SEQUENCE: 153
cagcaaauca aagaagaaa                                                    19

<210> SEQ ID NO 154
<211> LENGTH: 19
<212> TYPE: RNA
<213> ORGANISM: Artificial
<220> FEATURE:
<223> OTHER INFORMATION: siRNA, sense sequence

<400> SEQUENCE: 154
gcaaaucaaa gaagaaaag                                                    19

<210> SEQ ID NO 155
<211> LENGTH: 19
<212> TYPE: RNA
<213> ORGANISM: Artificial
<220> FEATURE:
<223> OTHER INFORMATION: siRNA, sense sequence

<400> SEQUENCE: 155
gaagaaaaga gaugcugcu                                                    19

<210> SEQ ID NO 156
<211> LENGTH: 19
<212> TYPE: RNA
<213> ORGANISM: Artificial
<220> FEATURE:
<223> OTHER INFORMATION: siRNA, sense sequence

<400> SEQUENCE: 156
agaaaagaga ugcugcuga                                                    19

<210> SEQ ID NO 157
<211> LENGTH: 19
<212> TYPE: RNA
<213> ORGANISM: Artificial
<220> FEATURE:
<223> OTHER INFORMATION: siRNA, sense sequence

<400> SEQUENCE: 157
aaagagaugc ugcugacaa                                                    19

<210> SEQ ID NO 158
```

```
<211> LENGTH: 19
<212> TYPE: RNA
<213> ORGANISM: Artificial
<220> FEATURE:
<223> OTHER INFORMATION: siRNA, sense sequence

<400> SEQUENCE: 158
cugacaaacc aagaggauu                                                  19

<210> SEQ ID NO 159
<211> LENGTH: 19
<212> TYPE: RNA
<213> ORGANISM: Artificial
<220> FEATURE:
<223> OTHER INFORMATION: siRNA, sense sequence

<400> SEQUENCE: 159
accaagagga uuugccaga                                                  19

<210> SEQ ID NO 160
<211> LENGTH: 19
<212> TYPE: RNA
<213> ORGANISM: Artificial
<220> FEATURE:
<223> OTHER INFORMATION: siRNA, sense sequence

<400> SEQUENCE: 160
aggauuugcc agaggucuu                                                  19

<210> SEQ ID NO 161
<211> LENGTH: 19
<212> TYPE: RNA
<213> ORGANISM: Artificial
<220> FEATURE:
<223> OTHER INFORMATION: siRNA, sense sequence

<400> SEQUENCE: 161
ugccagaggu cuugauccu                                                  19

<210> SEQ ID NO 162
<211> LENGTH: 19
<212> TYPE: RNA
<213> ORGANISM: Artificial
<220> FEATURE:
<223> OTHER INFORMATION: siRNA, sense sequence

<400> SEQUENCE: 162
ccagaggucu ugauccuga                                                  19

<210> SEQ ID NO 163
<211> LENGTH: 19
<212> TYPE: RNA
<213> ORGANISM: Artificial
<220> FEATURE:
<223> OTHER INFORMATION: siRNA, sense sequence

<400> SEQUENCE: 163
aggucuugau ccugaaaga                                                  19

<210> SEQ ID NO 164
<211> LENGTH: 19
<212> TYPE: RNA
<213> ORGANISM: Artificial
<220> FEATURE:
<223> OTHER INFORMATION: siRNA, sense sequence

<400> SEQUENCE: 164
```

```
gucuugaucc ugaaagaau                                              19

<210> SEQ ID NO 165
<211> LENGTH: 19
<212> TYPE: RNA
<213> ORGANISM: Artificial
<220> FEATURE:
<223> OTHER INFORMATION: siRNA, sense sequence

<400> SEQUENCE: 165
ucuugauccu gaaagaaua                                              19

<210> SEQ ID NO 166
<211> LENGTH: 19
<212> TYPE: RNA
<213> ORGANISM: Artificial
<220> FEATURE:
<223> OTHER INFORMATION: siRNA, sense sequence

<400> SEQUENCE: 166
ccacagacag caguggaga                                              19

<210> SEQ ID NO 167
<211> LENGTH: 19
<212> TYPE: RNA
<213> ORGANISM: Artificial
<220> FEATURE:
<223> OTHER INFORMATION: siRNA, sense sequence

<400> SEQUENCE: 167
cacagacagc aguggagaa                                              19

<210> SEQ ID NO 168
<211> LENGTH: 19
<212> TYPE: RNA
<213> ORGANISM: Artificial
<220> FEATURE:
<223> OTHER INFORMATION: siRNA, sense sequence

<400> SEQUENCE: 168
acagacagca guggagaau                                              19

<210> SEQ ID NO 169
<211> LENGTH: 19
<212> TYPE: RNA
<213> ORGANISM: Artificial
<220> FEATURE:
<223> OTHER INFORMATION: siRNA, sense sequence

<400> SEQUENCE: 169
guggagaauu gauguuucu                                              19

<210> SEQ ID NO 170
<211> LENGTH: 19
<212> TYPE: RNA
<213> ORGANISM: Artificial
<220> FEATURE:
<223> OTHER INFORMATION: siRNA, sense sequence

<400> SEQUENCE: 170
gagaauugau guuucucau                                              19

<210> SEQ ID NO 171
<211> LENGTH: 19
<212> TYPE: RNA
```

```
<213> ORGANISM: Artificial
<220> FEATURE:
<223> OTHER INFORMATION: siRNA, sense sequence

<400> SEQUENCE: 171
gaauugaugu uucucauga                                                    19

<210> SEQ ID NO 172
<211> LENGTH: 19
<212> TYPE: RNA
<213> ORGANISM: Artificial
<220> FEATURE:
<223> OTHER INFORMATION: siRNA, sense sequence

<400> SEQUENCE: 172
caugaaaugg aaagauuca                                                    19

<210> SEQ ID NO 173
<211> LENGTH: 19
<212> TYPE: RNA
<213> ORGANISM: Artificial
<220> FEATURE:
<223> OTHER INFORMATION: siRNA, sense sequence

<400> SEQUENCE: 173
ugaaauggaa agauucaga                                                    19

<210> SEQ ID NO 174
<211> LENGTH: 19
<212> TYPE: RNA
<213> ORGANISM: Artificial
<220> FEATURE:
<223> OTHER INFORMATION: siRNA, sense sequence

<400> SEQUENCE: 174
ggaaagauuc agaugaggc                                                    19

<210> SEQ ID NO 175
<211> LENGTH: 19
<212> TYPE: RNA
<213> ORGANISM: Artificial
<220> FEATURE:
<223> OTHER INFORMATION: siRNA, sense sequence

<400> SEQUENCE: 175
gaaagauuca gaugaggca                                                    19

<210> SEQ ID NO 176
<211> LENGTH: 19
<212> TYPE: RNA
<213> ORGANISM: Artificial
<220> FEATURE:
<223> OTHER INFORMATION: siRNA, sense sequence

<400> SEQUENCE: 176
aagauucaga ugaggcaga                                                    19

<210> SEQ ID NO 177
<211> LENGTH: 19
<212> TYPE: RNA
<213> ORGANISM: Artificial
<220> FEATURE:
<223> OTHER INFORMATION: siRNA, sense sequence

<400> SEQUENCE: 177
agacuuggug cuggcgaaa                                                    19
```

```
<210> SEQ ID NO 178
<211> LENGTH: 19
<212> TYPE: RNA
<213> ORGANISM: Artificial
<220> FEATURE:
<223> OTHER INFORMATION: siRNA, sense sequence

<400> SEQUENCE: 178
acuuggugcu ggcgaaaga                                                19

<210> SEQ ID NO 179
<211> LENGTH: 19
<212> TYPE: RNA
<213> ORGANISM: Artificial
<220> FEATURE:
<223> OTHER INFORMATION: siRNA, sense sequence

<400> SEQUENCE: 179
ggugcuggcg aaagaggca                                                19

<210> SEQ ID NO 180
<211> LENGTH: 19
<212> TYPE: RNA
<213> ORGANISM: Artificial
<220> FEATURE:
<223> OTHER INFORMATION: siRNA, sense sequence

<400> SEQUENCE: 180
uggcgaaaga ggcaaauau                                                19

<210> SEQ ID NO 181
<211> LENGTH: 19
<212> TYPE: RNA
<213> ORGANISM: Artificial
<220> FEATURE:
<223> OTHER INFORMATION: siRNA, sense sequence

<400> SEQUENCE: 181
aggcaaauau gaagugucc                                                19

<210> SEQ ID NO 182
<211> LENGTH: 19
<212> TYPE: RNA
<213> ORGANISM: Artificial
<220> FEATURE:
<223> OTHER INFORMATION: siRNA, sense sequence

<400> SEQUENCE: 182
gcaaauauga aguguccuc                                                19

<210> SEQ ID NO 183
<211> LENGTH: 19
<212> TYPE: RNA
<213> ORGANISM: Artificial
<220> FEATURE:
<223> OTHER INFORMATION: siRNA, sense sequence

<400> SEQUENCE: 183
aauaugaagu guccucaaa                                                19

<210> SEQ ID NO 184
<211> LENGTH: 19
<212> TYPE: RNA
<213> ORGANISM: Artificial
<220> FEATURE:
```

<223> OTHER INFORMATION: siRNA, sense sequence

<400> SEQUENCE: 184
ccucaaauug uaauugcuu                    19

<210> SEQ ID NO 185
<211> LENGTH: 19
<212> TYPE: RNA
<213> ORGANISM: Artificial
<220> FEATURE:
<223> OTHER INFORMATION: siRNA, sense sequence

<400> SEQUENCE: 185
agagagacua acuuggcau                    19

<210> SEQ ID NO 186
<211> LENGTH: 19
<212> TYPE: RNA
<213> ORGANISM: Artificial
<220> FEATURE:
<223> OTHER INFORMATION: siRNA, sense sequence

<400> SEQUENCE: 186
gagagacuaa cuuggcauu                    19

<210> SEQ ID NO 187
<211> LENGTH: 19
<212> TYPE: RNA
<213> ORGANISM: Artificial
<220> FEATURE:
<223> OTHER INFORMATION: siRNA, sense sequence

<400> SEQUENCE: 187
gcauucuugu ccagaagau                    19

<210> SEQ ID NO 188
<211> LENGTH: 19
<212> TYPE: RNA
<213> ORGANISM: Artificial
<220> FEATURE:
<223> OTHER INFORMATION: siRNA, sense sequence

<400> SEQUENCE: 188
guccagaaga ugaagcuca                    19

<210> SEQ ID NO 189
<211> LENGTH: 19
<212> TYPE: RNA
<213> ORGANISM: Artificial
<220> FEATURE:
<223> OTHER INFORMATION: siRNA, sense sequence

<400> SEQUENCE: 189
uccagaagau gaagcucaa                    19

<210> SEQ ID NO 190
<211> LENGTH: 19
<212> TYPE: RNA
<213> ORGANISM: Artificial
<220> FEATURE:
<223> OTHER INFORMATION: siRNA, sense sequence

<400> SEQUENCE: 190
agaagaugaa gcucaauaa                    19

```
<210> SEQ ID NO 191
<211> LENGTH: 19
<212> TYPE: RNA
<213> ORGANISM: Artificial
<220> FEATURE:
<223> OTHER INFORMATION: siRNA, sense sequence

<400> SEQUENCE: 191
ggucaugaug aauggaaua                                                  19

<210> SEQ ID NO 192
<211> LENGTH: 19
<212> TYPE: RNA
<213> ORGANISM: Artificial
<220> FEATURE:
<223> OTHER INFORMATION: siRNA, antisense sequence

<400> SEQUENCE: 192
uugcaaugua guuuguug                                                   19

<210> SEQ ID NO 193
<211> LENGTH: 19
<212> TYPE: RNA
<213> ORGANISM: Artificial
<220> FEATURE:
<223> OTHER INFORMATION: siRNA, antisense sequence

<400> SEQUENCE: 193
acucuuucca uucuguuuu                                                  19

<210> SEQ ID NO 194
<211> LENGTH: 19
<212> TYPE: RNA
<213> ORGANISM: Artificial
<220> FEATURE:
<223> OTHER INFORMATION: siRNA, antisense sequence

<400> SEQUENCE: 194
uacucuuucc auucuguuu                                                  19

<210> SEQ ID NO 195
<211> LENGTH: 19
<212> TYPE: RNA
<213> ORGANISM: Artificial
<220> FEATURE:
<223> OTHER INFORMATION: siRNA, antisense sequence

<400> SEQUENCE: 195
uuacucuuuc cauucuguu                                                  19

<210> SEQ ID NO 196
<211> LENGTH: 19
<212> TYPE: RNA
<213> ORGANISM: Artificial
<220> FEATURE:
<223> OTHER INFORMATION: siRNA, antisense sequence

<400> SEQUENCE: 196
uuuuacucuu uccauucug                                                  19

<210> SEQ ID NO 197
<211> LENGTH: 19
<212> TYPE: RNA
<213> ORGANISM: Artificial
<220> FEATURE:
<223> OTHER INFORMATION: siRNA, antisense sequence
```

<400> SEQUENCE: 197
ucugccucuu caacuuuuu                                                        19

<210> SEQ ID NO 198
<211> LENGTH: 19
<212> TYPE: RNA
<213> ORGANISM: Artificial
<220> FEATURE:
<223> OTHER INFORMATION: siRNA, antisense sequence

<400> SEQUENCE: 198
aggcucugcc ucuucaacu                                                        19

<210> SEQ ID NO 199
<211> LENGTH: 19
<212> TYPE: RNA
<213> ORGANISM: Artificial
<220> FEATURE:
<223> OTHER INFORMATION: siRNA, antisense sequence

<400> SEQUENCE: 199
ucaggcucug ccucuucaa                                                        19

<210> SEQ ID NO 200
<211> LENGTH: 19
<212> TYPE: RNA
<213> ORGANISM: Artificial
<220> FEATURE:
<223> OTHER INFORMATION: siRNA, antisense sequence

<400> SEQUENCE: 200
aauucuucag gcucugccu                                                        19

<210> SEQ ID NO 201
<211> LENGTH: 19
<212> TYPE: RNA
<213> ORGANISM: Artificial
<220> FEATURE:
<223> OTHER INFORMATION: siRNA, antisense sequence

<400> SEQUENCE: 201
aaauucuuca ggcucugcc                                                        19

<210> SEQ ID NO 202
<211> LENGTH: 19
<212> TYPE: RNA
<213> ORGANISM: Artificial
<220> FEATURE:
<223> OTHER INFORMATION: siRNA, antisense sequence

<400> SEQUENCE: 202
uccacgacaa auucuucag                                                        19

<210> SEQ ID NO 203
<211> LENGTH: 19
<212> TYPE: RNA
<213> ORGANISM: Artificial
<220> FEATURE:
<223> OTHER INFORMATION: siRNA, antisense sequence

<400> SEQUENCE: 203
uuccacgaca aauucuuca                                                        19

<210> SEQ ID NO 204
<211> LENGTH: 19

```
<212> TYPE: RNA
<213> ORGANISM: Artificial
<220> FEATURE:
<223> OTHER INFORMATION: siRNA, antisense sequence

<400> SEQUENCE: 204
uuuuccacga caaauucuu                                              19

<210> SEQ ID NO 205
<211> LENGTH: 19
<212> TYPE: RNA
<213> ORGANISM: Artificial
<220> FEATURE:
<223> OTHER INFORMATION: siRNA, antisense sequence

<400> SEQUENCE: 205
uuuuuccacg acaaauucu                                              19

<210> SEQ ID NO 206
<211> LENGTH: 19
<212> TYPE: RNA
<213> ORGANISM: Artificial
<220> FEATURE:
<223> OTHER INFORMATION: siRNA, antisense sequence

<400> SEQUENCE: 206
uaguacuuuu uccacgaca                                              19

<210> SEQ ID NO 207
<211> LENGTH: 19
<212> TYPE: RNA
<213> ORGANISM: Artificial
<220> FEATURE:
<223> OTHER INFORMATION: siRNA, antisense sequence

<400> SEQUENCE: 207
cgaucuagua cuuuuucca                                              19

<210> SEQ ID NO 208
<211> LENGTH: 19
<212> TYPE: RNA
<213> ORGANISM: Artificial
<220> FEATURE:
<223> OTHER INFORMATION: siRNA, antisense sequence

<400> SEQUENCE: 208
ucgaucuagu acuuuuucc                                              19

<210> SEQ ID NO 209
<211> LENGTH: 19
<212> TYPE: RNA
<213> ORGANISM: Artificial
<220> FEATURE:
<223> OTHER INFORMATION: siRNA, antisense sequence

<400> SEQUENCE: 209
uacacgucga ucuaguacu                                              19

<210> SEQ ID NO 210
<211> LENGTH: 19
<212> TYPE: RNA
<213> ORGANISM: Artificial
<220> FEATURE:
<223> OTHER INFORMATION: siRNA, antisense sequence

<400> SEQUENCE: 210
```
auucacuaca cgucgaucu                                                    19

<210> SEQ ID NO 211
<211> LENGTH: 19
<212> TYPE: RNA
<213> ORGANISM: Artificial
<220> FEATURE:
<223> OTHER INFORMATION: siRNA, antisense sequence

<400> SEQUENCE: 211
uucccauuca cuacacguc                                                    19

<210> SEQ ID NO 212
<211> LENGTH: 19
<212> TYPE: RNA
<213> ORGANISM: Artificial
<220> FEATURE:
<223> OTHER INFORMATION: siRNA, antisense sequence

<400> SEQUENCE: 212
uuucccauuc acuacacgu                                                    19

<210> SEQ ID NO 213
<211> LENGTH: 19
<212> TYPE: RNA
<213> ORGANISM: Artificial
<220> FEATURE:
<223> OTHER INFORMATION: siRNA, antisense sequence

<400> SEQUENCE: 213
uuccacuuuc ccauucacu                                                    19

<210> SEQ ID NO 214
<211> LENGTH: 19
<212> TYPE: RNA
<213> ORGANISM: Artificial
<220> FEATURE:
<223> OTHER INFORMATION: siRNA, antisense sequence

<400> SEQUENCE: 214
auuccacuuu cccauucac                                                    19

<210> SEQ ID NO 215
<211> LENGTH: 19
<212> TYPE: RNA
<213> ORGANISM: Artificial
<220> FEATURE:
<223> OTHER INFORMATION: siRNA, antisense sequence

<400> SEQUENCE: 215
uauuccacuu ucccauuca                                                    19

<210> SEQ ID NO 216
<211> LENGTH: 19
<212> TYPE: RNA
<213> ORGANISM: Artificial
<220> FEATURE:
<223> OTHER INFORMATION: siRNA, antisense sequence

<400> SEQUENCE: 216
aucccuucca cuucaggaa                                                    19

<210> SEQ ID NO 217
<211> LENGTH: 19
<212> TYPE: RNA
<213> ORGANISM: Artificial

-continued

```
<220> FEATURE:
<223> OTHER INFORMATION: siRNA, antisense sequence

<400> SEQUENCE: 217
aaucccuucc acuucagga                                                      19

<210> SEQ ID NO 218
<211> LENGTH: 19
<212> TYPE: RNA
<213> ORGANISM: Artificial
<220> FEATURE:
<223> OTHER INFORMATION: siRNA, antisense sequence

<400> SEQUENCE: 218
uaaaucccuu ccacuucag                                                      19

<210> SEQ ID NO 219
<211> LENGTH: 19
<212> TYPE: RNA
<213> ORGANISM: Artificial
<220> FEATURE:
<223> OTHER INFORMATION: siRNA, antisense sequence

<400> SEQUENCE: 219
aucuguaaau cccuuccac                                                      19

<210> SEQ ID NO 220
<211> LENGTH: 19
<212> TYPE: RNA
<213> ORGANISM: Artificial
<220> FEATURE:
<223> OTHER INFORMATION: siRNA, antisense sequence

<400> SEQUENCE: 220
caucuguaaa ucccuucca                                                      19

<210> SEQ ID NO 221
<211> LENGTH: 19
<212> TYPE: RNA
<213> ORGANISM: Artificial
<220> FEATURE:
<223> OTHER INFORMATION: siRNA, antisense sequence

<400> SEQUENCE: 221
auugucagca ucuguaaau                                                      19

<210> SEQ ID NO 222
<211> LENGTH: 19
<212> TYPE: RNA
<213> ORGANISM: Artificial
<220> FEATURE:
<223> OTHER INFORMATION: siRNA, antisense sequence

<400> SEQUENCE: 222
guucccaagu auugucagc                                                      19

<210> SEQ ID NO 223
<211> LENGTH: 19
<212> TYPE: RNA
<213> ORGANISM: Artificial
<220> FEATURE:
<223> OTHER INFORMATION: siRNA, antisense sequence

<400> SEQUENCE: 223
agguucccaa guauuguca                                                      19
```

<210> SEQ ID NO 224
<211> LENGTH: 19
<212> TYPE: RNA
<213> ORGANISM: Artificial
<220> FEATURE:
<223> OTHER INFORMATION: siRNA, antisense sequence

<400> SEQUENCE: 224
uuuucuucag guucccaag                                                    19

<210> SEQ ID NO 225
<211> LENGTH: 19
<212> TYPE: RNA
<213> ORGANISM: Artificial
<220> FEATURE:
<223> OTHER INFORMATION: siRNA, antisense sequence

<400> SEQUENCE: 225
auuuucuuca gguucccaa                                                    19

<210> SEQ ID NO 226
<211> LENGTH: 19
<212> TYPE: RNA
<213> ORGANISM: Artificial
<220> FEATURE:
<223> OTHER INFORMATION: siRNA, antisense sequence

<400> SEQUENCE: 226
aacgcuucaa ucaauucug                                                    19

<210> SEQ ID NO 227
<211> LENGTH: 19
<212> TYPE: RNA
<213> ORGANISM: Artificial
<220> FEATURE:
<223> OTHER INFORMATION: siRNA, antisense sequence

<400> SEQUENCE: 227
aaacgcuuca aucaauucu                                                    19

<210> SEQ ID NO 228
<211> LENGTH: 19
<212> TYPE: RNA
<213> ORGANISM: Artificial
<220> FEATURE:
<223> OTHER INFORMATION: siRNA, antisense sequence

<400> SEQUENCE: 228
uuaagaaacg cuucaauca                                                    19

<210> SEQ ID NO 229
<211> LENGTH: 19
<212> TYPE: RNA
<213> ORGANISM: Artificial
<220> FEATURE:
<223> OTHER INFORMATION: siRNA, antisense sequence

<400> SEQUENCE: 229
uuucugagag uuaagaaac                                                    19

<210> SEQ ID NO 230
<211> LENGTH: 19
<212> TYPE: RNA
<213> ORGANISM: Artificial
<220> FEATURE:
<223> OTHER INFORMATION: siRNA, antisense sequence -continued

```
<400> SEQUENCE: 230
uucuuugcca gcuuucuga                                              19

<210> SEQ ID NO 231
<211> LENGTH: 19
<212> TYPE: RNA
<213> ORGANISM: Artificial
<220> FEATURE:
<223> OTHER INFORMATION: siRNA, antisense sequence

<400> SEQUENCE: 231
uuucuuugcc agcuuucug                                              19

<210> SEQ ID NO 232
<211> LENGTH: 19
<212> TYPE: RNA
<213> ORGANISM: Artificial
<220> FEATURE:
<223> OTHER INFORMATION: siRNA, antisense sequence

<400> SEQUENCE: 232
uuuucuuugc cagcuuucu                                              19

<210> SEQ ID NO 233
<211> LENGTH: 19
<212> TYPE: RNA
<213> ORGANISM: Artificial
<220> FEATURE:
<223> OTHER INFORMATION: siRNA, antisense sequence

<400> SEQUENCE: 233
uuuuucuuug ccagcuuuc                                              19

<210> SEQ ID NO 234
<211> LENGTH: 19
<212> TYPE: RNA
<213> ORGANISM: Artificial
<220> FEATURE:
<223> OTHER INFORMATION: siRNA, antisense sequence

<400> SEQUENCE: 234
accaucuuuu ucuuugcca                                              19

<210> SEQ ID NO 235
<211> LENGTH: 19
<212> TYPE: RNA
<213> ORGANISM: Artificial
<220> FEATURE:
<223> OTHER INFORMATION: siRNA, antisense sequence

<400> SEQUENCE: 235
guaccaucuu uuucuuugc                                              19

<210> SEQ ID NO 236
<211> LENGTH: 19
<212> TYPE: RNA
<213> ORGANISM: Artificial
<220> FEATURE:
<223> OTHER INFORMATION: siRNA, antisense sequence

<400> SEQUENCE: 236
uguaccaucu uuucuuug                                               19

<210> SEQ ID NO 237
```

```
<210> SEQ ID NO 237
<211> LENGTH: 19
<212> TYPE: RNA
<213> ORGANISM: Artificial
<220> FEATURE:
<223> OTHER INFORMATION: siRNA, antisense sequence

<400> SEQUENCE: 237
ucacugucag auaaagauu                                                  19

<210> SEQ ID NO 238
<211> LENGTH: 19
<212> TYPE: RNA
<213> ORGANISM: Artificial
<220> FEATURE:
<223> OTHER INFORMATION: siRNA, antisense sequence

<400> SEQUENCE: 238
uugcugucau cagauucac                                                  19

<210> SEQ ID NO 239
<211> LENGTH: 19
<212> TYPE: RNA
<213> ORGANISM: Artificial
<220> FEATURE:
<223> OTHER INFORMATION: siRNA, antisense sequence

<400> SEQUENCE: 239
auuugcuguc aucagauuc                                                  19

<210> SEQ ID NO 240
<211> LENGTH: 19
<212> TYPE: RNA
<213> ORGANISM: Artificial
<220> FEATURE:
<223> OTHER INFORMATION: siRNA, antisense sequence

<400> SEQUENCE: 240
ucuuugauuu gcugucauc                                                  19

<210> SEQ ID NO 241
<211> LENGTH: 19
<212> TYPE: RNA
<213> ORGANISM: Artificial
<220> FEATURE:
<223> OTHER INFORMATION: siRNA, antisense sequence

<400> SEQUENCE: 241
ucuucuuuga uuugcuguc                                                  19

<210> SEQ ID NO 242
<211> LENGTH: 19
<212> TYPE: RNA
<213> ORGANISM: Artificial
<220> FEATURE:
<223> OTHER INFORMATION: siRNA, antisense sequence

<400> SEQUENCE: 242
uucuucuuug auuugcugu                                                  19

<210> SEQ ID NO 243
<211> LENGTH: 19
<212> TYPE: RNA
<213> ORGANISM: Artificial
<220> FEATURE:
<223> OTHER INFORMATION: siRNA, antisense sequence

<400> SEQUENCE: 243
```
uuucuucuuu gauuugcug    19

<210> SEQ ID NO 244
<211> LENGTH: 19
<212> TYPE: RNA
<213> ORGANISM: Artificial
<220> FEATURE:
<223> OTHER INFORMATION: siRNA, antisense sequence

<400> SEQUENCE: 244 cuuucuucu uugauuugc    19

<210> SEQ ID NO 245
<211> LENGTH: 19
<212> TYPE: RNA
<213> ORGANISM: Artificial
<220> FEATURE:
<223> OTHER INFORMATION: siRNA, antisense sequence

<400> SEQUENCE: 245
caucucuuuu cuucuuuga    19

<210> SEQ ID NO 246
<211> LENGTH: 19
<212> TYPE: RNA
<213> ORGANISM: Artificial
<220> FEATURE:
<223> OTHER INFORMATION: siRNA, antisense sequence

<400> SEQUENCE: 246
agcagcaucu cuuucuuc    19

<210> SEQ ID NO 247
<211> LENGTH: 19
<212> TYPE: RNA
<213> ORGANISM: Artificial
<220> FEATURE:
<223> OTHER INFORMATION: siRNA, antisense sequence

<400> SEQUENCE: 247
ucagcagcau cucuuuucu    19

<210> SEQ ID NO 248
<211> LENGTH: 19
<212> TYPE: RNA
<213> ORGANISM: Artificial
<220> FEATURE:
<223> OTHER INFORMATION: siRNA, antisense sequence

<400> SEQUENCE: 248
gucagcagca ucucuuuc    19

<210> SEQ ID NO 249
<211> LENGTH: 19
<212> TYPE: RNA
<213> ORGANISM: Artificial
<220> FEATURE:
<223> OTHER INFORMATION: siRNA, antisense sequence

<400> SEQUENCE: 249
uugucagcag caucucuuu    19

<210> SEQ ID NO 250
<211> LENGTH: 19
<212> TYPE: RNA

```
<213> ORGANISM: Artificial
<220> FEATURE:
<223> OTHER INFORMATION: siRNA, antisense sequence

<400> SEQUENCE: 250
uuugucagca gcaucucuu                                                      19

<210> SEQ ID NO 251
<211> LENGTH: 19
<212> TYPE: RNA
<213> ORGANISM: Artificial
<220> FEATURE:
<223> OTHER INFORMATION: siRNA, antisense sequence

<400> SEQUENCE: 251
auccucuugg uuugucagc                                                      19

<210> SEQ ID NO 252
<211> LENGTH: 19
<212> TYPE: RNA
<213> ORGANISM: Artificial
<220> FEATURE:
<223> OTHER INFORMATION: siRNA, antisense sequence

<400> SEQUENCE: 252
aauccucuug guuugucag                                                      19

<210> SEQ ID NO 253
<211> LENGTH: 19
<212> TYPE: RNA
<213> ORGANISM: Artificial
<220> FEATURE:
<223> OTHER INFORMATION: siRNA, antisense sequence

<400> SEQUENCE: 253
aaauccucuu gguuuguca                                                      19

<210> SEQ ID NO 254
<211> LENGTH: 19
<212> TYPE: RNA
<213> ORGANISM: Artificial
<220> FEATURE:
<223> OTHER INFORMATION: siRNA, antisense sequence

<400> SEQUENCE: 254
ucuggcaaau ccucuuggu                                                      19

<210> SEQ ID NO 255
<211> LENGTH: 19
<212> TYPE: RNA
<213> ORGANISM: Artificial
<220> FEATURE:
<223> OTHER INFORMATION: siRNA, antisense sequence

<400> SEQUENCE: 255
aagaccucug gcaaauccu                                                      19

<210> SEQ ID NO 256
<211> LENGTH: 19
<212> TYPE: RNA
<213> ORGANISM: Artificial
<220> FEATURE:
<223> OTHER INFORMATION: siRNA, antisense sequence

<400> SEQUENCE: 256
aggaucaaga ccucuggca                                                      19
```

```
<210> SEQ ID NO 257
<211> LENGTH: 19
<212> TYPE: RNA
<213> ORGANISM: Artificial
<220> FEATURE:
<223> OTHER INFORMATION: siRNA, antisense sequence

<400> SEQUENCE: 257
ucaggaucaa gaccucugg                                                        19

<210> SEQ ID NO 258
<211> LENGTH: 19
<212> TYPE: RNA
<213> ORGANISM: Artificial
<220> FEATURE:
<223> OTHER INFORMATION: siRNA, antisense sequence

<400> SEQUENCE: 258
ucuuucagga ucaagaccu                                                        19

<210> SEQ ID NO 259
<211> LENGTH: 19
<212> TYPE: RNA
<213> ORGANISM: Artificial
<220> FEATURE:
<223> OTHER INFORMATION: siRNA, antisense sequence

<400> SEQUENCE: 259
auucuuucag gaucaagac                                                        19

<210> SEQ ID NO 260
<211> LENGTH: 19
<212> TYPE: RNA
<213> ORGANISM: Artificial
<220> FEATURE:
<223> OTHER INFORMATION: siRNA, antisense sequence

<400> SEQUENCE: 260
uauucuuuca ggaucaaga                                                        19

<210> SEQ ID NO 261
<211> LENGTH: 19
<212> TYPE: RNA
<213> ORGANISM: Artificial
<220> FEATURE:
<223> OTHER INFORMATION: siRNA, antisense sequence

<400> SEQUENCE: 261
ucuccacugc ugucugugg                                                        19

<210> SEQ ID NO 262
<211> LENGTH: 19
<212> TYPE: RNA
<213> ORGANISM: Artificial
<220> FEATURE:
<223> OTHER INFORMATION: siRNA, antisense sequence

<400> SEQUENCE: 262
uucuccacug cugucugug                                                        19

<210> SEQ ID NO 263
<211> LENGTH: 19
<212> TYPE: RNA
<213> ORGANISM: Artificial
<220> FEATURE:
```

<223> OTHER INFORMATION: siRNA, antisense sequence

<400> SEQUENCE: 263
auucuccacu gcugucugu                                                        19

<210> SEQ ID NO 264
<211> LENGTH: 19
<212> TYPE: RNA
<213> ORGANISM: Artificial
<220> FEATURE:
<223> OTHER INFORMATION: siRNA, antisense sequence

<400> SEQUENCE: 264
caauucucca cugcugucu                                                        19

<210> SEQ ID NO 265
<211> LENGTH: 19
<212> TYPE: RNA
<213> ORGANISM: Artificial
<220> FEATURE:
<223> OTHER INFORMATION: siRNA, antisense sequence

<400> SEQUENCE: 265
agaaacauca auucuccac                                                        19

<210> SEQ ID NO 266
<211> LENGTH: 19
<212> TYPE: RNA
<213> ORGANISM: Artificial
<220> FEATURE:
<223> OTHER INFORMATION: siRNA, antisense sequence

<400> SEQUENCE: 266
augagaaaca ucaauucuc                                                        19

<210> SEQ ID NO 267
<211> LENGTH: 19
<212> TYPE: RNA
<213> ORGANISM: Artificial
<220> FEATURE:
<223> OTHER INFORMATION: siRNA, antisense sequence

<400> SEQUENCE: 267
ucaugagaaa caucaauuc                                                        19

<210> SEQ ID NO 268
<211> LENGTH: 19
<212> TYPE: RNA
<213> ORGANISM: Artificial
<220> FEATURE:
<223> OTHER INFORMATION: siRNA, antisense sequence

<400> SEQUENCE: 268
aaucuuucca uuucaugag                                                        19

<210> SEQ ID NO 269
<211> LENGTH: 19
<212> TYPE: RNA
<213> ORGANISM: Artificial
<220> FEATURE:
<223> OTHER INFORMATION: siRNA, antisense sequence

<400> SEQUENCE: 269
ugaaucuuuc cauuucaug                                                        19

```
<210> SEQ ID NO 270
<211> LENGTH: 19
<212> TYPE: RNA
<213> ORGANISM: Artificial
<220> FEATURE:
<223> OTHER INFORMATION: siRNA, antisense sequence

<400> SEQUENCE: 270
ucugaaucuu uccauuuca                                                   19

<210> SEQ ID NO 271
<211> LENGTH: 19
<212> TYPE: RNA
<213> ORGANISM: Artificial
<220> FEATURE:
<223> OTHER INFORMATION: siRNA, antisense sequence

<400> SEQUENCE: 271
gccucaucug aaucuuucc                                                   19

<210> SEQ ID NO 272
<211> LENGTH: 19
<212> TYPE: RNA
<213> ORGANISM: Artificial
<220> FEATURE:
<223> OTHER INFORMATION: siRNA, antisense sequence

<400> SEQUENCE: 272
ugccucaucu gaaucuuuc                                                   19

<210> SEQ ID NO 273
<211> LENGTH: 19
<212> TYPE: RNA
<213> ORGANISM: Artificial
<220> FEATURE:
<223> OTHER INFORMATION: siRNA, antisense sequence

<400> SEQUENCE: 273
ucugccucau cugaaucuu                                                   19

<210> SEQ ID NO 274
<211> LENGTH: 19
<212> TYPE: RNA
<213> ORGANISM: Artificial
<220> FEATURE:
<223> OTHER INFORMATION: siRNA, antisense sequence

<400> SEQUENCE: 274
uucgccagca ccaagucug                                                   19

<210> SEQ ID NO 275
<211> LENGTH: 19
<212> TYPE: RNA
<213> ORGANISM: Artificial
<220> FEATURE:
<223> OTHER INFORMATION: siRNA, antisense sequence

<400> SEQUENCE: 275
uuucgccagc accaagucu                                                   19

<210> SEQ ID NO 276
<211> LENGTH: 19
<212> TYPE: RNA
<213> ORGANISM: Artificial
<220> FEATURE:
<223> OTHER INFORMATION: siRNA, antisense sequence
```

```
<400> SEQUENCE: 276
ucuuucgcca gcaccaagu                                              19

<210> SEQ ID NO 277
<211> LENGTH: 19
<212> TYPE: RNA
<213> ORGANISM: Artificial
<220> FEATURE:
<223> OTHER INFORMATION: siRNA, antisense sequence

<400> SEQUENCE: 277
ugccucuuuc gccagcacc                                              19

<210> SEQ ID NO 278
<211> LENGTH: 19
<212> TYPE: RNA
<213> ORGANISM: Artificial
<220> FEATURE:
<223> OTHER INFORMATION: siRNA, antisense sequence

<400> SEQUENCE: 278
auauuugccu cuuucgcca                                              19

<210> SEQ ID NO 279
<211> LENGTH: 19
<212> TYPE: RNA
<213> ORGANISM: Artificial
<220> FEATURE:
<223> OTHER INFORMATION: siRNA, antisense sequence

<400> SEQUENCE: 279
ucauauuugc cucuuucgc                                              19

<210> SEQ ID NO 280
<211> LENGTH: 19
<212> TYPE: RNA
<213> ORGANISM: Artificial
<220> FEATURE:
<223> OTHER INFORMATION: siRNA, antisense sequence

<400> SEQUENCE: 280
uucauauuug ccucuuucg                                              19

<210> SEQ ID NO 281
<211> LENGTH: 19
<212> TYPE: RNA
<213> ORGANISM: Artificial
<220> FEATURE:
<223> OTHER INFORMATION: siRNA, antisense sequence

<400> SEQUENCE: 281
ggacacuuca uauuugccu                                              19

<210> SEQ ID NO 282
<211> LENGTH: 19
<212> TYPE: RNA
<213> ORGANISM: Artificial
<220> FEATURE:
<223> OTHER INFORMATION: siRNA, antisense sequence

<400> SEQUENCE: 282
gaggacacuu cauauuugc                                              19

<210> SEQ ID NO 283
<211> LENGTH: 19
```

```
<212> TYPE: RNA
<213> ORGANISM: Artificial
<220> FEATURE:
<223> OTHER INFORMATION: siRNA, antisense sequence

<400> SEQUENCE: 283
uuugaggaca cuucauauu                                                    19

<210> SEQ ID NO 284
<211> LENGTH: 19
<212> TYPE: RNA
<213> ORGANISM: Artificial
<220> FEATURE:
<223> OTHER INFORMATION: siRNA, antisense sequence

<400> SEQUENCE: 284
aagcaauuac aauuugagg                                                    19

<210> SEQ ID NO 285
<211> LENGTH: 19
<212> TYPE: RNA
<213> ORGANISM: Artificial
<220> FEATURE:
<223> OTHER INFORMATION: siRNA, antisense sequence

<400> SEQUENCE: 285
augccaaguu agucucucu                                                    19

<210> SEQ ID NO 286
<211> LENGTH: 19
<212> TYPE: RNA
<213> ORGANISM: Artificial
<220> FEATURE:
<223> OTHER INFORMATION: siRNA, antisense sequence

<400> SEQUENCE: 286
aaugccaagu uagucucuc                                                    19

<210> SEQ ID NO 287
<211> LENGTH: 19
<212> TYPE: RNA
<213> ORGANISM: Artificial
<220> FEATURE:
<223> OTHER INFORMATION: siRNA, antisense sequence

<400> SEQUENCE: 287
aucuucugga caagaaugc                                                    19

<210> SEQ ID NO 288
<211> LENGTH: 19
<212> TYPE: RNA
<213> ORGANISM: Artificial
<220> FEATURE:
<223> OTHER INFORMATION: siRNA, antisense sequence

<400> SEQUENCE: 288
ugagcuucau cuucuggac                                                    19

<210> SEQ ID NO 289
<211> LENGTH: 19
<212> TYPE: RNA
<213> ORGANISM: Artificial
<220> FEATURE:
<223> OTHER INFORMATION: siRNA, antisense sequence

<400> SEQUENCE: 289
```

| | |
|---|---|
| uugagcuuca ucuucugga | 19 |

<210> SEQ ID NO 290
<211> LENGTH: 19
<212> TYPE: RNA
<213> ORGANISM: Artificial
<220> FEATURE:
<223> OTHER INFORMATION: siRNA, antisense sequence

<400> SEQUENCE: 290

| | |
|---|---|
| uauugagcuu caucuucug | 19 |

<210> SEQ ID NO 291
<211> LENGTH: 19
<212> TYPE: RNA
<213> ORGANISM: Artificial
<220> FEATURE:
<223> OTHER INFORMATION: siRNA, antisense sequence

<400> SEQUENCE: 291

| | |
|---|---|
| uuauugagcu ucaucuucu | 19 |

<210> SEQ ID NO 292
<211> LENGTH: 19
<212> TYPE: RNA
<213> ORGANISM: Artificial
<220> FEATURE:
<223> OTHER INFORMATION: siRNA, antisense sequence

<400> SEQUENCE: 292

| | |
|---|---|
| uuaacuugaa gggauuauc | 19 |

<210> SEQ ID NO 293
<211> LENGTH: 19
<212> TYPE: RNA
<213> ORGANISM: Artificial
<220> FEATURE:
<223> OTHER INFORMATION: siRNA, antisense sequence

<400> SEQUENCE: 293

| | |
|---|---|
| uuucacuuga aauguaugg | 19 |

<210> SEQ ID NO 294
<211> LENGTH: 19
<212> TYPE: RNA
<213> ORGANISM: Artificial
<220> FEATURE:
<223> OTHER INFORMATION: siRNA, antisense sequence

<400> SEQUENCE: 294

| | |
|---|---|
| aaacacacua gcauuuguc | 19 |

<210> SEQ ID NO 295
<211> LENGTH: 19
<212> TYPE: RNA
<213> ORGANISM: Artificial
<220> FEATURE:
<223> OTHER INFORMATION: siRNA, antisense sequence

<400> SEQUENCE: 295

| | |
|---|---|
| uuuugcuaag gaauggccc | 19 |

<210> SEQ ID NO 296
<211> LENGTH: 19
<212> TYPE: RNA
<213> ORGANISM: Artificial

```
<220> FEATURE:
<223> OTHER INFORMATION: siRNA, antisense sequence

<400> SEQUENCE: 296
uauuccauuc aucaugacc                                                      19

<210> SEQ ID NO 297
<211> LENGTH: 19
<212> TYPE: RNA
<213> ORGANISM: Artificial
<220> FEATURE:
<223> OTHER INFORMATION: siRNA, antisense sequence

<400> SEQUENCE: 297
uucuuccugg cuuuugcug                                                      19
```